(12) United States Patent  
Larch et al.

(10) Patent No.: US 8,691,979 B2  
(45) Date of Patent: Apr. 8, 2014

(54) METHODS OF CHEMICAL SYNTHESIS OF DIAMINOPHENOTHIAZINIUM COMPOUNDS INVOLVING THE USE OF PERSULFATE OXIDANTS

(75) Inventors: Christopher Paul Larch, Old Aberdeen (GB); John Mervyn David Storey, Old Aberdeen (GB); Craig Williamson, Old Aberdeen (GB); Colin Marshall, Old Aberdeen (GB); Steven John Kemp, Old Aberdeen (GB)

(73) Assignee: Wista Laboratories Ltd., Singapore (SG)

( * ) Notice: Subject to any disclaimer, the term of this patent is extended or adjusted under 35 U.S.C. 154(b) by 186 days.

(21) Appl. No.: 13/318,907

(22) PCT Filed: May 11, 2010

(86) PCT No.: PCT/GB2010/000927  
§ 371 (c)(1),  
(2), (4) Date: Nov. 4, 2011

(87) PCT Pub. No.: WO2010/130977  
PCT Pub. Date: Nov. 18, 2010

(65) Prior Publication Data  
US 2012/0058995 A1 Mar. 8, 2012

Related U.S. Application Data

(60) Provisional application No. 61/177,446, filed on May 12, 2009.

(51) Int. Cl.  
*C07D 279/18* (2006.01)  
*A61K 31/5415* (2006.01)

(52) U.S. Cl.  
USPC .......................................... 544/37; 514/224.8

(58) Field of Classification Search  
USPC ........................................................ 544/37  
See application file for complete search history.

(56) References Cited

FOREIGN PATENT DOCUMENTS

WO  WO 2006/032879 A2  3/2006

OTHER PUBLICATIONS

The International Search Report and Written Opinion received in the corresponding International Patent Application No. PCT/GB2010/000927, dated Sep. 28, 2010.

*Primary Examiner* — Kahsay Habte

(57) ABSTRACT

Described are methods of synthesizing and purifying certain 3,7-diamino-phenothiazin-5-ium compounds (referred to herein as "diaminophenothiazinium compounds") including Methylhioninium Chloride (MTC) (also known as Methylene Blue). In one embodiment, the method comprises the steps of, in order: a thiosulfonic acid formation (TSAF); an oxidative coupling (OC); and a ring closure (RC). Also described are resulting compounds and compositions comprising them (e.g., tablets, capsules) for use in methods of medical treatment and diagnosis, etc., for example, for tauopathies, or Alzheimer's disease (AD).

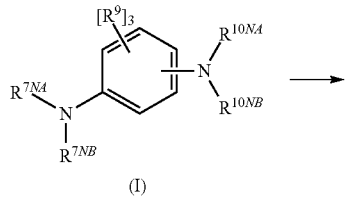

(I)

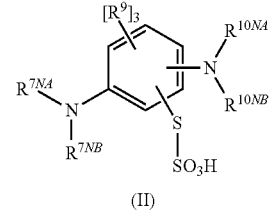

(II)

41 Claims, No Drawings

METHODS OF CHEMICAL SYNTHESIS OF DIAMINOPHENOTHIAZINIUM COMPOUNDS INVOLVING THE USE OF PERSULFATE OXIDANTS

CROSS-REFERENCE TO RELATED PATENT APPLICATIONS

This application is the U.S. National Phase of PCT/GB2010/000927, filed May 11, 2010, and which claims priority from U.S. Provisional Application No. 61/177,446, filed May 12, 2009, all of which are incorporated herein by reference in entirety.

TECHNICAL FIELD

This invention pertains generally to the field of chemical synthesis and purification, and more specifically to methods of synthesizing and purifying certain 3,7-diamino-phenothiazin-5-ium compounds (referred to herein as "diaminophenothiazinium compounds") including Methylthioninium Chloride (MTC) (also known as Methylene Blue). The present invention also pertains to the resulting compounds, and compositions comprising them (e.g., tablets, capsules). Such compounds and compositions find use in methods of inactivating pathogens, and methods of medical treatment and diagnosis, etc., for example, for tauopathies, Alzheimer's disease (AD), skin cancer, melanoma, viral diseases, bacterial diseases and protozoal diseases.

BACKGROUND

Throughout this specification, including any claims which follow, unless the context requires otherwise, the word "comprise," and variations such as "comprises" and "comprising," will be understood to imply the inclusion of a stated integer or step or group of integers or steps, but not the exclusion of any other integer or step or group of integers or steps.

It must be noted that, as used in the specification and any appended claims, the singular forms "a," "an," and "the" include plural referents unless the context clearly dictates otherwise. Thus, for example, reference to "a pharmaceutical carrier" includes mixtures of two or more such carriers, and the like.

Ranges are often expressed herein as from "about" one particular value, and/or to "about" another particular value. When such a range is expressed, another embodiment includes from the one particular value and/or to the other particular value. Similarly, when values are expressed as approximations, by the use of the antecedent "about," it will be understood that the particular value forms another embodiment.

Methylthioninium Chloride (MTC) (also known as Methylene Blue)

Methylthioninium Chloride (MTC) (also known as Methylene blue (MB); methylthionine chloride; tetramethyithionine chloride; 3,7-bis(dimethylamino) phenothiazin-5-ium chloride; C.I. Basic Blue 9; tetramethylthionine chloride; 3,7-bis(dimethylamino) phenazathionium chloride; Swiss blue; C.I. 52015; C.I. Solvent Blue 8; aniline violet; and Urolene Blue® is a low molecular weight (319.86), water soluble, tricyclic organic compound of the following formula:

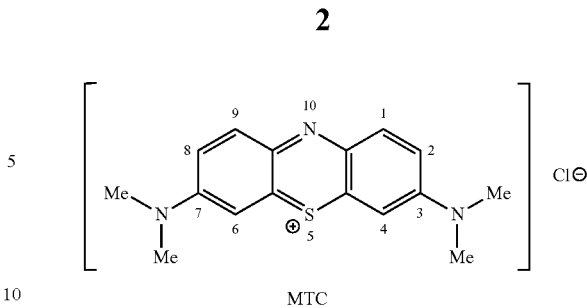

MTC

Methylthioninium Chloride (MTC), perhaps the most well known phenothiazine dye and redox indicator, has also been used as an optical probe of biophysical systems, as an intercalator in nanoporous materials, as a redox mediator, and in photoelectrochomic imaging.

See, for example, Colour Index (Vol. 4, 3rd edition, 1971) and Lillie et al., 1979, and references cited therein.

MTC was first described in a German Patent in 1877 (Badische Anilin- and Soda-Fabrik, 1877). In that patent, MTC was synthesized by nitrosylation of dimethylaniline, subsequent reduction to form N,N-dimethyl-1,4-diaminobenzene, and subsequent oxidative coupling in the presence of hydrogen sulphide ($H_2S$) and iron(III) chloride ($FeCl_3$).

Bernthsen described subsequent studies of MTC and methods for its synthesis (see Bernthsen, 1885a, 1885b, 1889).

Fierz-David and Blangley, 1949, also describes methods for the synthesis of MTC from dimethylaniline, as illustrated in the following scheme:

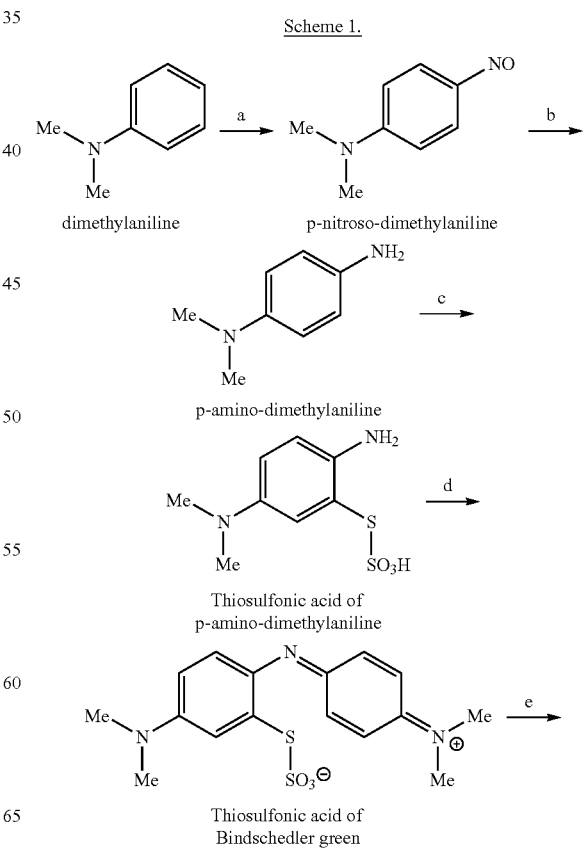

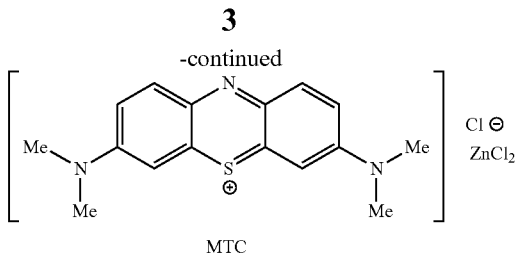

MTC

In step (a), nitrosodimethylaniline is prepared from dimethylaniline by treatment with nitrite ($NaNO_2$) in aqueous acid (HCl) solution. In step (b), the nitroso compound is reduced to form p-aminodimethylaniline in aqueous acid (HCl) solution using zinc dust. In steps (c), (d), and (e), the p-aminodimethylaniline is oxidized in aqueous acid solution with another molecule of dimethylaniline, and simultaneously a thiosulfonic acid group is introduced; the ring is then closed using manganese dioxide or copper sulfate. More specifically, a clear neutral solution of p-aminodimethylaniline is acidified ($H_2SO_4$), and a non-reducing zinc chloride solution is added ($ZnCl_2$ with $Na_2Cr_2O_7$). Aluminium thiosulfate ($Al_2(S_2O_3)_3$) and sodium thiosulfate ($Na_2S_2O_3$) are added. Sodium dichromate ($Na_2Cr_2O_7$) is added. The mixture is heated and aerated. Dimethylaniline is added. Sodium dichromate ($Na_2Cr_2O_7$) is added. The mixture is heated, and becomes dark greenish-blue in colour due to the formation of the thiosulfonic acid of Bindschedler green. Manganese dioxide or copper sulfate is added, and the mixture heated, and the dye precipitates from the concentrated zinc chloride solution.

Very similar synthesis methods are described in the Colour Index (Vol. 4, 3rd edition, 1971), p. 4470.

Masuya et al., 1992, describe certain phenothiazine derivatives, and methods for their preparation and use in photodynamic therapy of cancer and in immunoassays utilizing chemiluminescence. The compounds are prepared by routes similar to those discussed above.

Leventis et al., 1997, describe methods for the synthesis of certain MTC analogs, which employ phenothiazine as a starting material and which add the desired 3,7-substituents by halogenation followed by amination. The authors assert that MTC is synthesized commercially by oxidation of N,N-dimethyl-p-phenylene diamine with $Na_2Cr_2O_7$ in the presence of $Na_2S_2O_3$, followed by further oxidation in the presence of N,N-dimethylamine.

Marshall and Lewis, 1975a, describes the purification of commercial MTC and Azure B by solvent extraction and crystallisation. They assert that aqueous MTC/Azure B mixtures at a buffered pH of 9.5 can be separated by extraction with carbon tetrachloride. The carbon tetrachloride removes the Azure B while leaving the MTC in the aqueous layer. They further assert that low temperature crystallisation of MTC at a concentration of 0.25 N with hydrochloric acid removes metal contaminants. However, the organic purity analysis reported therein is based on thin-layer chromatography, which is not suitable for quantification. Also, the microanalysis for sulphated ash does not indicate a metal free sample. (The preferred technique in 1975 was atomic absorption.)

Marshall and Lewis, 1975b, describes the analysis of metal contaminants in commercial thiazine dyes by atomic absorption spectrophotometry. They report 38 samples with metal concentrations that vary widely between 0.02% and 25.35% of individual samples; the metals examined were iron, potassium, sodium and zinc. They also report that other metals may be present which were not analysed. Aluminium, chromium, manganese, and copper, are all involved in synthetic procedures for MTC and are almost certain to be present. Importantly, they report large variations in the metal content of commercial samples of MTC.

Lohr et al., 1975, describes the purification of Azure B by column chromatography, specifically by separation to isolate the desired product followed by ion exchange back to the chloride. They assert that other cationic dyes such as MTC can be purified by this method. However, column chromatography is not a suitable method for the purification of MTC on a large scale.

Fierz-David et al., 1949, describes the synthesis of the zinc chloride double salt of MTC and the removal of zinc by chelation with sodium carbonate followed by filtration to generate zinc free methylene blue. However, the authors acknowledge that this technique cannot be used on a large scale, because the yields are poor.

WO 2006/032879 describes the synthesis of MTC, and other diaminophenothiazinium compounds, by a number of methods, including an adaptation of the Fierz-David and Blangley procedure described above. The methods described provide diaminophenothiazinium products having reduced levels of metals and contaminating organics.

In particular, WO 2006/032879 addresses the issue of residual Cr levels in a diaminophenothiazinium synthesis by reducing residual Cr(VI) to Cr(III), which is a much less toxic form, so that pharmaceutical standards can more easily be satisfied. This reduction was also found to greatly increase the yield of the final diaminophenothiazinium compound. Experimentally, it was also established that chromium can more easily be removed from a product when in the form of Cr(III) than when in the form of Cr(VI).

MTC and derivatives thereof (e.g., "diaminophenothiazinium compounds") have been found to be useful in the treatment of tauopathies (such as, for example, Alzheimer's disease) (see, for example, Wischik, C. M., et al., 1996, 2002).

Oral and parenteral formulations of MTC are commercially available in the United States, usually under the name Urolene Blue®. However, these formulations contain substantial amounts of metal impurities. These impurities are highly undesirable, and many (e.g., including Al, Cr, Fe, Cu) exceed the safety limits set by European health agencies.

Consequently, there is a great need for higher purity (e.g., pharmaceutical grade purity, e.g., a purity safe for human consumption, e.g., with low or reduced metal content) diaminophenothiazinium compounds, including MTC.

SUMMARY OF THE INVENTION

One aspect of the present invention pertains to a method of synthesis of diaminophenothiazinium compounds, including high purity diaminophenothiazinium compounds.

Another aspect of the present invention pertains to a method of purification of diaminophenothiazinium compounds.

Further aspects of the invention pertain to methods for the synthesis of intermediate compounds which are suitable for use in the synthesis of diaminophenothiazinium compounds.

Another aspect of the present invention pertains to diaminophenothiazinium compounds obtained or obtainable by the methods of the invention for use in therapy.

As will be appreciated by one of skill in the art, features and preferred embodiments of one aspect of the invention will also pertain to other aspects of the invention.

DETAILED DESCRIPTION

Compounds

In general, the present invention pertains to methods for the preparation of certain diamino-phenothiazin-5-ium compounds of the following formula, collectively referred to herein as "diaminophenothiazinium compounds":

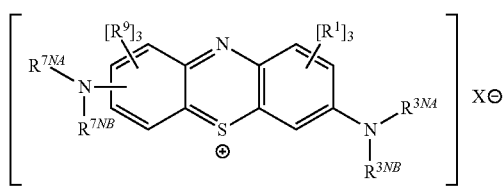

wherein:

each of —$R^1$ and —$R^9$ is independently —H or —$R^A$;

and each —$R^A$ is independently selected from $C_{1-4}$alkyl; $C_{2-4}$alkenyl; halogenated $C_{1-4}$alkyl; $C_{5-10}$aryl; halogenated $C_{5-10}$aryl; $C_{1-4}$alkylene-$C_5$-$C_{10}$aryl and halogenated $C_{1-4}$alkylene-$C_{5-10}$aryl;

each of —$R^{3NA}$ and —$R^{3NB}$ is independently selected from: $C_{1-4}$alkyl; $C_{2-4}$alkenyl; halogenated $C_{1-4}$alkyl; $C_{5-10}$aryl; halogenated $C_{5-10}$aryl; $C_{1-4}$alkylene-$C_{5-10}$aryl and halogenated $C_{1-4}$alkylene-$C_{5-10}$aryl;

each of —$R^{7NA}$ and —$R^{7NB}$ is independently selected from: $C_{1-4}$alkyl; $C_{2-4}$alkenyl; halogenated $C_{1-4}$alkyl; $C_{5-10}$aryl; halogenated $C_{5-10}$aryl; $C_{1-4}$alkylene-$C_{5-10}$aryl and halogenated $C_{1-4}$alkylene-$C_{5-10}$aryl; and $X^-$ is an anionic counter ion.

Although the diaminophenothiazinium compounds are themselves salts, they may also be provided in the form of a mixed salt (i.e, the diaminophenothiazinium compound in combination with another salt). Such mixed salts are intended to be encompassed by the term "and pharmaceutically acceptable salts thereof". Unless otherwise specified, a reference to a particular compound also includes salts thereof.

The diaminophenothiazinium compound is also referred to as compound VI, and in certain embodiments, where $X^-$ is $Cl^-$, compound VII.

In one embodiment, the present invention pertains to methods for the preparation of certain 3,7-diamino-phenothiazin-5-ium compounds of the following formula:

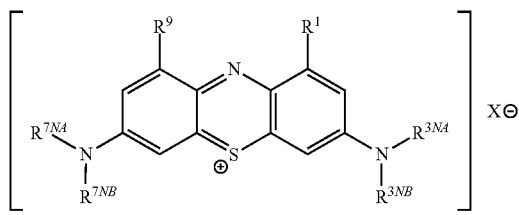

The above structure is only one of many equivalent resonance structures, some of which are shown below, and all of which are intended to be encompassed by the above structure:

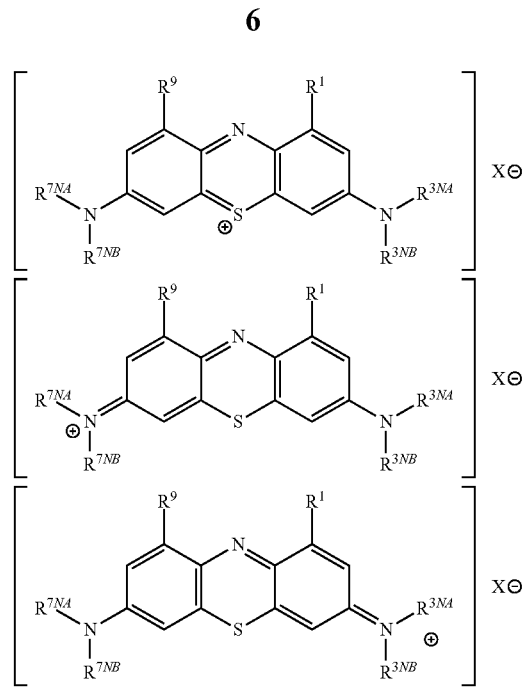

In one aspect, the present invention pertains to methods for the preparation of compounds of the following formula, collectively referred to herein as "activated thio ether compounds" or "diaminoaryl sulphides":

G-II

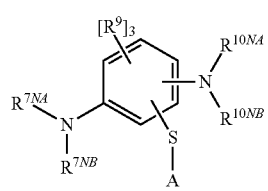

wherein A is an activating group and each of —$R^{10NA}$ and —$R^{10NB}$ is independently selected from: —H; $C_{1-4}$alkyl; $C_{2-4}$alkenyl; halogenated $C_{1-4}$alkyl; $C_{5-10}$aryl; halogenated $C_{5-10}$aryl; $C_{1-4}$alkylene-$C_{5-10}$aryl and halogenated $C_{1-4}$alkylene-$C_{5-10}$aryl. The groups —$R^9$, —$R^{7NA}$ and —$R^{7NB}$ are as defined for the diaminophenothiazinium compounds.

In one embodiment, the present invention pertains to methods for the preparation of compounds of the following formula, collectively referred to herein as "thiosulfonic acid compounds":

II

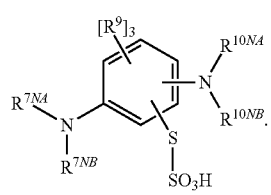

In one aspect, the present invention pertains to methods for the preparation of compounds of the following formula, collectively referred to herein as "activated imino compounds":

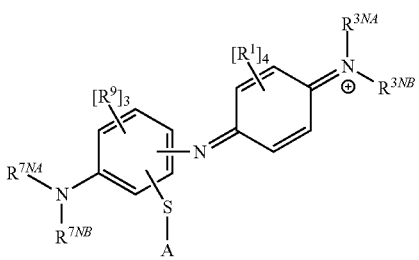

G-IV wherein —R¹, —R⁹, —R³ᴺᴬ and —R³ᴺᴮ, —R⁷ᴺᴬ and —R⁷ᴺᴮ are as defined for the diaminophenothiazinium compounds, and -A is as defined for the activated thio ether compounds (diaminoaryl sulphides). The compound G-IV is shown as a cation, which may be used as a salt with a suitable counter ion, X. Compound G-IV may also be used in a zwitterionic form where a negative charge is associated with the group -A.

In one embodiment, the present invention pertains to methods for the preparation of compounds of the following formula, collectively referred to herein as "imino compounds":

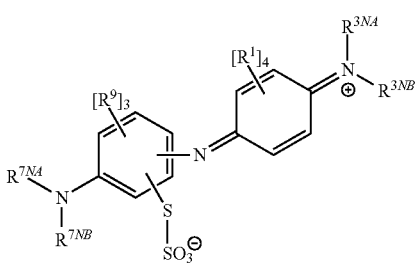

IV

Embodiments

The following embodiments may apply to each of the compounds described herein, as appropriate.

Alkyl and Alkenyl Groups

In one embodiment, the $C_{1-4}$alkyl groups are selected from: linear $C_{1-4}$alkyl groups, such as -Me, -Et, -nPr, -iPr, and -nBu; branched $C_{3-4}$alkyl groups, such as -iPr, -iBu, -sBu, and -tBu; and cyclic $C_{3-4}$alkyl groups, such as -cPr and -cBu.

In one embodiment, the $C_{2-4}$alkenyl groups are selected from linear $C_{1-4}$alkenyl groups, such as —CH=CH₂ (vinyl) and —CH₂—CH=CH₂ (allyl).

In one embodiment, the halogenated $C_{1-4}$alkyl groups are selected from: —CF₃, —CH₂CF₃, and —CF₂CF₃.

Aryl and Alkylenearyl Groups

In one embodiment, the $C_{5-10}$aryl groups are selected from $C_{6-10}$carboaryl groups, such as phenyl or napthyl, and $C_{5-10}$heteroaryl groups, such as thienyl, imidazolyl, pyrazolyl, triazolyl, oxazolyl, isoxazolyl, thiazolyl, isothiazolyl, pyridyl, pyrimidinyl or quinolinyl.

In one embodiment, the halogenated $C_{5-10}$aryl groups are selected from halogenated $C_{6-10}$carboaryl groups, such as -4-fluoro-phenyl, -3-fluoro-phenyl, and -2-fluoro-phenyl, and halogenated $C_{5-10}$heteroaryl groups.

In one embodiment, the $C_{1-4}$alkylene-$C_{5-10}$aryl group is benzyl.

In one embodiment, the halogenated $C_{1-4}$alkylene-$C_{5-10}$aryl groups are selected from halogenated $C_{1-4}$alkylene-$C_{6-10}$carboaryl groups, such as -4-fluoro-benzyl, -3-fluoro-benzyl, and -2-fluoro-benzyl, and halogenated $C_{1-4}$alkylene-$C_{5-10}$heteroaryl groups.

—R¹ and —R⁹

In one embodiment, each of —R¹ and —R⁹ is independently —H or —Rᴬ.

In one embodiment, each —R¹ is independently —H.

In one embodiment, each —R⁹ is independently —H.

In one embodiment, at least one —R¹ is independently —Rᴬ.

In one embodiment, at least one —R⁹ is independently —Rᴬ.

In one embodiment, —R¹ and —R⁹, where present, are the same.

In one embodiment, —R¹ and —R⁹, where present, are different.

In one embodiment, only one —R⁹ is other than —H.

In one embodiment, only one —R¹ is other than —H.

—Rᴬ

In one embodiment, each —Rᴬ, where present, is independently selected from $C_{1-4}$alkyl; $C_{2-4}$alkenyl; halogenated $C_{1-4}$alkyl; $C_{5-10}$aryl; halogenated $C_{5-10}$aryl; $C_{1-4}$alkylene-$C_{5-10}$aryl and halogenated $C_{1-4}$alkylene-$C_{5-10}$aryl;

In one embodiment, each —Rᴬ, where present, is independently selected from $C_{1-4}$alkyl; $C_{2-4}$alkenyl; and halogenated $C_{1-4}$alkyl.

In one embodiment, each —Rᴬ, where present, is independently -Me, -Et, or —CF₃.

In one embodiment, each —Rᴬ, where present, is independently $C_{1-4}$alkyl.

In one embodiment, each —Rᴬ, where present, is independently -Me.

In one embodiment, each —Rᴬ, where present, is independently -Et.

In one embodiment, each —Rᴬ, where present, is independently $C_{2-4}$alkenyl.

In one embodiment, each —Rᴬ, where present, is independently halogenated $C_{1-4}$alkyl.

In one embodiment, each —Rᴬ, where present, is independently —CF₃.

In one embodiment, each —Rᴬ, where present, is independently $C_{5-10}$aryl.

In one embodiment, each —Rᴬ, where present, is independently $C_{5-10}$carboaryl.

In one embodiment, each —Rᴬ, where present, is independently phenyl.

In one embodiment, each —Rᴬ, where present, is independently $C_{1-4}$alkylene-$C_{5-10}$aryl.

In one embodiment, each —Rᴬ, where present, is independently benzyl.

In one embodiment, each —Rᴬ, where present, is independently halogenated $C_{5-10}$aryl.

In one embodiment, each —Rᴬ, where present, is independently halogenated $C_{6-10}$carboaryl.

In one embodiment, each —Rᴬ, where present, is independently -4-fluoro-phenyl, -3-fluoro-phenyl or -2-fluoro-phenyl.

—R³ᴺᴬ, —R³ᴺᴮ, —R⁷ᴺᴬ, and —R⁷ᴺᴮ

In one embodiment, each of —R³ᴺᴬ and —R³ᴺᴮ is independently selected from: $C_{1-4}$alkyl; $C_{2-4}$alkenyl; halogenated $C_{1-4}$alkyl; $C_{5-10}$aryl; halogenated $C_{3-10}$aryl; $C_{1-4}$alkylene-$C_{5-10}$aryl and halogenated $C_{1-4}$alkylene-$C_{5-10}$aryl.

In one embodiment, each of —$R^{3NA}$ and —$R^{3NB}$ is independently selected from: $C_{1-4}$alkyl;

$C_{2-4}$alkenyl; and halogenated $C_{1-4}$alkyl.

In one embodiment, each of —$R^{3NA}$ and —$R^{3NB}$ is independently -Me, -Et, -nPr, -nBu, —$CH_2$—CH=$CH_2$, or —$CF_3$.

In one embodiment, each of —$R^{3NA}$ and —$R^{3NB}$ is independently $C_{1-4}$alkyl.

In one embodiment, each of —$R^{3NA}$ and —$R^{3NB}$ is independently -Me or -Et.

In one embodiment, each of —$R^{3NA}$ and —$R^{3NB}$ is independently -Me.

In one embodiment, each of —$R^{3NA}$ and —$R^{3NB}$ is independently -Et.

In one embodiment, —$R^{3NA}$ and —$R^{3NB}$ are the same.

In one embodiment, —$R^{3NA}$ and —$R^{3NB}$ are different.

In one embodiment, each of —$R^{7NA}$ and —$R^{7NB}$ is independently selected from $C_{1-4}$alkyl; $C_{2-4}$alkenyl; halogenated $C_{1-4}$alkyl; $C_{5-10}$aryl; halogenated $C_{5-10}$aryl; $C_{1-4}$alkylene-$C_{5-10}$aryl and halogenated $C_{1-4}$alkylene-$C_{5-10}$aryl.

In one embodiment, each of —$R^{7NA}$ and —$R^{7NB}$ is independently selected from $C_{1-4}$alkyl;

$C_{2-4}$alkenyl; and halogenated $C_{1-4}$alkyl.

In one embodiment, each of —$R^{7NA}$ and —$R^{7NB}$ is independently -Me, -Et, -nPr, -nBu, —$CH_2$—CH=$CH_2$, or —$CF_3$.

In one embodiment, each of —$R^{7NA}$ and —$R^{7NB}$ is independently $C_{1-4}$alkyl.

In one embodiment, each of —$R^{7NA}$ and —$R^{7NB}$ is independently -Me or -Et.

In one embodiment, each of —$R^{7NA}$ and —$R^{7NB}$ is independently -Me.

In one embodiment, each of —$R^{7NA}$ and —$R^{7NB}$ is independently -Et.

In one embodiment, —$R^{7NA}$ and —$R^{7NB}$ are the same.

In one embodiment, —$R^{7NA}$ and —$R^{7NB}$ are different.

In one embodiment, —$R^{3NA}$ and —$R^{7NB}$, where present, are the same.

In one embodiment, —$R^{3NB}$ and —$R^{7NB}$, where present, are the same.

In one embodiment, the groups —$N(R^{3NA})(R^{3NB})$ and —$N(R^{7NA})(R^{7NB})$, where present, are the same.

In one embodiment, the groups —$N(R^{3NA})(R^{3NB})$ and —$N(R^{7NA})(R^{7NB})$, where present, are the same, and are selected from: —$NMe_2$, —$NEt_2$, —$N(nPr)_2$, —$N(Bu)_2$, —NMeEt, —NMe(nPr), and —$N(CH_2CH=CFl_2)_2$.

In one embodiment, the groups —$N(R^{3NA})(R^{3NB})$ and —$N(R^{7NA})(R^{7NB})$, where present, are the same, and are selected from: —$NMe_2$ and —$NEt_2$.)

In one embodiment, the groups —$N(R^{3NA})(R^{3NB})$ and —$N(R^{7NA})(R^{7NB})$, where present, are each —$NMe_2$.

In one embodiment, the groups —$N(R^{3NA})(R^{3NB})$ and —$N(R^{7NA})(R^{7NB})$, where present, are each —$NEt_2$.

In one embodiment, the groups —$N(R^{3NA})(R^{3NB})$ and —$N(R^{7NA})(R^{7NB})$, where present, are other than —$NMe_2$.

$R^{10NA}$ and —$R^{10NB}$

In one embodiment, each of —$R^{10NA}$ and —$R^{10NB}$ is independently selected from: —H;

$C_{1-4}$alkyl; $C_{2-4}$alkenyl; halogenated $C_{1-4}$alkyl; $C_{3-10}$aryl; halogenated $C_{5-10}$aryl;

$C_{1-4}$alkylene-$C_{5-10}$aryl and halogenated $C_{1-4}$alkylene-$C_{3-10}$aryl.

In one embodiment, each of —$R^{3NA}$ and —$R^{3NB}$ is independently selected from: —H;

—$C_{1-4}$alkyl; $C_{2-4}$alkenyl; and halogenated $C_{1-4}$alkyl.

In one embodiment, each of —$R^{10NA}$ and —$R^{10NB}$ is independently —H.

In one embodiment, each of —$R^{10NA}$ and —$R^{10NB}$ is independently selected from:

$C_{1-4}$alkyl; $C_{2-4}$alkenyl; and halogenated $C_{1-4}$alkyl.

In one embodiment, each of —$R^{10NA}$ and —$R^{10NB}$ is independently -Me, -Et, -nPr, -nBu, $CH_2$—CH=$CH_2$, or —$CF_3$.

In one embodiment, each of —$R^{10NA}$ and —$R^{10NB}$ is independently $C_{1-4}$alkyl.

In one embodiment, each of —$R^{10NA}$ and —$R^{10NB}$ is independently -Me or -Et.

In one embodiment, each of —$R^{10NA}$ and —$R^{10NB}$ is independently -Me,

In one embodiment, each of —$R^{10NA}$ and —$R^{10NB}$ is independently -Et.

In one embodiment, —$R^{10NA}$ and —$R^{10NB}$ are the same.

In one embodiment, —$R^{10NA}$ and —$R^{10NB}$ are different.

-A

In one embodiment, -A is an activating group. In one embodiment, the activating group -A activates the sulfur atom of the thio ether (diaminoaryl sulphide) for ring closure, such as a ring closure reaction described herein.

In one embodiment, -A is independently selected from:
—S(=O)OH, —S(=O)$_2$OH,
—S(=O)$OR^A$, —S(=O)$_2OR^A$,
—S(=O)$_2R^A$,
—S(=O)$_2NH_2$, —S(=O)$_2NHR^A$, —S(=O)$_2NR^A{}_2$,
—S(=O)$_2NR^{A2}R^{A3}$,
—Se(=O)OH, —Se(=O)$_2$OH,
—Se(=O)$OR^A$, —Se(=O)$_2OR^A$,
—Se(=O)$_2R^A$,
—Se(=O)$_2NH_2$, —Se(=O)$_2NHR^A$, —Se(=O)$_2NR^A{}_2$,
—Se(=O)$_2NR^{A2}R^{A3}$,
—P(=O)(OH)$_2$,
—P(=O)(OH)$_2$, —P(=O)(OH)($OR^A$), —P(=O)($OR^A$)$_2$,
—Si($R^A$)$_3$, and
—B($R^A$)$_2$,
where —$R^A$ is as defined previously, and each —$NR^{A2}R^{A3}$, if present, is independently azetidino, pyrrolidino, imidazolidino, pyrazolidino, piperidino, piperazino, morpholino, azepino, or diazepino.

In one embodiment, the group -A includes the ionic forms of the groups above, where appropriate. For example, —S(=O)$_2$OH encompasses the anionic form —S(=O)$_2O^-$.

In one embodiment, -A is independently selected from:
—S(=O)OH, —S(=O)$_2$OH,
—S(=O)$OR^A$, —S(=O)$_2$ORA,
—S(=O)$_2R^A$,
—S(=O)$_2NH_2$, —S(=O)$_2NFIR^A$, —S(=O)$_2NR^A{}_2$,
—S(=O)$_2NR^{A2}R^{A3}$,
—Se(=O)OH, —Se(=O)$_2$OH,
—Se(=O)$OR^A$, —Se(=O)$_2OR^A$,
—Se(=O)$_2R^A$,
—Se(=O)$_2NH_2$, —Se(=O)$_2NHR^A$, —Se(=O)$_2NR^A{}_2$,
—Se(=O)$_2NR^{A2}R^{A3}$.

In one embodiment, -A is independently selected from:
—S(=O)OH, —S(=O)$_2$OH,
—S(=O)$OR^A$, —S(=O)$_2OR^A$,
—S(=O)$_2R^A$,
—Se(=O)OH, —Se(=O)$_2$OH,
—Se(=O)$OR^A$, —Se(=O)$_2OR^A$,
—Se(=O)$_2R^A$.

In one embodiment, -A is independently selected from:
—S(=O)OH, —S(=O)$_2$OH,
—S(=O)$OR^A$, —S(=O)$_2OR^A$,
—S(=O)$_2R^A$.

In one embodiment, -A is independently selected from —S(=O)$_2$OH, —S(=O)$_2$OR$^A$, and —S(=O)$_2$R$^A$.

In one embodiment, -A is independently —S(=O)$_2$OH (also written as —SO$_3$H or sulfonic acid). In this embodiment the activated S-ether is a thiosulfonic acid (—SSO$_3$H).

Isotopes

In one embodiment, one or more of the carbon atoms is $^{11}$C or $^{13}$C.

In one embodiment, one or more of the carbon atoms is $^{11}$C.

In one embodiment, one or more of the carbon atoms is $^{13}$C.

In one embodiment, one or more of the nitrogen atoms is $^{15}$N.

In one embodiment, one or more or all of the carbon atoms of one or more or all of the groups R$^{3NA}$, R$^{3NB}$, R$^{7NA}$ and R$^{7NB}$ is $^{13}$C.

In one embodiment, each of the groups —N(R$^{3NA}$)(R$^{3NB}$) and —N(R$^{7NA}$)(R$^{7NB}$), where present, is —N($^{13}$CH$_3$)$_2$.

In one embodiment, each of R$^1$ and R$^9$, where present, is —H, and each of the groups —N(R$^{3NA}$)(R$^{3NB}$) and —N(R$^{7NA}$)(R$^{7NB}$), where present, is —N($^{13}$CH$_3$)$_2$.

In one embodiment, each of R$^1$ and R$^9$, where present, is —H; each of the groups —N(R$^{3NA}$)(R$^{3NB}$) and —N(R$^{7NA}$)(R$^{7NB}$), where present, is —N($^{13}$CH$_3$)$_2$; and X$^-$ is Cl$^-$.

X$^-$

In one embodiment, X$^-$ is a counter anion to achieve electrical neutrality.

In one embodiment, X$^-$ is one or more counter anions to achieve electrical neutrality.

In one embodiment, X$^-$ is a counter anion shared with other cations to achieve electrical neutrality.

In one embodiment, X$^-$ is independently a halogen anion (i.e., halide).

In one embodiment, X$^-$ is independently F$^-$, Cl$^-$, Br$^-$, or I$^-$.

In one embodiment, X$^-$ is independently Cl$^-$, Br$^-$, or I$^-$.

In one embodiment, X$^-$ is independently Cl$^-$.

In one embodiment, X$^-$ is independently NO$_3^-$ (nitrate).

In one embodiment, X$^-$ is independently ClO$_3^-$ (perchlorate).

In one embodiment, X$^-$ is independently selected from formate, propionate, benzoate and 4-hydroxybenzenesulfonate.

In one embodiment, X$^-$ is independently S$_2$O$_8^-$.

In one embodiment, X$^-$ is S$_2$O$_3^{-2}$.

In one embodiment, X$^-$ is SO$_4^{-2}$ (sulfate).

In one embodiment, X$^-$ is succinate.

In this embodiment, the counter ion achieves electrical neutrality by combination with two of the recited cations.

In one embodiment, X$^-$ is citrate. In this embodiment, the counter ion achieves electrical neutrality by combination with three of the recited cations.

In one embodiment, the compound is in the form of a mixed salt, for example, a ZnCl$_2$ mixed salt.

Combinations

Each and every compatible combination of the embodiments described above, and below, is explicitly disclosed herein, as if each and every combination was individually and explicitly recited.

Example Compounds

Example diaminophenothiazinium compounds include the following:

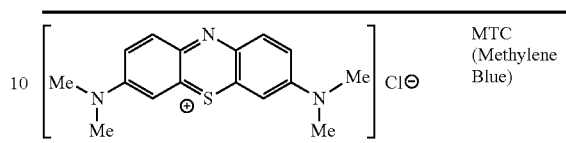
MTC (Methylene Blue)

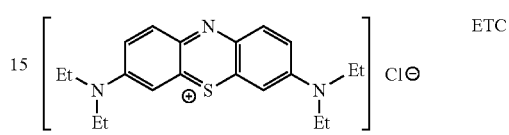
ETC

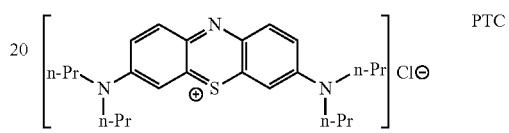
PTC

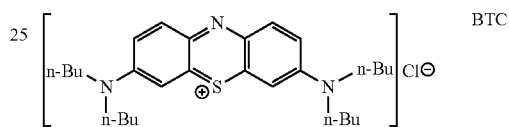
BTC

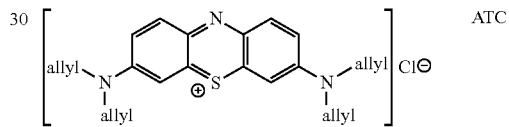
ATC

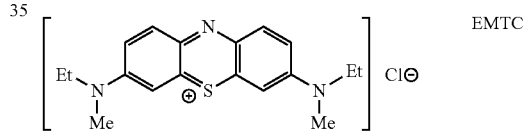
EMTC

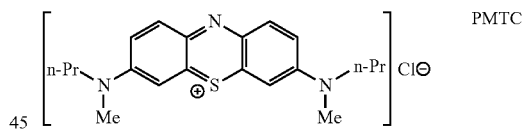
PMTC

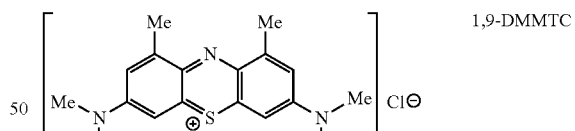
1,9-DMMTC

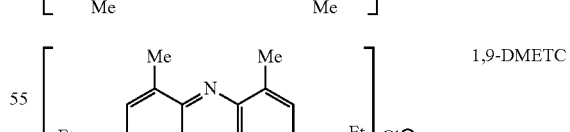
1,9-DMETC

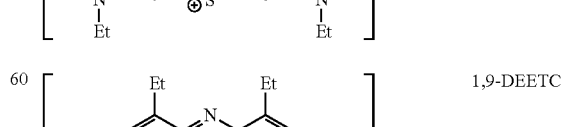
1,9-DEETC

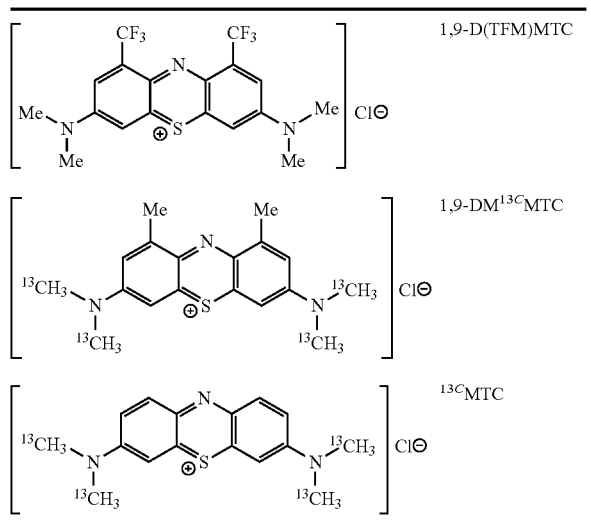

Example thiosulfonic acid compounds include the following:

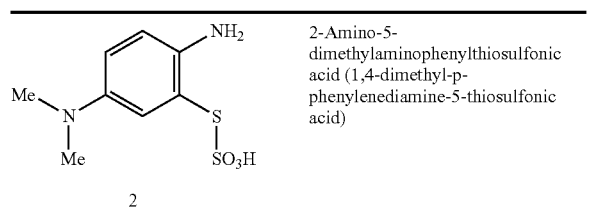

Example imino compounds include the following:

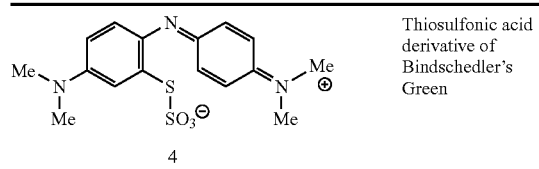

Synthesis

One important difference between known methods and the presently claimed methods is the minimisation or avoidance of a dichromate salt as an oxidising agent in the synthesis. In one aspect, the present method avoids the use of a dichromate salt in the oxidative coupling step of a diaminophenothiazinium synthesis, such as those steps described by Fierz-David and Blangley and WO 2006/032879, amongst others.

In another aspect, the present method avoids the use of a dichromate salt in the thiosulfonic acid forming step of a diaminophenothiazinium synthesis, such as those steps described by Fierz-David and Blangley and WO 2006/032879, amongst others.

In one embodiment, the present invention provides a method of preparing MTC that minimises the amount of dichromate salt required in the overall synthesis. In one embodiment, the present invention provides a method of preparing MTC that does not require a dichromate salt.

Sodium dichromate, the preferred dichromate salt in the Fierz-David and Blangley and WO 2006/032879 syntheses, is registered under the International Maritime Dangerous Goods (IMDG) Code under Class 6.1: Toxic substances. Sodium dichromate is expensive to purchase and ship, and its disposal is likewise costly. Owing to the toxicity and carcinogenicity of sodium dichromate, specialist safety precautions are required to be put in place for its large scale use. The chromium-containing by-products from a chromate oxidation are likewise highly hazardous and must be dealt with appropriately.

Accordingly, the use of sodium dichromate on an industrial scale is impractical, and the diaminophenothiazinium syntheses described previously in the art would therefore not be amenable to large scale production.

The present inventors have established that an alternative range of oxidants may be used in a diaminophenothiazinium synthesis. In particular, the inventors have established that a persulfate salt may be used as an oxidant in a diaminophenothiazinium synthesis.

Previously, dichromate (in the form Cr(VI)) has been described for use (at least) in the oxidative coupling step of the diaminophenothiazinium synthesis. Residual Cr(VI) presents several serious problems. First, high levels of highly toxic contaminants such as residual Cr(VI) are unacceptable in products destined for use in pharmacy. Second, residual Cr(VI) destabilizes the zwitterionic intermediate and impedes the subsequent ring closure (RC) step, and thus reduces the yield of the final diaminophenothiazinium compound.

As indicated above, WO 2006/032879 addresses the issue of residual Cr levels in a diaminophenothiazinium synthesis. However, the solution is to reduce residual Cr(VI) to Cr(III), which can more easily be removed from a product compared to Cr(VI). There is no suggestion or indication that chromium should not be used in a diaminophenothiazinium synthesis.

In one embodiment, a reference herein to a TSAF step is also a reference to an activated thio ether (diaminoaryl sulphide) formation step, as described herein. In one embodiment, a reference herein to a Cr-TSAF step is also a reference to a Cr-mediated activated thio ether (diaminoaryl sulphide) formation step, as described herein.

In one embodiment, the method of synthesis comprises an oxidative coupling (OC).

In one embodiment, the method of synthesis comprises a thiosulfonic acid formation (TSAF).

In one embodiment, the method of synthesis comprises, in order, an oxidative coupling (OC) and a ring closure (RC).

In one embodiment, the method of synthesis comprises, in order:
  a thiosulfonic acid formation (TSAF);
  an oxidative coupling (OC); and
  a ring closure (RC).

In one embodiment, the method of synthesis comprises, in order:
  a nitrosyl reduction (NR);
  a thiosulfonic acid formation (TSAF);
  an oxidative coupling (OC); and
  a ring closure (RC).

In one embodiment, the method of synthesis comprises, in order:
  a nitrosylation (NOS);
  a nitrosyl reduction (NR);
  a thiosulfonic acid formation (TSAF);
  an oxidative coupling (OC); and
  a ring closure (RC).

In one embodiment, the method of synthesis comprises, in order:
an N,N-disubstitution (NNDS);
a nitrosylation (NOS);
a nitrosyl reduction (NR);
a thiosulfonic acid formation (TSAF);
an oxidative coupling (OC); and
a ring closure (RC).

In one embodiment, the method of synthesis comprises, in order:
a Cr-mediated thiosulfonic acid formation (Cr-TSAF);
an oxidative coupling (OC); and
a ring closure (RC).

In one embodiment, the method of synthesis comprises, in order:
a nitrosyl reduction (NR);
a Cr-mediated thiosulfonic acid formation (Cr-TSAF);
an oxidative coupling (OC); and
a ring closure (RC).

In one embodiment, the method of synthesis comprises, in order:
a nitrosylation (NOS);
a nitrosyl reduction (NR);
a Cr-mediated thiosulfonic acid formation (Cr-TSAF);
an oxidative coupling (OC); and
a ring closure (RC).

In one embodiment, the method of synthesis comprises, in order:
an N,N-disubstitution (NNDS);
a nitrosylation (NOS);
a nitrosyl reduction (NR);
a Cr-mediated thiosulfonic acid formation (Cr-TSAF);
an oxidative coupling (OC); and
a ring closure (RC).

In one embodiment, the method of synthesis comprises, in order:
a thiosulfonic acid formation (TSAF);
a Cr-mediated oxidative coupling (Cr—OC); and
a ring closure (RC).

In one embodiment, the method of synthesis comprises, in order:
a nitrosyl reduction (NR);
a thiosulfonic acid formation (TSAF);
a Cr-mediated oxidative coupling (Cr—OC); and
a ring closure (RC).

In one embodiment, the method of synthesis comprises, in order:
a nitrosylation (NOS);
a nitrosyl reduction (NR);
a thiosulfonic acid formation (TSAF);
a Cr-mediated oxidative coupling (Cr—OC); and
a ring closure (RC).

In one embodiment, the method of synthesis comprises, in order:
an N,N-disubstitution (NNDS);
a nitrosylation (NOS);
a nitrosyl reduction (NR);
a thiosulfonic acid formation (TSAF);
a Cr-mediated oxidative coupling (Cr—OC); and
a ring closure (RC).

In one embodiment, the method of synthesis further includes the step of chloride salt formation (CSF) after a ring closure (RC) step. Such a step may not be required where the product of the RC step is a chloride salt.

General Methods

The methods of the invention generally include at least one activated thio ether (diaminoaryl sulphide) activation step, which may be a thiosulfonic acid formation (TSAF) step, or at least one oxidative coupling (OC) step, as described below. In one embodiment, the method comprises both steps.

Activated Thio Ether (Diaminowyl Sulphide) Formation and Thiosulfonic Acid Formation (TSAF)

In this step, an N,N-disubstituted-diamino-substituted benzene, I, is oxidized in the presence of an oxidizing agent that is or comprises persulfate to give an activated S—(N,N-disubstituted-diamino-phenyl) ether (a S-activated diaminoaryl sulphide), G-II, as illustrated in the following scheme:

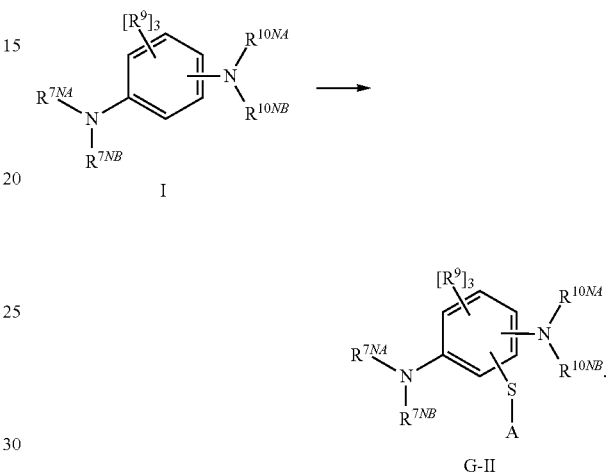

This reaction may be referred to as an activated thio ether (S-activated diaminoaryl sulphide) formation step.

Compound I is oxidised in the presence of an activating group reagent. In one embodiment, the activating group reagent is or comprises $[S-A]^{n-}$ or $[S-A]$, where n is 1 or 2. For example, the activating group reagent is or may comprise the anion $[S-SO_3]^{2-}$ (thiosulfate).

In one embodiment, n is 1. In one embodiment, n is 2.

In one embodiment, the activating group reagent additionally comprises a counter cation.

In one embodiment, the counter cation is a sodium, potassium, or ammonium cation.

In one embodiment, the counter cation is a sodium cation.

In one embodiment, the activating group reagent is or comprises thiosulfate.

In one embodiment, an N,N-disubstituted-diamino-substituted benzene, I, is oxidized in the presence of a thiosulfate and an oxidizing agent that is or comprises persulfate to give an amino-(N,N-disubstituted-amino)phenylthiosulfonic acid (a thiosulfonic acid S—(N,N-disubstituted-diamino-phenyl) ester)), II, as illustrated in the following scheme:

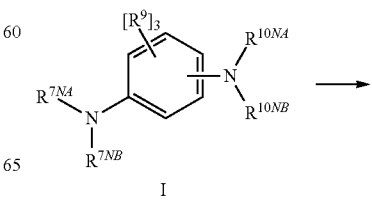

-continued

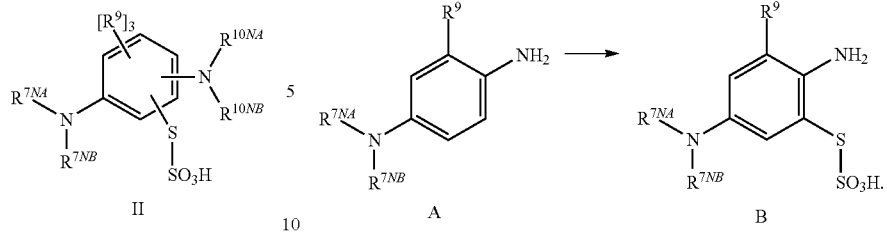

II

This activated thio ether (S-activated diaminoaryl sulphide) formation reaction may be referred to as a thiosulfonic acid formation (TSAF) step.

The phenyl ring in compound I is substituted with an amino group, $-NR^{10NA}R^{10NB}$, at any one of the 2-, 3-, 4-, 5-, or 6-positions, and is substituted with three substituents $-R^9$, at any three of the four remaining positions. The final position is substituted with $-H$.

The phenyl ring in compound II is substituted with an amino group, $-NR^{10NA}R^{10NB}$, at any of the 2-, 3-, 4-, 5-, or 6-positions, and is substituted with three substituents $-R^9$, at any three of the four remaining positions. The final position is substituted with thiosulfonic acid, $-S-SO_3H$.

In one embodiment, compounds I and II are compounds of formula Ia and IIa respectively as shown below:

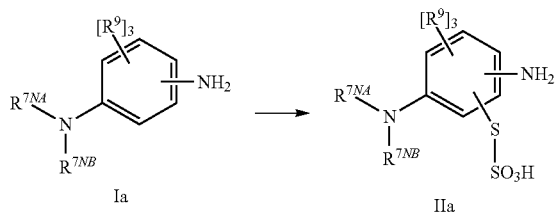

Ia       IIa

In one embodiment, compounds I and II are compounds of formula Ib and IIb respectively as shown below:

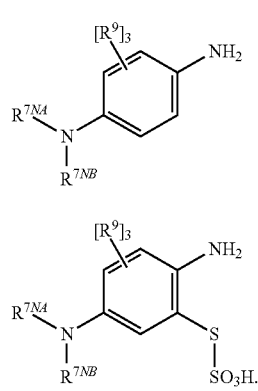

Ib

IIb

In one embodiment, an N,N-disubstituted-1,4-diamino-5-optionally substituted benzene, A, is oxidized in the presence of a thiosulfate to give a thiosulfonic acid S-{2-(amino)-3-(optionally substituted)-5-(N,N-disubstituted-amino)-phenyl}ester (an (amino-(N,N-disubstituted)aminophenylthiosulfonic acid), B, as illustrated in the following scheme:

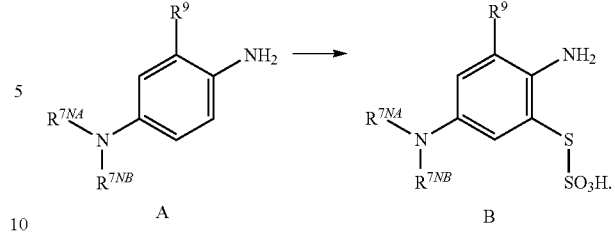

A       B

In one embodiment, an N,N-dimethyl-1,4-diamino-benzene, 1, is oxidized in the presence of a thiosulfate to give a thiosulfonic acid S-{2-(amino)-5-(dimethylamino)-phenyl}ester (an amino-(N,N-disubstituted-amino)phenylthiosulfonic acid), 2, as illustrated in the following scheme:

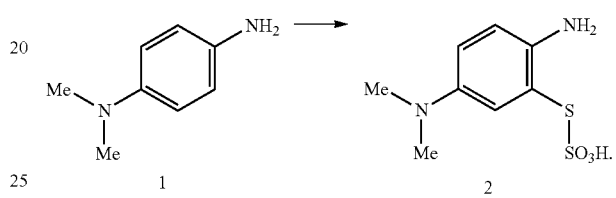

1       2

Compound 1 may be obtained from commercial sources, or may be prepared directly or indirectly from the corresponding nitrosyl compound, as described below in the NOS and DNNDS steps.

The thiosulfate is or comprises $S_2O_3^{-2}$.

In one embodiment, the thiosulfate is or comprises $Na_2S_2O_3$.

In one embodiment, the thiosulfate is or comprises $Na_2S_2O_3$ or a hydrate thereof.

$Na_2S_2O_3$ may be obtained commercially, for example, as the anhydrous salt or as the pentahydrate.

In one embodiment, the molar ratio of thiosulfate to diamine, I, is 0.8 to 1.5.

In one embodiment, the molar ratio is 0.8 to 1.3.

In one embodiment, the molar ratio is about 1.0

In one embodiment, the oxidizing agent is or comprises persulfate.

In one embodiment, the persulfate is or comprises $S_2O_8^{2-}$.

In one embodiment, the persulfate is or comprises sodium persulfate, potassium persulfate, or ammonium persulfate.

In one embodiment, the persulfate is or comprises sodium persulfate.

In one embodiment, the persulfate is sodium persulfate, or a hydrate thereof.

In one embodiment, the molar ratio of persulfate to diamine, I, is 0.5 to 1.5.

In one embodiment, the range is 0.8 to 1.3.

In one embodiment, the range is about 1.0.

In one embodiment, the amine, I, is added first, before the activating group reagent is added.

In one embodiment, the activating group reagent is added before the persulfate is added.

In one embodiment, the amine, I, is added first, before the thiosulfate is added.

In one embodiment, the thiosulfate is added before the persulfate is added.

In one embodiment, the reaction is performed in an aqueous medium.

In one embodiment, the pH of the aqueous medium is adjusted after the amine, I, is added.

In one embodiment, the pH of the aqueous medium is adjusted after the amine, I, is added, and before the thiosulfate is added.

In one embodiment, the pH of the aqueous medium is adjusted after the amine, I, is added, and before the thiosulfate and the persulfate are added.

In one embodiment, the pH of the aqueous medium is adjusted to a pH of 2 to 7.

In one embodiment, the pH of the aqueous medium is adjusted to a pH of 3 to 5.

In one embodiment, the pH of the aqueous medium is adjusted to a pH of about 4.

In one embodiment, the acidic conditions are adjusted using a strong acid.

In one embodiment, the acidic conditions are adjusted using HCl.

In one embodiment, the acidic conditions are adjusted using a strong base.

In one embodiment, the acidic conditions are adjusted using a hydroxide base.

In one embodiment, the hydroxide base is, or comprises, sodium hydroxide, potassium hydroxide, or lithium hydroxide.

In one embodiment, the reaction is performed in an aqueous medium comprising an organic solvent.

In one embodiment, the organic solvent is present at about 1 to 50% v/v.

In one embodiment, the organic solvent is present at about 5 to 40% v/v.

In one embodiment, the organic solvent is present at about 20% v/v.

In one embodiment, the organic solvent is miscible with water.

In one embodiment, the organic solvent is THF, DMF, acetonitrile or saturated aliphatic $C_{1-5}$alkyl alcohol.

In one embodiment, the organic solvent is THF, acetonitrile or saturated aliphatic
$C_{1-6}$alkyl alcohol.

In one embodiment, the saturated aliphatic $C_{1-6}$alkyl alcohol is methanol.

In one embodiment, the reaction is performed in an aqueous medium comprising a surfactant.

In one embodiment, the surfactant is an anionic surfactant.

In one embodiment, the anionic surfactant is a sulfonic acid surfactant.

In one embodiment, the anionic surfactant is a dodecylbenzenesulfonic acid salt.

In one embodiment, the anionic surfactant is an alkyl sulfate salt.

In one embodiment, the anionic surfactant is selected from alkyl benzene sulfonate, sodium laureth sulfate, sodium dodecyl sulfate (SDS), ammonium lauryl sulfate, perfluorooctanesulfonate (PFOS) and perfluorooctanoate (PFOA or PFO).

In one embodiment, the surfactant is a cationic surfactant.

In one embodiment, the cationic surfactant is selected from benzethonium chloride (BZT), benzalkonium chloride (BAC), polyethoxylated tallow amine (POEA), cetylpyridinium chloride (CPC) and cetyl trimethylammonium bromide.

In one embodiment, the surfactant is a nonionic surfactant.

In one embodiment, the nonionic surfactant is a polysorbate.

In one embodiment, the nonionic surfactant is a fatty alcohol.

In one embodiment, the nonionic surfactant is selected from dodecyl dimethylamine oxide, Tween 20, Tween 80, cetyl alcohol, coleyl alcohol, decyl maltoside, octyl glucoside, cocamide MEA, cocamide DEA, alkylphenol poly(ethylene oxide) and alkyl poly(ethylene oxide).

In one embodiment, the surfactant is a zwitterionic surfactant.

In one embodiment, the zwitterionic surfactant is selected from coco ampho glycinate, dodecyl betaine and cocamidopropyl betaine.

In one embodiment, the reaction is performed under acidic conditions.

In one embodiment, the reaction is performed at a pH of less than 7.

In one embodiment, the reaction is performed at a pH of 3 to 5.

In one embodiment, the reaction is performed at a pH of about 4.

In one embodiment, the thiosulfate is added in one portion.

In one embodiment, the persulfate is added in one portion.

In one embodiment, the persulfate is added portionwise.

In one embodiment, the reaction temperature is 2 to 25° C.

In one embodiment, the reaction temperature is 2 to 15° C.

In one embodiment, the reaction temperature is 2 to 10° C.

In one embodiment, the reaction temperature is about 5° C.

In one embodiment, the reaction time is 10 to 240 minutes.

In one embodiment, the reaction time is 30 to 120 minutes.

In one embodiment, the reaction time is about 60 minutes.

In one embodiment, the reaction mixture is stirred during the reaction step.

In one embodiment, the isolation and purification is by filtration.

In one embodiment, the S-activated diaminoaryl sulphide G-II is isolated and purified.

In one embodiment, the isolation and purification is by filtration followed by washing.

In one embodiment, the isolation and purification is by filtration followed by drying.

In one embodiment, the drying is air-drying.

In one embodiment, the drying is air-drying for 10 min to 6 hours.

In one embodiment, the drying is air-drying for 10 min to 2 hours.

In one embodiment, the drying is air-drying for about 30 min.

In one embodiment, the drying is air-drying on the filter.

In one embodiment, the drying is oven-drying.

In one embodiment, the drying is oven-drying for 2 to 48 hours.

In one embodiment, the drying is oven-drying for 2 to 24 hours.

In one embodiment, the drying is oven-drying for about 12 hours.

In one embodiment, the drying is oven-drying at 30 to 60° C. for 2 to 24 hours.

In one embodiment, the oven-drying is under vacuum.

In one embodiment, the drying is air-drying followed by oven-drying.

In one embodiment, after reaction, the reaction mixture is filtered and the filtrate collected.

In one embodiment, isolation of the S-activated diaminoaryl sulphide is by filtration.

In one embodiment, the purification comprises re-dissolving in an organic solvent and filtering In one embodiment, the purification comprises re-dissolving in an organic solvent, heating at reflux, cooling and filtering.

In one embodiment, the purification comprises re-dissolving in ethyl acetate, heating at reflux, cooling and then filtering.

In one embodiment the purification comprises re-dissolving in an organic solvent, heating at reflux, filtering and washing with an organic solvent.

In one embodiment heating at reflux is for a period of between 30 minutes and 120 minutes, preferably between 45 and 90 minutes.

In one embodiment heating at reflux for a period of about 1 hour.

Oxidative Coupling (OC)

In this step, a S-activated diaminoaryl sulphide (an activated S-(amino-substituted-(N,N-disubstituted-amino)-phenyl)thio ether), G-IIa, is oxidatively coupled to an N,N-disubstituted-substituted-aniline, III, using an oxidizing agent that is or comprises persulfate, to give a S-activated N-substituted N'-substituted imino aminoaryl sulphide (activated {(thio ether)-(disubstituted amino)-(substituted)-phenylimino}-substituted cyclohexa-2,5-dienylidene-N,N-disubstituted ammonium), G-IV, as illustrated in the following scheme:

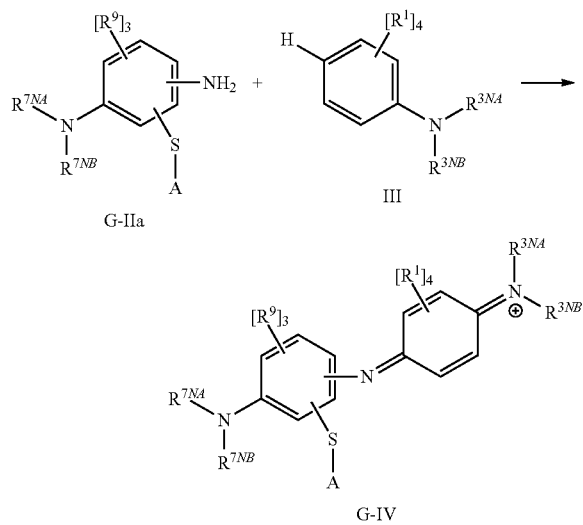

The compound G-IV is shown as a cation, which may be prepared as a salt with a suitable counter ion, X. Compound G-IV may also be prepared as a zwitterionic form where a negative charge is associated with the group -A.

In one embodiment, a thiosulfonic acid S-(amino-substituted-(N,N-disubstituted-amino)-phenyl)ester (an amino-(N,N-disubstituted-amino)phenylthiosulfonic acid), II, is oxidatively coupled to an N,N-disubstituted-substituted-aniline, III, using an oxidizing agent that is or comprises persulfate, to give a {(thiosulfate)-(disubstituted amino)-(substituted)-phenyl-imino}-substituted cyclohexa-2,5-dienylidene-N,N-disubstituted ammonium, IV, as illustrated in the following scheme:

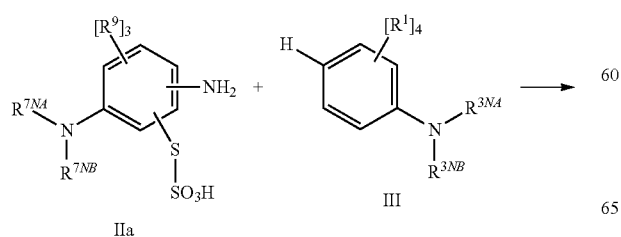

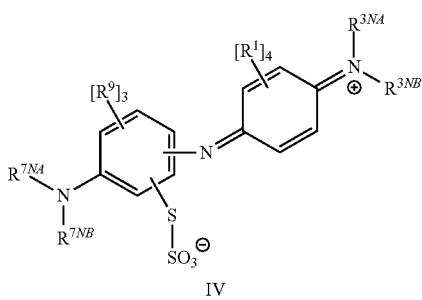

The phenyl ring in compound II is substituted with an amino group, —NH$_2$, at any one of the 2-, 3-, 4-, 5-, or 6-positions, and is substituted with three substituents —R$^9$, at any three of the four remaining positions. The final position is substituted with thiosulfonic acid, —S—SO$_3$H.

The phenyl ring in compound III is substituted with —H at the 4-position, and is substituted with four substituents —R$^1$, at the 2-, 3-, 5-, and 6-positions.

The left-hand phenyl ring in compound IV, as drawn, is substituted with an imino group, —N=, at any one of the 2-, 3-, 4-, 5-, or 6-positions, and is substituted with three substituents —R$^9$, at any three of the four remaining positions. The final position is substituted with thiosulfonic acid, —S—SO$_3$H. The right-hand cyclohexa-2,5-dienylidene ring in compound IV, as drawn, is substituted with an imino group, =N—, at the 4-position, and is substituted with four substituents —R$^1$, at the 2-, 3-, 5-, and 6-positions.

In one embodiment, IIa and IV are compounds IIb and IVa respectively:

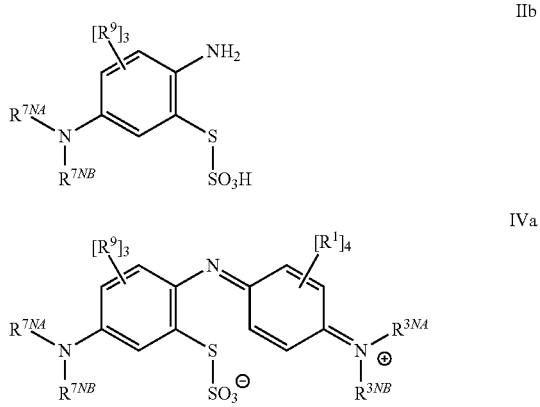

In one embodiment, IIa, III and IV are compounds IIb, IIIa and V respectively:

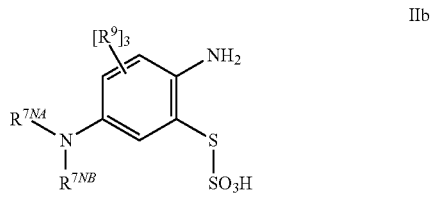

IIIa

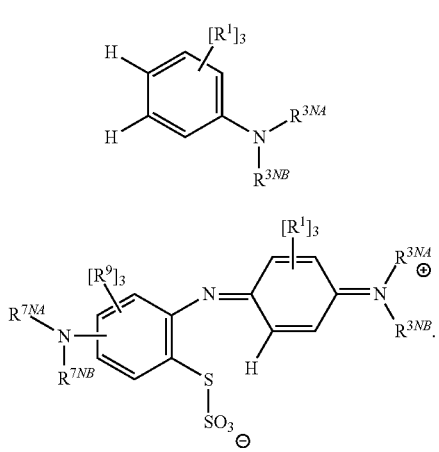

V

In one embodiment, a thiosulfonic acid S-{2-(amino)-3-(optionally substituted)-5-(N,N-disubstituted amino)-phenyl}ester (amino-(N,N-disubstituted-amino)phenylthiosulfonic acid), B, is oxidatively coupled to an N,N-disubstituted-3-optionally substituted-aniline, C, using an oxidizing agent that is or comprises persulfate, to give a [4-{2-(thiosulfate)-4-(N,N-disubstituted amino)-6-(optionally substituted)-phenyl-imino}-3-(optionally substituted)-cyclohexa-2,5-dienylidene]-N,N-disubstituted ammonium, D, as illustrated in the following scheme:

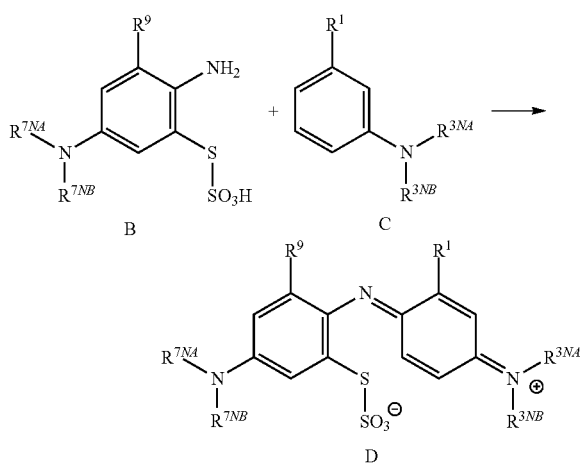

In one embodiment, a thiosulfonic acid S-{2-(amino)-5-(dimethylamino)-phenyl}ester (an amino-(disubstituted-amino)phenylthiosulfonic acid), 2, is oxidatively coupled to an N,N-dimethyl-aniline, 3, using an oxidizing agent that is or comprises persulfate, to give a [4-{2-(thiosulfate)-4-(dimethylamino)-phenyl-imino}-cyclohexa-2,5-dienylidene]-N,N-dimethyl ammonium, 4, as illustrated in the following scheme:

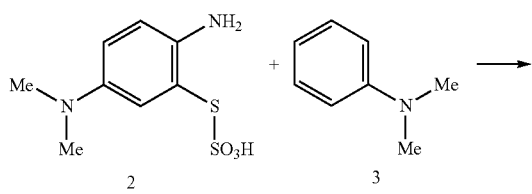

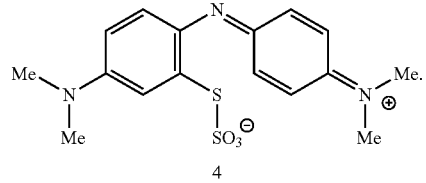

In one embodiment, the S-activated diaminoaryl sulphide, G-IIa, is added first, before the aniline, III, is added.

In one embodiment, the amino-(N,N-disubstituted-amino)phenylthiosulfonic acid, IIa, is added first, before the aniline, III, is added.

In one embodiment, the reaction is performed in an aqueous medium.

In one embodiment, the aniline, III, is added before the persulfate is added.

In one embodiment, the aniline, III, is added in a mixture with aqueous acid.

In one embodiment, the aqueous acid is an aqueous mineral acid.

In one embodiment, the aqueous acid is aqueous $H_2SO_4$.

In one embodiment, the aqueous acid is aqueous HCl.

In one embodiment, the oxidizing agent is or comprises a persulfate.

In one embodiment, the oxidizing agent is or comprises a persulfate salt.

In one embodiment, the oxidizing agent is or comprises sodium persulfate, potassium persulfate, or ammonium persulfate.

In one embodiment, the oxidizing agent is or comprises sodium persulfate.

In one embodiment, the oxidizing agent is sodium persulfate, or a hydrate thereof.

In one embodiment, the molar ratio of S-activated diaminoaryl sulphide, G-IIa, to aniline, III, is 0.5 to 1.5.

In one embodiment, the molar ratio of amino-(N,N-disubstituted-amino)phenylthiosulfonic acid, IIa, to aniline, III, is 0.5 to 1.5.

In one embodiment, the range is 0.8 to 1.2.

In one embodiment, the range is about 1.0.

In one embodiment, the molar ratio of aniline, III, to persulfate, is 0.5 to 2.0.

In one embodiment, the range is 0.8 to 1.5.

In one embodiment, the range is 0.8 to 1.2.

In one embodiment, the range is about 1.0.

In one embodiment, the reaction is performed under basic conditions.

In one embodiment, the basic conditions are obtained after the aniline has been added.

In one embodiment, the reaction is performed at a pH of 7 or more.

In one embodiment, the reaction is performed at a pH of more than 7.

In one embodiment, the reaction is performed at a pH of 7.1 to 10.0.

In one embodiment, the reaction is performed at a pH of 7.1 to 8.0.

In one embodiment, the reaction is performed at a pH of about 7.5.

In one embodiment, the basic conditions are obtained using a strong base.

In one embodiment, the basic conditions are obtained using LiOH, NaOH, KOH, or CsOH.

In one embodiment, the basic conditions are obtained using NaOH.

In one embodiment, the reaction temperature is 2 to 20° C.

In one embodiment, the reaction temperature is 2 to 15° C.

In one embodiment, the reaction temperature is about 5° C.

In one embodiment, the reaction time is 30 minutes to 12 hours.

In one embodiment, the reaction time is 60 minutes to 5 hours.

In one embodiment, the reaction time is 60 minutes to 4 hours.

In one embodiment, the reaction time is about 3 hours.

In one embodiment, the reaction mixture is stirred during the reaction step.

In one embodiment, aniline, III, is the same as aniline, IX.

In one embodiment, the zwitterionic intermediate G-IV is isolated and purified.

In one embodiment, the isolation and purification is by filtration.

In one embodiment, the isolation and purification is by filtration followed by washing.

In one embodiment, the washing is washing with $H_2O$.

In one embodiment, the washing is washing with $H_2O$ and tetrahydrofuran (THF).

In one embodiment, the isolation and purification is by filtration followed by washing and drying.

In one embodiment, the isolation and purification is by filtration followed by drying.

In one embodiment, the drying is air-drying.

In one embodiment, the drying is air-drying for 2 to 72 hours.

In one embodiment, the drying is air-drying for 2 to 48 hours.

In one embodiment, the drying is air-drying for 2 to 24 hours.

In one embodiment, the drying is air-drying on the filter.

In one embodiment, the drying is oven-drying.

In one embodiment, the drying is oven-drying for 2 to 72 hours.

In one embodiment, the drying is oven-drying for 2 to 48 hours.

In one embodiment, the drying is oven-drying for 2 to 24 hours.

In one embodiment, the drying is oven-drying at 30 to 60° C. for 2 to 48 hours.

In one embodiment, the oven-drying is under vacuum.

In one embodiment, the drying is air-drying followed by oven-drying.

For example, in one embodiment, the reaction mixture is filtered, and the residue (e.g., ~100 mmol crude product) is washed with $H_2O$ (e.g., 4×250 cm$^3$) and THF (e.g., 100 cm$^3$), and then air-dried overnight.

For example, in one embodiment, the reaction mixture is filtered (e.g., through a Buchner filter under vacuum), the solid removed, added to another vessel with fresh water, the mixture stirred vigorously, and filtered again. The "filter-recover-resuspend" process may be repeated a number of times. The finally obtained solid may be used in subsequent steps.

Ring Closure (RC)

In this step, a N,N-disubstituted N'-substituted aminoiminoaryl sulphide (a {(thio ether)-(N,N-disubstituted amino)-(substituted)-phenyl-imino}-substituted cyclohexa-2,5-dienylidene-N,N-disubstituted ammonium), G-V, is subjected to ring closure to give a bis(N,N-disubstituted-amino)-(substituted)-phenothiazin-5-ium salt, VI, as illustrated in the following scheme:

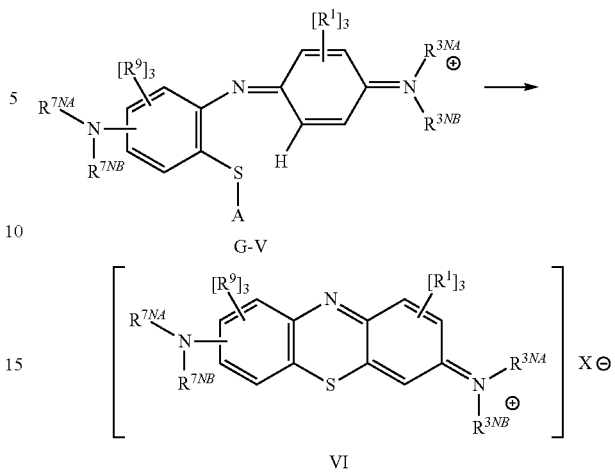

The compound G-V is shown as a cation, which may be used as a salt with a suitable counter ion, X. Compound G-V may also be used in a zwitterionic form where a negative charge is associated with the group -A.

In one embodiment, a {(thiosulfate)-(N,N-disubstituted amino)-(substituted)-phenyl-imino}-substituted cyclohexa-2,5-dienylidene-N,N-disubstituted ammonium, V, is subjected to ring closure to give a bis(N,N-disubstituted-amino)-(substituted)-phenothiazin-5-ium salt, VI, as illustrated in the following scheme:

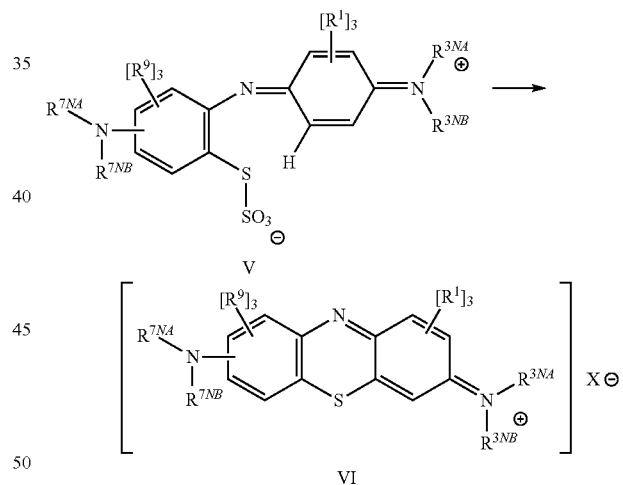

The left-hand phenyl ring in compound V, as drawn, is substituted with thiosulfonic acid, —S—SO$_3^-$, at the 1-position, is substituted with an imino group, =N—, at the 2-position, is substituted with an amino group, —NR$^{7NA}$R$^{7NB}$, at any one of the 3-, 4-, 5-, or 6-positions, and is substituted with three substituents —R$^9$, at the three remaining positions. The right-hand cyclohexa-2,5-dienylidene ring in compound V, as drawn, is substituted with an imino group, =N—, at the 4-position, and is substituted with three substituents —R$^1$, at the 2-, 3-, and 6-positions. The 5-position is substituted with —H, as shown.

The left-hand ring in compound VI, as drawn, is linked to the right-hand ring through a sulphur atom at the 1-position and the N atom at the 2-position. The left-hand ring is substituted with an amino group, —NR$^{7NA}$R$^{7NB}$, at any one of the 3-, 4-, 5-, or 6-positions, and is substituted with three substituents —R⁹, at the three remaining positions. The right-hand ring in compound VI, as drawn, is linked to the left-hand ring through the sulphur atom at the 1-position and the N atom at the 2-position. The right-hand ring is substituted with an amino group, —NR$^{3NA}$R$^{3NB}$, at the 5-position, and is substituted with three substituents —R¹, at the three remaining positions.

In one embodiment, compounds V and VI are compounds of formula Va and VIa respectively:

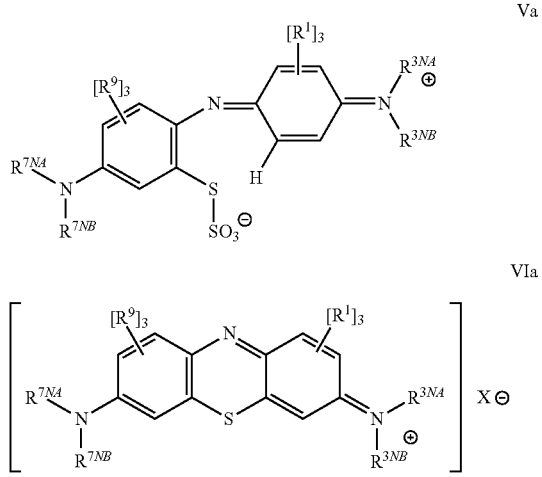

In one embodiment, a [4-{2-(thiosulfate)-4-(N,N-disubstituted amino)-6-(optionally substituted)-phenyl-imino}-3-(optionally substituted)-cyclohexa-2,5-dienylidene]-N,N-disubstituted ammonium, D, is subjected to ring closure to give a 3,7-bis(N,N-disubstituted-amino)-1,9-(optionally substituted)-phenothiazin-5-ium salt, E, as illustrated in the following scheme:

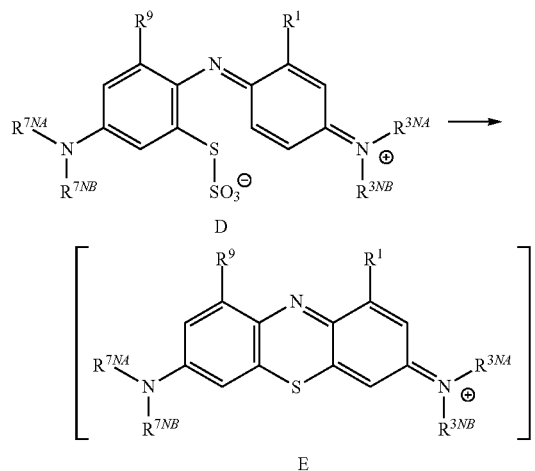

In one embodiment, a [{2-(thiosulfate)-4-(dimethylamino)-phenyl-imino}-cyclohexa-2,5-dienylidene]-N,N-dimethyl ammonium, 4, is subjected to ring closure to give a 3,7-bis(dimethylamino)-phenothiazin-5-ium salt, 5, as illustrated in the following scheme:

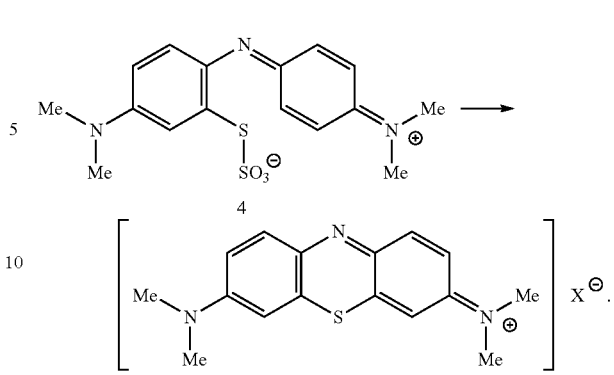

In one embodiment, ring closure is achieved by treatment with an oxidizing agent.

In one embodiment, the reaction is performed at reflux.

In one embodiment, the reaction temperature is 30 to 95° C.

In one embodiment, the reaction temperature is 50 to 90° C.

In one embodiment, the reaction temperature is 60 to 90° C.

In one embodiment, the reaction temperature is about 85° C.

In one embodiment, the reaction time is 10 to 120 minutes.

In one embodiment, the reaction time is 20 to 90 minutes.

In one embodiment, the reaction time is about 60 minutes.

In one embodiment, the reaction is performed in an aqueous medium.

In one embodiment, the reaction is performed until the reaction mixture changes colour, e.g., becomes a deep blue colour.

In one embodiment, the reaction mixture is stirred during the reaction step.

In one embodiment, after reaction, the reaction mixture is filtered and the filtrate collected.

In one embodiment, the reaction mixture is first cooled, and the filtration is performed at about room temperature, to give a "cool" filtrate.

In one embodiment, the filtration is performed at a temperature near to the reaction temperature, to give a "hot" filtrate.

In one embodiment, after reaction, a salt is added to the reaction mixture.

In one embodiment, the salt is an alkali metal salt.

In one embodiment, the salt comprises the counter ion X⁻.

In one embodiment, the product of the reaction is a salt, wherein X⁻ is $S_2O_8^-$.

In one embodiment, the product of the reaction is a salt, wherein X⁻ is 0.5 $S_2O_3^{-2}$.

In one embodiment, the product of the reaction is a salt, wherein X⁻ does not comprise a halogen ion.

In one embodiment, the product of the reaction is a salt, wherein X⁻ does not comprise a chloride ion.

In one embodiment, the product of the reaction is reacted with a chloride salt as a source of chloride to form a product where X⁻ is a chloride ion, as described below in the Chloride Salt Formation (CSF) step.

Cu(II) Oxidising Agent

In one embodiment, the oxidizing agent is or comprises Cu(II).

In one embodiment, the oxidizing agent is or comprises Cu(II) sulfate.

In one embodiment, the oxidizing agent is Cu(II) sulfate or a hydrate thereof.

In one embodiment, the oxidizing agent is or comprises Cu(II).

In one embodiment, ring closure is performed under acidic conditions.

In one embodiment, ring closure is performed at a pH of 1 to 5.

In one embodiment, ring closure is performed at a pH of 2 to 5.

In one embodiment, ring closure is performed at a pH of 3 to 4.5.

In one embodiment, ring closure is performed at a pH of 3.5 to 4.1.

In one embodiment, ring closure is performed at a pH of about 2.0.

In one embodiment, the desired pH is obtained by the addition of strong acid.

In one embodiment, the desired pH is obtained by the addition of HCl.

In one embodiment, the molar ratio of Cu(II) to ammonium, G-V, is 0.02 to 0.2.

In one embodiment, the molar ratio of Cu(II) to ammonium, V, is 0.02 to 0.2.

In one embodiment, the range is 0.05 to 0.15

In one embodiment, the range is about 0.1.

$MnO_2$ Oxidising Agent

In one embodiment, the oxidizing agent is or comprises activated manganese dioxide ($MnO_2$).

In one embodiment, the oxidizing agent is activated manganese dioxide ($MnO_2$).

In one embodiment, the molar ratio of $MnO_2$ to ammonium, G-V, is 1.0 to 3.0.

In one embodiment, the molar ratio of $MnO_2$ to ammonium, V, is 1.0 to 3.0.

In one embodiment, the molar ratio is 1.5 to 2.5.

In one embodiment, the molar ratio is about 2.0.

In one embodiment, after completion of the reaction (a blue solution with precipitate is observed), strong acid (e.g., concentrated $H_2SO_4$) is added.

Without wishing to be bound by any particular theory, it is believed that the strong acid dissolves the manganese salts (and other salts, if present).

Chloride Salt Formation (CSF)

In this step, a bis(N,N-disubstituted-amino)-(substituted)-phenothiazin-5-ium salt, VI, is reacted with chloride, to give a bis(N,N-disubstituted-amino)-(substituted)-phenothiazin-5-ium chloride salt, VII, as illustrated in the following scheme:

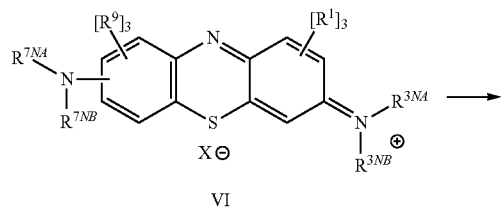

VI

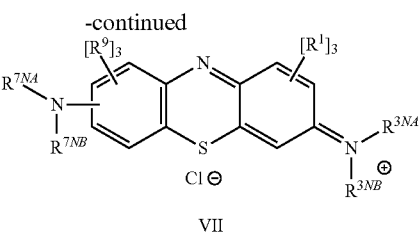

VII

In one embodiment, a 3,7-bis(N,N-disubstituted-amino)-1,9-(optionally substituted)-phenothiazin-5-ium salt, E, is reacted with chloride, to give a 3,7-bis(N,N-disubstituted-amino)-1,9-(optionally substituted)-phenothiazin-5-ium chloride salt, F, as illustrated in the following scheme:

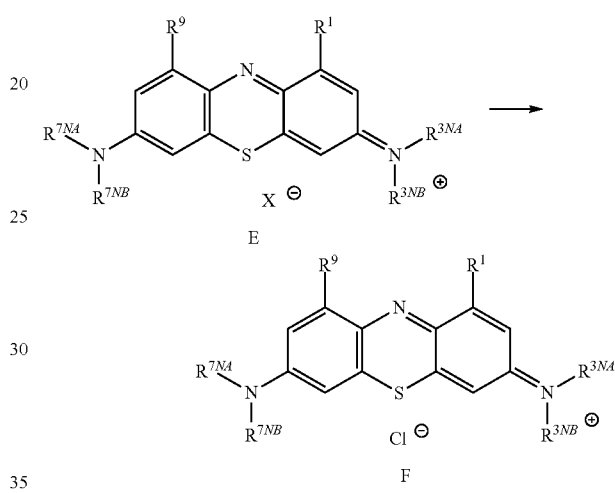

In one embodiment, a 3,7-bis(dimethylamino)-phenothiazin-5-ium salt is reacted with chloride, to give a 3,7-bis(dimethylamino)-phenothiazin-5-ium chloride salt, 5 (i.e., MTC), as illustrated in the following scheme:

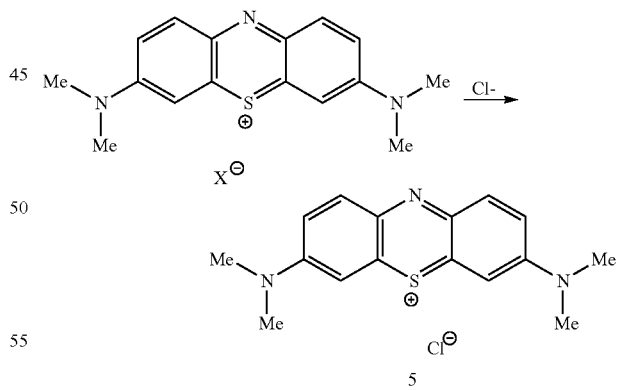

In one embodiment, VI is reacted with a chloride salt as a source of chloride.

In one embodiment, the chloride is chloride salt.

In one embodiment, the chloride is an alkali metal chloride.

In one embodiment, the chloride is sodium chloride.

In one embodiment, there is a large molar excess of (sodium) chloride.

In one embodiment, the molar ratio of chloride to salt, VI, is 5 to 100.

In one embodiment, the molar ratio is 5 to 80.
In one embodiment, the molar ratio is 5 to 50.
In one embodiment, the molar ratio is about 8.
In one embodiment, the reaction is performed in an aqueous medium.
In one embodiment, the reaction temperature is 0 to 95° C.
In one embodiment, the reaction temperature is 0 to 50° C.
In one embodiment, the reaction temperature is 0 to 30° C.
In one embodiment, the reaction temperature is 2 to 30° C.
In one embodiment, the reaction temperature is 2 to 20° C.
In one embodiment, the reaction temperature is about 5° C.
In one embodiment, the reaction time is 10 to 120 minutes.
In one embodiment, the reaction time is about 60 minutes.
In one embodiment, the reaction is performed until the reaction mixture (initially, e.g., a deep blue colour) becomes light blue to colourless.
In one embodiment, the reaction mixture is stirred during the reaction step.
In one embodiment, the reaction mixture is allowed to cool following addition of the chloride to salt VI at the reaction temperature, to yield the product as a precipitate.
In one embodiment, the reaction mixture is allowed to cool to 0 to 30° C.
In one embodiment, the reaction mixture is allowed to cool to 0 to 20° C.
In one embodiment, the reaction mixture is allowed to cool to about 5° C.
In one embodiment, the reaction mixture is filtered hot following addition of the chloride to salt VI at the reaction temperature, and the collected filtrate allowed to cool, to yield the product as a precipitate.
In other embodiments, VI is reacted with hydrochloric acid as a source of chloride.
In other embodiments, the Chloride salt formation is performed according to the methods described in WO 2006/032879, which is incorporated by reference herein. In particular the sections relating to Chloride salt formation (CAF) at pages 32-33 and Chloride salt formation (CSF-2) at pages 58-59 are incorporated herein.
Following the chloride salt formation steps, one or more additional steps may be performed, as discussed at pages 33 and 34, including the sulphide treatment described at pages 34-36, the dimethyldithiocarbamate treatment (DT) at pages 36-37, the carbonate treatment (CT) at pages 37-38, the ethylenediaminetetraacetic acid treatment (EDTAT) at pages 39-40, and the organic extraction (OE) at pages 40-41, which are incorporated herein.

Cr-Mediated Activated Thio Ether (diaminoaryl sulphide) Formation and Thiosulfonic Acid Formation (Cr-TSAF)

In this step, an N,N-disubstituted-diamino-substituted benzene, Ia, is oxidized in the presence of an oxidizing agent that is or comprises Cr(VI) to give an S-(amino-substituted-(N,N-disubstituted-amino)-phenyl)ether, (S-activated N,N-disubstituted diaminoaryl sulphide) G-IIa, as illustrated in the following scheme:

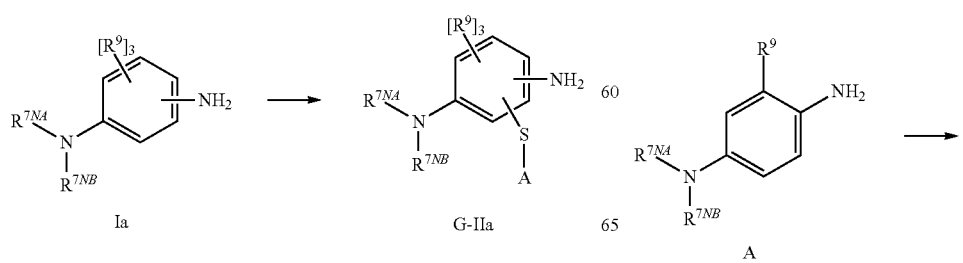

This reaction may be referred to as a Cr-mediated activated thio ether formation step. Compound Ia is oxidised in the presence of an activating group reagent. The activating group reagent and the group -A are as defined for the activated thio ether (S-activated diaminoaryl sulphide) formation step described above.

In one embodiment, the activating group reagent is thiosulfate. In this embodiment, the group A is —S(=O)$_2$OH.

In one embodiment, an N,N-disubstituted-diamino-substituted benzene, Ia, is oxidized in the presence of a thiosulfate and an oxidizing agent that is or comprises Cr(VI) to give a thiosulfonic acid S-(-amino-substituted-(N,N-disubstituted-amino)-phenyl) ester (an amino-(N,N-disubstituted-amino)phenylthiosulfonic acid), IIa, as illustrated in the following scheme:

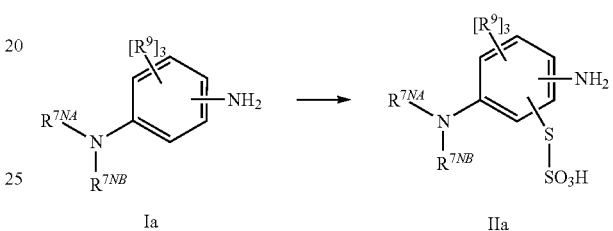

In one embodiment, compounds I and II are compounds of formula Ib and IIb respectively as shown below:

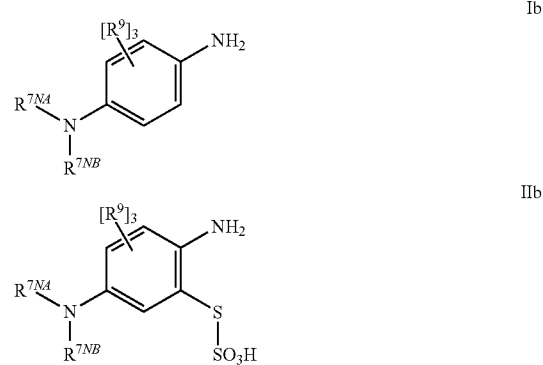

In one embodiment, an N,N-disubstituted-1,4-diamino-5-optionally substituted benzene, A, is oxidized in the presence of a thiosulfate and an oxidizing agent that is or comprises Cr(VI) to give a thiosulfonic acid S-{2-(amino)-3-(optionally substituted)-5-(N,N-disubstituted-amino)-phenyl}ester (an amino-(N,N-disubstituted-amino)phenylthiosulfonic acid), B, as illustrated in the following scheme:

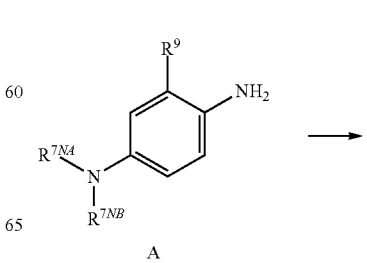

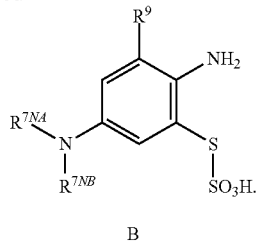

B

In one embodiment, an N,N-dimethyl-1,4-diamino-benzene, 1, is oxidized in the presence of a thiosulfate and an oxidizing agent that is or comprises Cr(VI) to give a thiosulfonic acid S-{2-(amino)-5-(dimethylamino)-phenyl}ester, (a 2-amino-5-dimethyl-aminophenylthiosulfonic acid), 2, as illustrated in the following scheme:

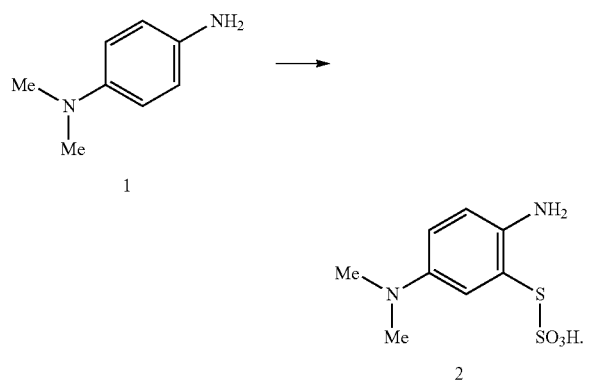

The Cr-mediated thiosulfonic acid formation is performed according to the methods described in WO 2006/032879, which is incorporated by reference herein. In particular the sections relating to Thiosulfonic acid formation (TSAF) at pages 22-23, and Thiosulfonic acid formation (TSAF-3) at pages 54-55 are incorporated herein, along with Examples 1-8 and 17 relating to the synthesis of thiosulfonic acid S-{2-(amino)-5-(dimethylamino)-phenyl}ester, (2-amino-5-(dimethylaminophenylthiosulfonic acid) and Example 20, relating to the synthesis of thiosulfonic acid S-{2-(amino)-3-ethyl-5-(dimethylamino)-phenyl}ester (2-amino-3-methyl-5-dimethylaminophenylthiosulfonic acid).

The thiosulfate is or comprises $S_2O_3^{-2}$.

In one embodiment, the thiosulfate is or comprises $Na_2S_2O_3$.

In one embodiment, the thiosulfate is $Na_2S_2O_3$ or a hydrate thereof.

In one embodiment, the oxidation is by reaction with an oxidizing agent.

In one embodiment, the oxidizing agent is or comprises Cr(VI).

In one embodiment, the oxidizing agent is or comprises $Cr_2O_7^{-2}$.

In one embodiment, the oxidizing agent is or comprises $Na_2Cr_2O_7$.

In one embodiment, the oxidizing agent is $Na_2Cr_2O_7$ or a hydrate thereof.

In one embodiment, the molar ratio of Cr(VI) to diamine, I, is 0.2 to 2.0.

In one embodiment, the reaction is performed in an aqueous medium.

In one embodiment, the reaction temperature is 2 to 25° C.

In one embodiment, the oxidizing agent additionally comprises Al(III).

In one embodiment, the molar ratio of Al(III) to diamine, I, is 0.2 to 2.0.

In one embodiment, the oxidizing agent further comprises a strong acid.

In one embodiment, the molar ratio of acid protons to diamine, I, is 1.0 to 4.0.

Cr-Mediated Oxidative Coupling (Cr—OC)

In this step, an activated S-(amino-substituted-(N,N-disubstituted-amino)-phenyl) thio ether, G-IIa, is oxidatively coupled to an N,N-disubstituted-substituted-aniline, III, using an oxidizing agent that is or comprises Cr(VI), to give a S-activated N,N-disubstituted N'-substituted aminoiminoaryl sulphide (an activated {(thio ether)-(N,N-disubstituted amino)-(substituted)-phenyl-imino}-substituted cyclohexa-2,5-dienylidene-N,N-disubstituted ammonium), G-IV, as illustrated in the following scheme:

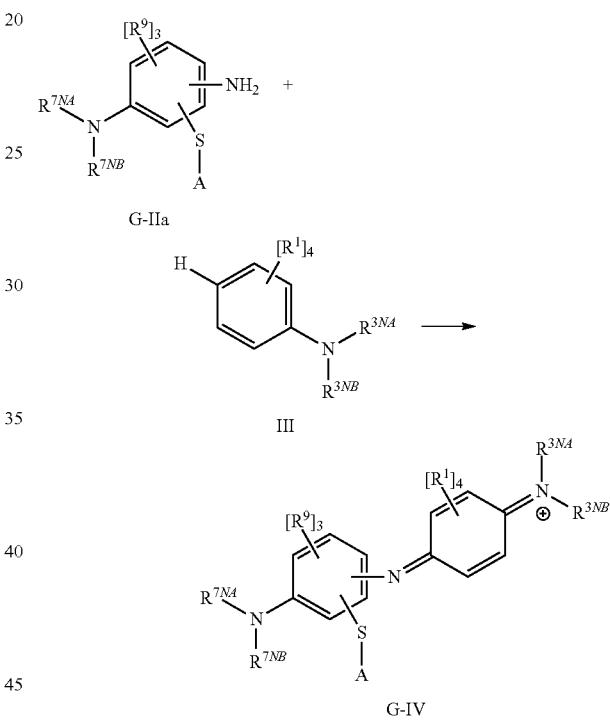

In one embodiment, a thiosulfonic acid S-(amino-substituted-(N,N-disubstituted-amino)-phenyl)ester (an amino-(N,N-disubstituted-amino)phenylthiosulfonic acid), IIa, is oxidatively coupled to an N,N-disubstituted-substituted-aniline, III, using an oxidizing agent that is or comprises Cr(VI), to give a {(thiosulfate)-(N,N-disubstituted amino)-(substituted)-phenyl-imino}-substituted cyclohexa-2,5-dienylidene-N,N-disubstituted ammonium, IV, as illustrated in the following scheme:

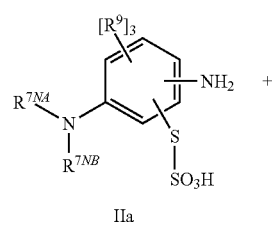

IIa

-continued

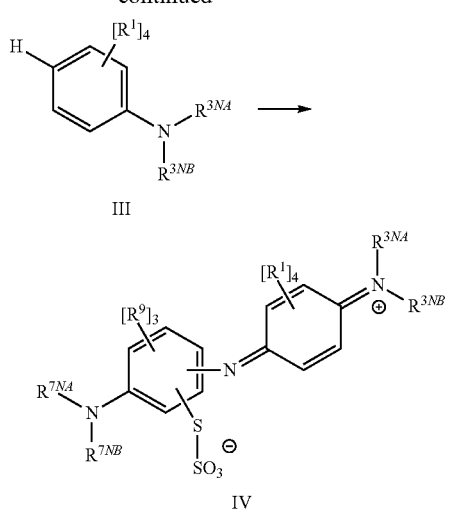
III

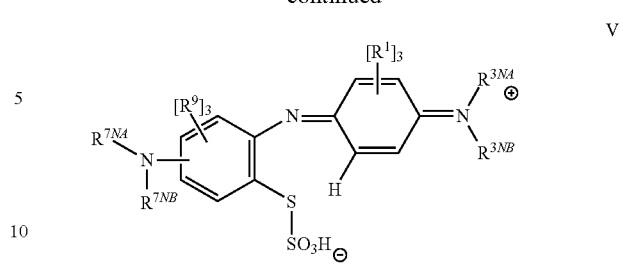
IV

In one embodiment, IIa and IV are compounds IIb and IVa respectively:

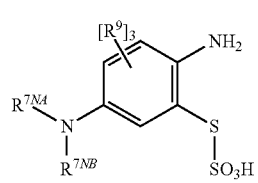
IIb

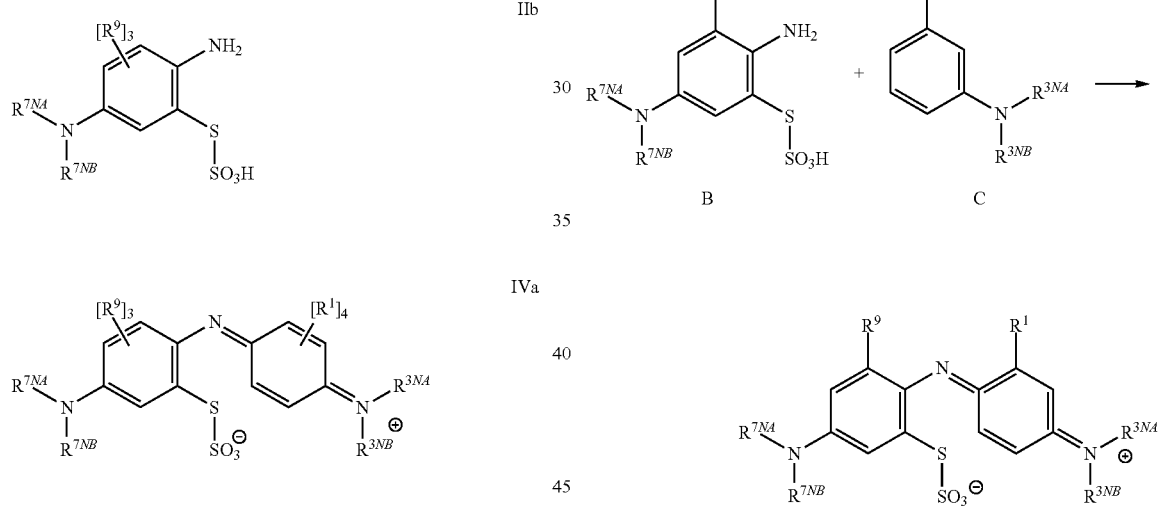

In one embodiment, IIa, III and IV are compounds IIb, IIIa and V respectively:

IIb

IIIa

-continued

V

In one embodiment, a thiosulfonic acid S-{2-(amino)-3-(optionally substituted)-5-(N,N-disubstituted amino)-phenyl}ester (an amino-(N,N-disubstituted-amino)phenylthiosulfonic acid), B, is oxidatively coupled to an N,N-disubstituted-3-optionally substituted-aniline, C, using an oxidizing agent that is or comprises Cr(VI), to give a [4-{2-(thiosulfate)-4-(N,N-disubstituted amino)-6-(optionally substituted)-phenyl-imino}-3-(optionally substituted)-cyclohexa-2,5-dienylidene]-N,N-disubstituted ammonium, D, as illustrated in the following scheme:

B + C →

D

In one embodiment, a thiosulfonic acid S-{2-(amino)-5-(dimethylamino)-phenyl}ester (a 2-amino-5-dimethylaminophenylthiosulfonic acid), 2, is oxidatively coupled to an N,N-dimethyl-aniline, 3, using an oxidizing agent that is or comprises Cr(VI), to give a [4-{2-(thiosulfate)-4-(dimethylamino)-phenyl-imino}-cyclohexa-2,5-dienylidene]-N,N-dimethyl ammonium, 4, as illustrated in the following scheme:

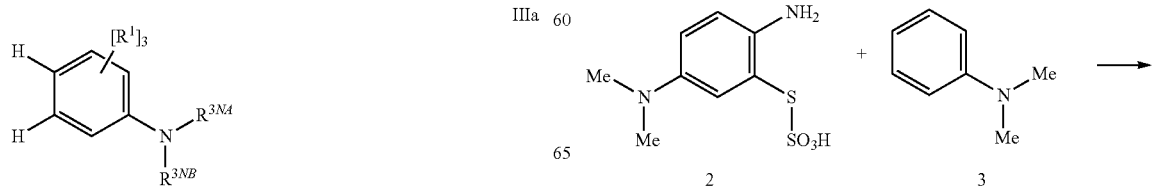
2    3

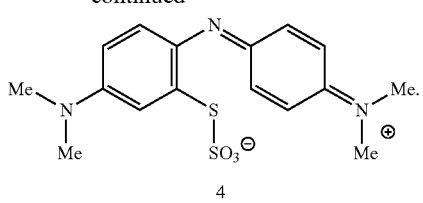

The Cr-mediated oxidative coupling is performed according to the methods described in WO 2006/032879, which is incorporated by reference herein. In particular the sections relating to Oxidative coupling (OC) at pages 23-25 and Oxidative coupling (OC-3) at pages 55-56 are incorporated herein. In addition the use of a Cr oxidising agent as described in Examples 1 to 8, 17 and 20, with or without isolation of the intermediate, is also incorporated herein.

The oxidative coupling may be used in combination with any one of the Cr(VI) reduction (CR) and/or isolation and purification of zwitterinoic intermediate (IAPOZI) steps described in WO 2006/032879. See, in particular, pages 25-30, which are incorporated by reference herein.

In one embodiment, the oxidizing agent is or comprises $Cr_2O_7^{-2}$.

In one embodiment, the oxidizing agent is or comprises $Na_2Cr_2O_7$.

In one embodiment, the oxidizing agent is $Na_2Cr_2O_7$.

In one embodiment, the molar ratio of ester, G-IIa, to aniline, III, is 0.5 to 1.5.

In one embodiment, the molar ratio of ester, IIa, to aniline, III, is 0.5 to 1.5.

In one embodiment, the molar ratio of Cr(VI) to aniline, III, is 1.0 to 4.0.

In one embodiment, the reaction is performed under acidic conditions.

In one embodiment, the reaction is performed in an aqueous medium.

In one embodiment, the reaction temperature is 2 to 20° C.

Nitrosyl Reduction (NR)

In this step, an N,N-disubstituted-substituted-nitrosyl aniline, VIII, is reduced to form an N,N-disubstituted-di-amino-substituted benzene, Ia, as illustrated in the following scheme:

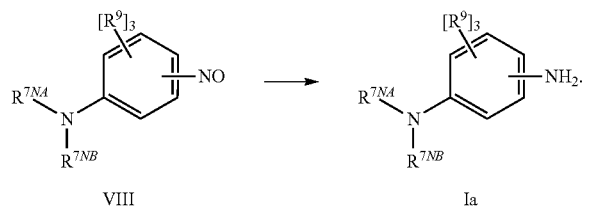

In one embodiment, an N,N-disubstituted-3-optionally substituted-4-nitrosyl aniline, G, is reduced to form a N,N-disubstituted-1,4-diamino-5-optionally substituted benzene, A, as illustrated in the following scheme:

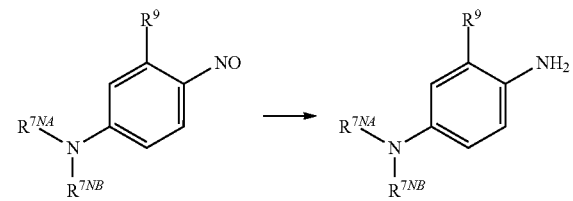

In one embodiment, an N,N-dimethyl-4-nitrosyl aniline, 6, is reduced to form a N,N-dimethyl-1,4-diamino-benzene, 1, as illustrated in the following scheme:

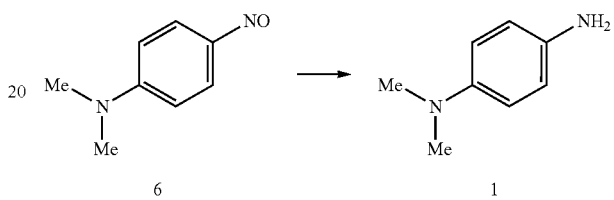

The nitrosylation is performed according to the methods described in WO 2006/032879, which is incorporated by reference herein. In particular the sections relating to Nitrosylation (NOS) at pages 19-20 and Nitrosylation (NOS-2) at pages 46-48 are incorporated herein, along with Examples 1-8 and 17 relating to the synthesis of N,N-dimethyl-1,4-diamino-benzene, and Example 19 relating to the synthesis of N,N-dimethyl-1,4-diamino-3-ethyl-benzene.

Typically the nitrosyl analine VIII is reduced with a reducing agent such as metallic iron under acidic conditions.

Nitrosylation (NOS)

In this step, an N,N-disubstituted-substituted aniline, IX, is nitrosylated to give an N,N-disubstituted-substituted-nitrosyl aniline, VIII, as illustrated in the following scheme:

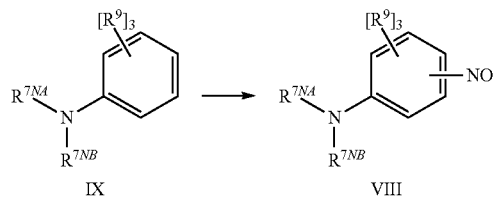

In one embodiment, an N,N-disubstituted-3-optionally substituted aniline H, is 4-nitrosylated to give an N,N-disubstituted-3-optionally substituted-4-nitrosyl aniline, G, as illustrated in the following scheme:

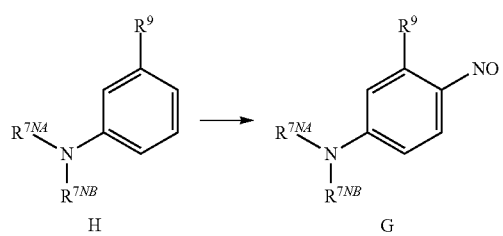

In one embodiment, an N,N-dimethyl aniline, 3, is 4-nitrosylated to give an N,N-dimethyl-4-nitrosyl aniline, 6, as illustrated in the following scheme:

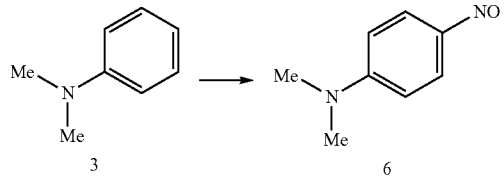

In one embodiment, an N,N-dimethyl-3-ethyl-aniline, 8, is 4-nitrosylated to form the corresponding N,N-dimethyl-3-ethyl-4-nitrosyl aniline, 7, as illustrated in the following scheme:

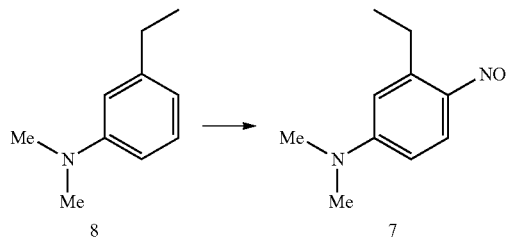

The nitrosylation is performed according to the methods described in WO 2006/032879, which is incorporated by reference herein. In particular, the sections relating to Nitrosylation (NOS-1) at pages 19-20 and Nitrosylation (NOS-2) at pages 46-48 are incorporated herein, along with Examples 1-8, and 17 relating to the preparation of N,N-dimethyl-4-nitrosyl aniline, and Example 19 relating to the preparation of N,N-dimethyl-3-ethyl-4-nitrosyl aniline.

Typically, the aniline IX is treated with a nitrite such as an alkali metal nitrite under acidic conditions to give the nitrosyl aniline VIII.

N,N-Disubstitution (NNDS)

In this step, a substituted-aniline, X, is N,N-disubstituted using an alkyl halide, an alkenyl halide, a haloalkyl halide, a $C_{1-4}$alkylene-$C_{5-10}$aryl halide or a halogenated $C_{1-4}$alkylene-$C_{5-10}$aryl halide, to give a N,N-disubstituted-substituted aniline, IXa, as illustrated in the following scheme:

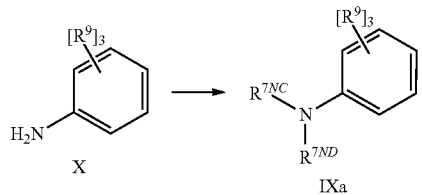

wherein each of —$R^{7NC}$ and —$R^{7ND}$ is independently selected from $C_{1-4}$alkyl; $C_{2-4}$alkenyl; halogenated $C_{1-4}$alkyl; $C_{1-4}$alkylene-$C_{5-10}$aryl and halogenated $C_{1-4}$alkylene-$C_{5-10}$aryl; and —$R^9$ is as defined previously.

In one embodiment, a 3-optionally substituted-aniline, J, is N,N-disubstituted using a alkyl halide, an alkenyl halide, a haloalkyl halide, a $C_{1-4}$alkylene-$C_{5-10}$aryl halide or a halogenated $C_{1-4}$alkylene-$C_{3-10}$aryl halide, to give a N,N-disubstituted-3-optionally substituted-aniline, H, as illustrated in the following scheme:

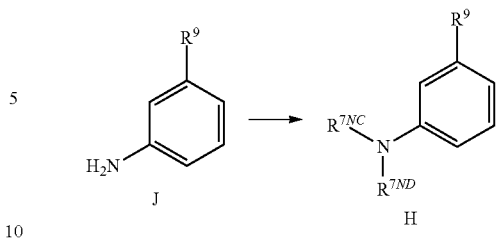

In one embodiment, each of —$R^{7NC}$ and —$R^{7ND}$ is independently selected from: $C_{1-4}$alkyl; $C_{2-4}$alkenyl; and halogenated $C_{1-4}$alkyl.

In one embodiment, each of —$R^{7NC}$ and —$R^{7ND}$ is independently -Me, -Et, -nPr, -nBu, —$CH_2$—CH=$CH_2$, or —$CF_3$.

In one embodiment, each of —$R^{7NC}$ and —$R^{7ND}$ is independently $C_{1-4}$alkyl.

In one embodiment, each of —$R^{7NC}$ and —$R^{7ND}$ is independently -Me or -Et.

In one embodiment, each of —$R^{7NC}$ and —$R^{7ND}$ is independently -Me.

In one embodiment, each of —$R^{7NC}$ and —$R^{7ND}$ is independently -Et.

In one embodiment, —$R^{mc}$ and —$R^{7ND}$ are the same.

In one embodiment, —$R^{7NC}$ and —$R^{7ND}$ are different.

In one embodiment, a 3-ethyl-aniline, 8, is N,N-dimethylated using a methyl halide, to give a N,N-dimethyl-3-ethyl-aniline, 9, as illustrated in the following scheme:

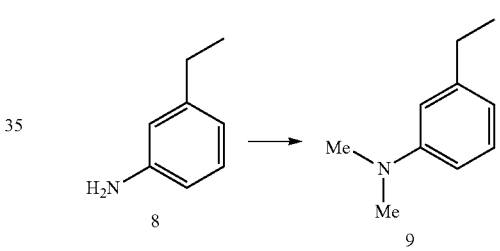

The disubstitution is performed according to the methods described in WO 2006/032879, which is incorporated by reference herein. In particular, the section relating to N,N-Disubstitution (NNDS-2) at pages 45-46 is incorporated herein, along with Example 19 relating to the preparation of N,N-dimethyl-m-ethyl-aniline.

Typically aniline X is treated with an alkyl halide, an alkenyl halide, or a haloalkyl halide under basic conditions to give substituted aniline IXa.

Di-N,N-Disubstitution (DNNDS)

In this step, a N,N-disubstituted-diamino-substituted benzene, Ia, is N,N-disubstituted using an alkyl halide, an alkenyl halide, a haloalkyl halide, a $C_{1-4}$alkylene-$C_{5-10}$aryl halide or a halogenated $C_{1-4}$alkylene-$C_{5-10}$aryl halide, to give a di-N,N-disubstituted-substituted aniline, Ic, as illustrated in the following scheme:

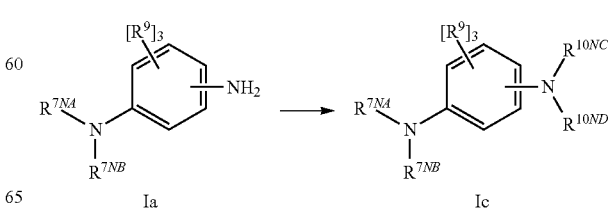

wherein each of —$R^{10NC}$ and —$R^{10ND}$ is independently selected from $C_{1-4}$alkyl; $C_{2-4}$alkenyl; halogenated $C_{1-4}$alkyl; $C_{1-4}$alkylene-$C_{5-10}$aryl and halogenated $C_{1-4}$alkylene-$C_{5-10}$aryl; and —$R^{7NA}$, —$R^{7NB}$, and —$R^9$ are as previously defined.

Substantially Purified Forms

One aspect of the present invention pertains to compounds, as described herein, in substantially purified form and/or in a form substantially free from contaminants.

In one embodiment, the substantially purified form is at least 50% by weight, e.g., at least 60% by weight, e.g., at least 70% by weight, e.g., at least 80% by weight, e.g., at least 90% by weight, e.g., at least 95% by weight, e.g., at least 97% by weight, e.g., at least 98% by weight, e.g., at least 99% by weight.

In one embodiment, the contaminants represent no more than 50% by weight, e.g., no more than 40% by weight, e.g., no more than 30% by weight, e.g., no more than 20% by weight, e.g., no more than 10% by weight, e.g., no more than 5% by weight, e.g., no more than 3% by weight, e.g., no more than 2% by weight, e.g., no more than 1% by weight.

Salts

It may be convenient or desirable to prepare, purify, and/or handle a corresponding salt of a compound described herein. For example, if the compound is anionic, or has a functional group which may be anionic (e.g., —COOH may be -coo), then a salt may be formed with a suitable cation. Examples of suitable inorganic cations include, but are not limited to, alkali metal ions such as $Na^+$ and $K^+$, alkaline earth cations such as $Ca^{2+}$ and $Mg^{2+}$, and other cations such as $Al^{+3}$. Examples of suitable organic cations include, but are not limited to, ammonium ion (i.e., $NH_4^+$) and substituted ammonium ions (e.g., $NH_3R^+$, $NH_2R_2^+$, $NHR_3^+$, $NR_4^+$). Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is $N(CH_3)_4^+$.

If the compound is cationic, or has a functional group which may be cationic (e.g., —$NH_2$ may be —$NH_3^+$), then a salt may be formed with a suitable anion. Examples of suitable inorganic anions include, but are not limited to, those derived from the following inorganic acids: hydrochloric, hydrobromic, hydroiodic, sulfuric, sulfurous, nitric, nitrous, phosphoric, and phosphorous.

Examples of suitable organic anions include, but are not limited to, those derived from the following organic acids: 2-acetoxybenzoic, acetic, ascorbic, aspartic, benzoic, camphorsulfonic, cinnamic, citric, edetic, ethanedisulfonic, ethanesulfonic, fumaric, glucheptonic, gluconic, glutamic, glycolic, hydroxymaleic, hydroxynaphthalene carboxylic, isethionic, lactic, lactobionic, lauric, maleic, malic, methanesulfonic, mucic, oleic, oxalic, palmitic, pamoic, pantothenic, phenylacetic, phenylsulfonic, propionic, pyruvic, salicylic, stearic, succinic, sulfanilic, tartaric, toluenesulfonic, trifluoroacetic, and valeric. Examples of suitable polymeric organic anions include, but are not limited to, those derived from the following polymeric acids: tannic acid, carboxymethyl cellulose.

Unless otherwise specified, a reference to a particular compound also includes salt forms thereof. In one embodiment, a reference to a salt also includes mixed salt forms thereof.

Solvates and Hydrates

It may be convenient or desirable to prepare, purify, and/or handle a corresponding solvate of the compound. The term "solvate" is used herein in the conventional sense to refer to a complex of solute (e.g., compound, salt of compound) and solvent. If the solvent is water, the solvate may be conveniently referred to as a hydrate, for example, a mono-hydrate, a di-hydrate, a tri-hydrate, etc.

Unless otherwise specified, a reference to a particular compound also includes solvate and hydrate forms thereof.

Formulations

The diaminophenothiazinium compounds may be provided in a composition or formulation for administration to a subject, for example a subject having AD. While it is possible for the compound to be used (e.g., administered) alone, it is often preferable to present it as a composition or formulation.

In one aspect of the invention there is provided a method of preparing a composition or formulation comprising a diaminophenothiazinium compound. The method includes the synthesis of a diaminophenothiazinium compound comprising one or more of the steps described herein. In one embodiment, the method further comprises the step of admixing at least one diaminophenothiazinium compound, as defined herein, together with one or more other pharmaceutically acceptable ingredients well known to those skilled in the art, e.g., carriers, diluents, excipients, etc. If formulated as discrete units (e.g., tablets, etc.), each unit contains a predetermined amount (dosage) of the active compound.

In one embodiment, the composition is a pharmaceutical composition (e.g., formulation, preparation, medicament) comprising a diaminophenothiazinium compound, as described herein, and a pharmaceutically acceptable carrier, diluent, or excipient.

In one embodiment, the composition is a pharmaceutical composition comprising at least one diaminophenothiazinium compound, as described herein, together with one or more other pharmaceutically acceptable ingredients well known to those skilled in the art, including, but not limited to, pharmaceutically acceptable carriers, diluents, excipients, adjuvants, fillers, buffers, preservatives, anti-oxidants, lubricants, stabilisers, solubilisers, surfactants (e.g., wetting agents), masking agents, colouring agents, flavouring agents, and sweetening agents.

In one embodiment, the composition further comprises other active agents, for example, other therapeutic or prophylactic agents.

Suitable carriers, diluents, excipients, etc. can be found in standard pharmaceutical texts. See, for example, Handbook of Pharmaceutical Additives, 2nd Edition (eds. M. Ash and I. Ash), 2001 (Synapse Information Resources, Inc., Endicott, N.Y., USA); Remington: The Science and Practice of Pharmacy, 20th Edition (ed. Gennaro et al.), 2000, Lippincott, Williams & Wilkins, Baltimore; and Handbook of Pharmaceutical Excipients, 2nd Edition (eds A. Wade and P. J. Weller), 1994, American Pharmaceutical Association, Washington and The Pharmaceutical Press, London.

The term "pharmaceutically acceptable," as used herein, pertains to compounds, ingredients, materials, compositions, dosage forms, etc., which are, within the scope of sound medical judgment, suitable for use in contact with the tissues of the subject in question (e.g., human) without excessive toxicity, irritation, allergic response, or other problem or complication, commensurate with a reasonable benefit/risk ratio. Each carrier, diluent, excipient, etc. must also be "acceptable" in the sense of being compatible with the other ingredients of the formulation.

The formulations may be prepared by any methods well known in the art of pharmacy. Such methods include the step of bringing into association the active compound with a carrier which constitutes one or more accessory ingredients. In general, the formulations are prepared by uniformly and intimately bringing into association the active compound with carriers (e.g., liquid carriers, finely divided solid carrier, etc.), and then shaping the product, if necessary.

The formulation may be prepared to provide for rapid or slow release; immediate, delayed, timed, or sustained release; or a combination thereof.

Formulations suitable for parenteral administration (e.g., by injection), include aqueous or non-aqueous, isotonic, pyrogen-free, sterile liquids (e.g., solutions, suspensions), in which the active ingredient is dissolved, suspended, or otherwise provided (e.g., in a liposome or other microparticulate). Such liquids may additional contain other pharmaceutically acceptable ingredients, such as anti-oxidants, buffers, preservatives, stabilisers, bacteriostats, suspending agents, thickening agents, and solutes which render the formulation isotonic with the blood (or other relevant bodily fluid) of the intended recipient. Examples of excipients include, for example, water, alcohols, polyols, glycerol, vegetable oils, and the like. Examples of suitable isotonic carriers for use in such formulations include Sodium Chloride Injection, Ringer's Solution, or Lactated Ringer's Injection. Typically, the concentration of the active ingredient in the liquid is from about 1 ng/ml to about 10 μg/ml, for example from about 10 ng/ml to about 1 μg/ml. The formulations may be presented in unit-dose or multi-dose sealed containers, for example, ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules, and tablets.

Uses

In one aspect the present invention provides diaminophenothiazinium compounds and formulations comprising diaminophenothiazinium compounds as described herein for use in therapy.

In other aspects, the invention pertains to compounds obtained or obtainable by the methods described herein for use in therapy. In one embodiment, the compound is a compound obtained by the methods described herein.

The compounds and compositions described herein may reverse or inhibit the aggregation of tau protein (e.g. in the form of paired helical filaments (PHFs), optionally in neurofibrillary tangles (NFTs)) in the brain of a mammal.

One aspect of the invention is the use of a diaminophenothiazinium compound (for example, obtained by the methods described herein) to reverse or inhibit the aggregation of tau protein. This aggregation may be in vitro, or in vivo, and may be associated with a tauopathy disease state as discussed herein. Also provided are methods of reversing or inhibiting the aggregation of tau protein comprising contacting the aggregate or protein with a compound as described herein.

As discussed below, various tauopathy disorders that have been recognized which feature prominent tau pathology in neurons and/or glia and this term has been used in the art for several years. The similarities between these pathological inclusions and the characteristic tau inclusions in diseases such as AD indicate that the structural features are shared and that it is the topographic distribution of the pathology that is responsible for the different clinical phenotypes observed. In addition to specific diseases discussed below, those skilled in the art can identify tauopathies by combinations of cognitive or behavioural symptoms, plus additionally through the use of appropriate ligands for aggregated tau as visualised using PET or MRI, such as those described in WO02/075318.

One aspect of the present invention pertains to a method of treatment or prophylaxis of a tauopathy condition in a patient, comprising administering to said patient a therapeutically-effective amount of a compound of formula (I), as described herein. In one embodiment, the compound of formula (I) is obtained by the methods described herein.

Aspects of the present invention relate to "tauopathies". As well as Alzheimer's disease (AD), the pathogenesis of neurodegenerative disorders such as Pick's disease and Progressive Supranuclear Palsy (PSP) appears to correlate with an accumulation of pathological truncated tau aggregates in the dentate gyrus and stellate pyramidal cells of the neocortex, respectively. Other dementias include fronto-temporal dementia (FTD); FTD with parkinsonism linked to chromosome 17 (FTDP-17); disinhibition-dementia-parkinsonism-amyotrophy complex (DDPAC); pallido-ponto-nigral degeneration (PPND); Guam-amyotrophic lateral sclerosis (ALS) syndrome; pallido-nigro-luysian degeneration (PNLD); cortico-basal degeneration (CBD); Dementia with Argyrophilic grains (AgD); Dementia pugilistica (DP) wherein despite different topography, NFTs are similar to those observed in AD (Hof P. R., Bouras C., Buée L., Delacourte A., Perl D. P. and Morrison J. H. (1992) Differential distribution of neurofibrillary tangles in the cerebral cortex of dementia pugilistica and Alzheimer's disease cases. Acta Neuropathol. 85, 23-30). Others are discussed in Wischik et al. 2000, loc. cit, for detailed discussion—especially Table 5.1).

Abnormal tau in NFTs is found also in Down's Syndrome (DS) (Flament S., Delacourte A. and Mann D.M.A. (1990) Phosphorylation of tau proteins: a major event during the process of neurofibrillary degeneration. A comparative study between AD and Down's syndrome. Brain Res., 516, 15-19). Also Dementia with Lewy bodies (DLB) (Harrington, C. R., Perry, R. H., Perry, E. K., Hurt, J., McKeith, I. G., Roth, M. & Wischik, C. M. (1994) Senile dementia of Lewy body type and Alzheimer type are biochemically distinct in terms of paired helical filaments and hyperphosphorylated tau protein. Dementia 5, 215-228). Tau-positive NFTs are also found in Postencephalitic parkinsonism (PEP) (Hof P. R., Charpiot, A., Delacourte A., Buee, L., Purohit, D., Perl D. P. and Bouras, C. (1992) Distribution of neurofibrillary tangles and senile plaques in the cerebral cortex in postencephalitic parkinsonism. Neurosci. Lett. 139, 10-14). Glial tau tangles are observed in Subacute sclerosing panencephalitis (SSPE) (Ikeda K., Akiyama H., Kondo H., Arai T., Arai N. and Yagishita S. (1995) Numerous glial fibrillary tangles in oligodendroglia in cases of subacute sclerosing panencephalitis with neurofibrillary tangles. Neurosci. Lett., 194, 133-135).

Additionally there is a growing consensus in the literature that a tau pathology may also contribute more generally to cognitive deficits and decline, including in mild cognitive impairment (MCI) (see e.g. Braak, H., Del Tredici, K, Braak, E. (2003) Spectrum of pathology. In Mild cognitive impairment: Aging to Alzheimer's disease edited by Petersen, R. C.; pp. 149-189).

In this and all other aspects of the invention relating to tauopathies, preferably the tauopathy is selected from the list consisting of the indications above, i.e., AD, Pick's disease, PSP, FTD, FTDP-17, DDPAC, PPND, Guam-ALS syndrome, PNLD, and CBD and AgD, DS, SSPE, DP, PEP, DLB and MCI.

In one preferred embodiment the tauopathy is Alzheimer's disease (AD).

One aspect of the present invention pertains to a compound of formula (I), as described herein, for use in a method of treatment or prophylaxis (e.g., of a tauopathy condition) of the human or animal body by therapy. In one embodiment, the compound of formula (I) is obtained by the methods described herein.

One aspect of the present invention pertains to use of a compound of formula (I), as described herein, in the manufacture of a medicament for use in the treatment or prophylaxis of a tauopathy condition. In one embodiment, the compound of formula (I) is obtained by the methods described herein.

A further embodiment is a method of treatment or prophylaxis of a disease of tau protein aggregation as described herein, which method comprises administering to a subject a diaminophenothiazinium compounds, or therapeutic composition comprising the same, such as to inhibit the aggregation of the tau protein associated with said disease state.

EXAMPLES

The following examples are provided solely to illustrate the present invention and are not intended to limit the scope of the invention, as described herein.

Preparation of 2-amino-5-dimethylaminophenyl thiosulfonic acid (2)

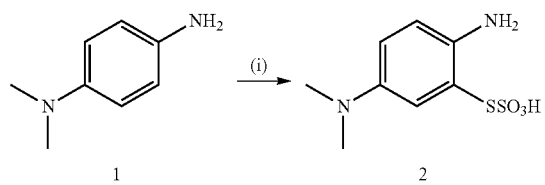

(i): $Na_2S_2O_3 \cdot 5H_2O$, $Na_2S_2O_8$, $H_2O$, MeOH, 5° C.

Example 1

Synthesis of 2-amino-5-dimethylaminophenylthiosulfonic acid

N',N'-dimethyl-p-phenylene diamine (10 g, 0.0735 mols) was added to a round bottom flask. To this was added de-ionised water (160 ml) and methanol (40 ml) and the solution was then cooled to 5° C. Sodium thiosulfate (20 g, 0.0808 mols) in water (20 ml) was added to the solution in one aliquot. Sodium persulfate (17.5 g, 0.0735 mols) in water (40 ml) was added drop-wise over a 15 minute period. The reaction mixture was stirred for 3 hours at 5° C. and then warmed to 22° C. over a period of 1 hour. The dark solid which precipitated was collected via filtration. The black solid was washed with water (50 ml) then dried at 40° C. for 16 hours, 7.88 g (43%).

Purification of 2-amino-5-dimethylaminophenylthiosulfonic acid 2-amino-5-dimethylaminophenylthiosulfonic acid (2.16 g, 0.0087 mols) was added to a round bottom flask and ethyl acetate (108 ml) was added. The slurry was heated to reflux for one hour and then cooled to a temperature between 18-22° C. Once the slurry had cooled to the desired temperature the purple solid was collected via filtration. The purple solid was washed with ethyl acetate (100 ml) and the solid was dried under vacuum (1000 mbar) at 40° C. for 16 hours, 1.82 g (84%).
Mp: 195-197° C.

$\upsilon_{max}$ (KBr)/cm$^{-1}$: 3454 (N—H), 3350 (N—H), 3033 (C—H), 1621 (C=C) 1463 (C—C or O=S=O), 1170 (O=S=O), 1016 (O=S=O).

$\delta_H$(600 MHz, DMSO-d$_6$) 2.98 (6H, s, N—CH$_3$), 7.03-7.08 (m, 2H, Ar—H), 7.19 (s, 1H Ar—H).

Mass Spec (m/z) ESI high resolution: calculated: 249.0368. found: 249.0361 [M+H]$^+$;
169.0800 [(M+H)—SO$_3$]$^+$.

Example 2

N',N'-dimethyl-p-phenylene diamine (5 g, 0.036 mols) was added to a round bottom flask. To this was added de-ionised water (80 ml) and tetrahydrofuran (20 ml) and the solution was then cooled to 5° C. Sodium thiosulfate (10.03 g, 0.040 mols) in water (20 ml) was added to the solution in one aliquot. Sodium persulfate (8.75 g, 0.036 mols) in water (40 ml) was added drop-wise over a 15 minute period. The reaction mixture was stirred for 3 hours at 5° C. and then warmed to 22° C. over a period of 1 hour. The black solid which precipitated was collected via filtration. The black solid was washed with water (50 ml) then dried under vacuum (1000 mbar) at 40° C. for 16 hours. N',N'-dimethyl-p-phenylene diamine-5-thiosulfonic acid was added to a round bottom flask and ethyl acetate (100 ml) was added. The slurry was heated to reflux for one hour and then cooled to a temperature between 18-22° C. Once the slurry had cooled to the desired temperature the purple solid was collected via filtration. The purple solid was washed with ethyl acetate (50 ml) and dried under vacuum (1000 mbar) at 40° C. for 16 hours, 3.7 g (40%).
Mp: 197-198° C.

$\upsilon_{max}$ (KBr)/cm$^{-1}$: 3452 (N—H), 3344 (N—H), 3032 (C—H), 1621 (C=C), 1463 (C—C or O=S=O), 1165 (O=S=O), 1015 (O=S=O).

$\delta_H$(400 MHz, DMSO-d$_6$) 2.98 (6H, s, N—CH$_3$), 6.99-7.01 (m, 1H, Ar—H) 7.06-7.08 (d, 1H, Ar—H $J^{AB}$=8.4 Hz), 7.17 (s, 1H, Ar—H).

Mass Spec (m/z) ESI high resolution: calculated: 249.0368. found: 249.0359 [M+H]$^+$; 169.0794 [(M+H)—SO$_3$]$^+$.

Example 3

N',N'-dimethyl-p-phenylene diamine (5 g, 0.036 mols) was added to a round bottom flask. To this was added de-ionised water (80 ml) and acetonitrile (20 ml) and the solution was then cooled to 5° C. Sodium thiosulfate (10.03 g, 0.040 mols) in water (20 ml) was added to the solution in one aliquot. Sodium persulfate (8.75 g, 0.036 mols) in water (40 ml) was added drop-wise over a 15 minute period. The reaction mixture was stirred for 3 hours at 5° C. and then warmed to 22° C. over a period of 1 hour. The black solid which precipitated was collected via filtration. The black solid was washed with water (50 ml) then dried under vacuum (1000 mbar) at 40° C. for 16 hours. N',N'-dimethyl-p-phenylene diamine-5-thiosulfonic acid was added to a round bottom flask and ethyl acetate (100 ml) was added. The slurry was heated to reflux for one hour and then cooled to a temperature between 18-22° C. Once the slurry had cooled to the desired temperature the purple solid was collected via filtration. The purple solid was washed with ethyl acetate (50 ml) and dried under vacuum (1000 mbar) at 40° C. for 16 hours, 4.3 g (47%).
Mp: 199° C.

$\upsilon_{max}$ (KBr)/cm$^{-1}$: 3453 (N—H), 3347 (N—H), 3032 (C—H), 1621 (C=C), 1463 (C—C or O=S=O), 1169 (O=S=O), 1010 (O=S=O).

$\delta_H$(400 MHz, DMSO-d$_6$) 2.98 (6H, s, N—CH$_3$), 7.00-7.02 (m, 1H, Ar—H), 7.06-7.09 (d, 1H, Ar—$\underline{H}$ $J^{AB}$=9.2 Hz), 7.18 (s, 1H, Ar—$\underline{H}$).

Mass Spec (m/z) ESI high resolution: calculated: 249.0368. found: 249.0363 [M+H]$^+$; 169.0794 [(M+H)—SO$_3$]$^+$.

Example 4

N,N'-dimethyl-p-phenylene diamine (5 g, 0.036 mols) was added to a round bottom flask. To this was added de-ionised water (80 ml) and N,N-dimethylformamide (20 ml) and the solution was then cooled to 5° C. Sodium thiosulfate (10.03 g, 0.040 mols) in water (20 ml) was added to the solution in one aliquot. Sodium persulfate (8.75 g, 0.036 mols) in water (40 ml) was added drop-wise over a 15 minute period. The reaction mixture was stirred for 3 hours at 5° C. and then warmed to 22° C. over a period of 1 hour. The black solid which precipitated was collected via filtration. The black solid was washed with water (50 ml) then dried under vacuum (1000 mbar) at 40° C. for 16 hours. N',N'-dimethyl-p-phenylene diamine-5-thiosulfonic acid was added to a round bottom flask and ethyl acetate (100 ml) was added. The slurry was heated to reflux for one hour and then cooled to a temperature between 18-22° C. Once the slurry had cooled to the desired temperature the purple solid was collected via filtration. The purple solid was washed with ethyl acetate (50 ml) and dried under vacuum (1000 mbar) at 40° C. for 16 hours, 4.8 g (52%).

Mp: 198-199° C.

$\upsilon_{max}$ (KBr)/cm$^{-1}$: 3457 (N—H), 3346 (N—H), 3032 (C—H), 1621 (C=C), 1463 (C—C or O=S=O), 1166 (O=S=O), 1011 (O=S=O).

$\delta_H$(400 MHz, DMSO-d$_6$) 2.98 (6H, s, N—CH$_3$), 7.02 (m, 1H, Ar—H), 7.06-7.09 (d, 1H Ar—$\underline{H}$ $J^{AB}$=8.4 Hz), 7.18 (s, 1H, Ar—$\underline{H}$).

Mass Spec (m/z) ESI high resolution: calculated: 249.0368. found: 249.0369 [M+H]$^+$; 169.0802 [(M+H)—SO$_3$]$^+$.

Example 5

N',N'-dimethyl-p-phenylene diamine (5 g, 0.036 mols) and dodecylbenzenesulfonic acid, sodium salt (0.13 g, 0.00036 mols) were added to a round bottom flask. De-ionised water (100 ml) was added and the solution was then cooled to 5° C. Sodium thiosulfate (10.03 g, 0.040 mols) in water (20 ml) was added to the solution in one aliquot. Sodium persulfate (8.75 g, 0.036 mols) in water (40 ml) was added dropwise over a 15 minute period. The reaction mixture was stirred for 3 hours at 5° C. and then warmed to 22° C. over a period of 1 hour. The black solid which precipitated was collected via filtration. The black solid was washed with water (50 ml) then dried under vacuum (1000 mbar) at 40° C. for 16 hours. N',N$^1$-dimethyl-p-phenylene diamine-5-thiosulfonic acid was added to a round bottom flask and ethyl acetate (100 ml) was added. The slurry was heated to reflux for one hour and then cooled to a temperature between 18-22° C. Once the slurry had cooled to the desired temperature the purple solid was collected via filtration. The purple solid was washed with ethyl acetate (50 ml) and dried under vacuum (1000 mbar) at 40° C. for 16 hours, 4.6 g (50%).

Mp: 198-199° C.

$\upsilon_{max}$ (KBr)/cm$^{-1}$: 3450 (N—H), 3342 (N—H), 3032 (C—H), 1620 (C=C), 1463 (C—C or O=S=O), 1174 (O=S=O), 1010 (O=S=O).

$\delta_H$(400 MHz, DMSO-d$_6$) 2.98 (6H, s, N—CH$_3$), 7.00-7.02 (d, $J^{AB}$=7.6 Hz, 1H, Ar—H), 7.06-7.08 (d, $J^{AB}$=8.8 Hz, 1H, Ar—H), 7.18 (s, 1H, Ar—$\underline{H}$).

Mass Spec (m/z) ESI high resolution: calculated: 249.0368. found: 249.0363 [M+H]$^+$; 169.0794 [(M+H)—SO$_3$]$^+$.

Example 6

N',N'-dimethyl-p-phenylenediamine (5 g, 0.036 mols) was added to a round bottom flask. To this was added de-ionised water (100 ml) and the solution was then cooled to 5° C. Sodium thiosulfate (10.03 g, 0.040 mols) in water (20 ml) was added to the solution in one aliquot. Sodium persulfate (8.75 g, 0.036 mols) in water (40 ml) was added drop-wise over a 15 minute period. The reaction mixture was stirred for 3 hours at 5° C. and then warmed to 22° C. over a period of 1 hour. The black solid which precipitated was collected via filtration. The black solid was washed with water (50 ml) then dried under vacuum (1000 mbar) at 40° C. for 16 hours. N',N'-dimethyl-p-phenylene diamine-5-thiosulfonic acid was added to a round bottom flask and ethyl acetate (100 ml) was added. The slurry was heated to reflux for one hour and then cooled to a temperature between 18-22° C. Once the slurry had cooled to the desired temperature the purple solid was collected via filtration. The purple solid was washed with ethyl acetate (50 ml) and dried under vacuum (1000 mbar) at 40° C. for 16 hours, 5.1 g (56%). Actual value=49% by NMR with internal standard (DSS)

Mp: 201-202° C.

$\upsilon_{max}$ (KBr)/cm$^{-1}$: 3455 (N—H), 3346 (N—H), 3033 (C—H), 1621 (C=C), 1463 (C—C or O=S=O), 1170 (O=S=O), 1013 (O=S=O).

$\delta_H$(400 MHz, DMSO-d$_6$) 2.96 (6H, s, N—CH$_3$), 7.00-7.03 (m, 2H, Ar—H), 7.15 (s, 1H, Ar—H).

Mass Spec (m/z) ESI high resolution: calculated: 249.0368. found: 249.0376 [M+H]$^+$; 169.0790 [(M+H)—SO$_3$]$^+$.

Synthesis 2

Preparation of thiosulfonic acid of Bindshedlers green (3)

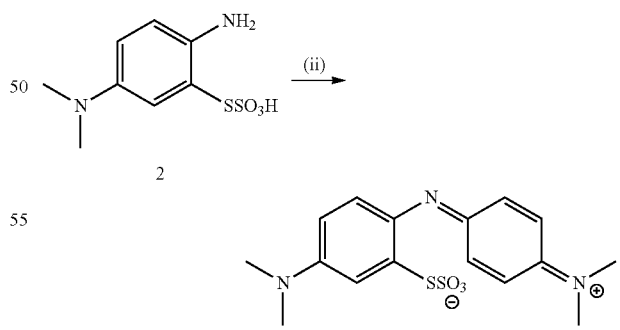

(ii): H$_2$O, H$_2$SO$_4$, (CH$_3$)$_2$NC$_6$H$_5$, Na$_2$S$_2$O$_8$, H$_2$O, NaOH(aq), 5° C.

2-amino-5-dimethylaminophenylthiosulfonic acid (15 g, 0.0605 mols) was added to a round bottom flask and de-ionised water (300 ml) was added. The solution was cooled to ~5° C. and a pre-cooled mixture of N,N-dimethylaniline (7.32 g, 0.0605 mols), sulphuric acid (5.93 g, 0.0605 mols) and de-ionised water (7.32 ml) was added in one aliquot. The pH of the mixture was adjusted to pH ~7.5 using 6 M sodium hydroxide (~30 ml). Sodium persulfate (43.18 g, 0.181 mols) in water (62 ml) was added drop-wise over a period of ~20 minutes. The reaction mixture was stirred for 2 hours and then warmed to 22° C. over a 1 hour period. The black solid was collected via filtration and air dried for 16 hours.

$\upsilon_{max}$ (KBr)/cm$^{-1}$: 1587 (C=C), 1360 (O=S=O), 1013 (O=S=O)

Mass Spec (m/z) ESI high resolution: calculated: 388.766. found: 388.0774 [M+Na]$^+$.

Synthesis 3

3,7-Bis(dimethylamino)phenothiazin-5-ium chloride(methylthioninium chloride) (5)

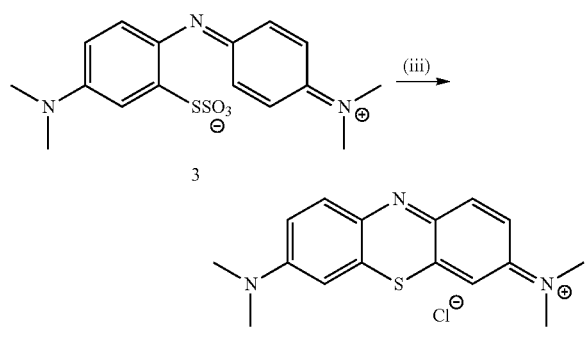

(iii): CuSO$_4$·5H$_2$O, H$_2$O, HCl, 85° C., NaCl

De-ionised water (455 ml) was adjusted to pH 2 with hydrochloric acid and copper sulfate (2.06 g 0.0825 mols) was added. 3 was added to a round bottom flask and the copper sulfate solution was added. The reaction mixture was heated to ~85° C. and stirred for 1 hour. The deep blue solution was allowed to cool to 22° C. and then filtered away from insolubles. The filtrate was added to a round bottom flask and sodium chloride (100 g, 1.73 mols) was added. The solution was stirred until precipitate was seen (~1 hour). The solid which precipitated was collected via filtration and dissolved in water (20 ml) and the solution was acidified to pH 1 using hydrochloric acid. The solution was stirred at room temperature for ~30 minutes and the resulting solid was collected via filtration and dried under vacuum (1000 mbar) at 40° C. for 16 hours. 3.44 g (16%, calculated as MTC.2H$_2$O from 2)

Mp: 190° C. (decomposed)

$\upsilon_{max}$ (KBr)/cm$^{-1}$: 3418 (O—H, St (H$_2$O as a solvate)), 1594 (C=C (Aromatic), St), 1489 (C=C (Aromatic), St), 1393 (C—H (Aromatic), St), 1333 (C—N, St), 1175 (C—H (Aromatic), St), 1144 (C—H (Aromatic), St)

$\delta_H$(400 MHz, D$_2$O): 3.09 (s, 12H, N—CH$_3$), 6.84 (s, 2H, Ar—H), 7.03, 7.05 (d, J$^{AB}$=8.8 Hz, 2H, A-H,), 7.36, 7.39 (d, J$^{AB}$=9.2 Hz, 2H, Ar—H,).

$\delta_c$(150 MHz, D$_2$O): 40.3 (N—CH$_3$), 105.7 (Ar—C), 118.0 (Ar—C), 133.2 (Ar—C), 133.5 (Ar—C), 135.9 (Ar—C), 152.7 (Ar—C).

Mass Spec (m/z) ESI high resolution: calculated: 284.1216. found: 284.1218 [M—Cl]$^+$.

HPLC: retention time=17.962 mins, peak area=85.17%

UV, $\lambda_{max}$: 663 nm

Moisture analysis: 9.6% volatiles at 105° C.

MT$^+$ assay: Mr content=49%; MTC.2H$_2$O=69%; a significant amount of azure B was detected.

Synthesis 4

2-amino-5-diethylaminophenyl thiosulfonic acid (6)

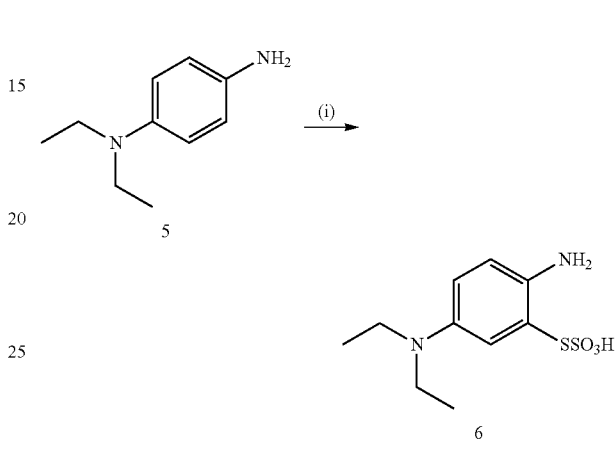

(i): Na$_2$S$_2$O$_3$·5H$_2$O, Na$_2$S$_2$O$_8$, H$_2$O, MeOH, 5° C.

N',N'-diethyl-p-phenylenediamine (5 g, 0.030 mols) was added to a round bottom flask. To this was added de-ionised water (80 ml) and methanol (20 ml) and the solution was then cooled to 5° C. Sodium thiosulfate (8.31 g, 0.033 mols) in water (20 ml) was added to the solution in one aliquot. Sodium persulfate (7.25 g, 0.030 mols) in water (40 ml) was added drop-wise over a 15 minute period. The reaction mixture was stirred for 3 hours at 5° C. and then warmed to 22° C. over a period of 1 hour. The dark brown solid which precipitated was collected via filtration. The dark brown solid was washed with water (50 ml) then dried under vacuum (1000 mbar) at 40° C. for 16 hours, 4.43 g (52%).

2-amino-5-diethylaminophenyl thiosulfonic acid was added to a round bottom flask and ethyl acetate (240 ml) was added. The slurry was heated to reflux for one hour and then cooled to a temperature between 18-22° C. Once the solution had cooled to the desired temperature the purple solid was collected via filtration. The purple solid was washed with ethyl acetate (50 ml) and the solid was dried under vacuum (1000 mbar) at 40° C. for 16 hours, 4.2 g.

Final yield=49% Actual value=45% by NMR with internal standard (DSS)

Mp: 203-204° C.

$\upsilon_{max}$ (KBr)/cm$^{-1}$: 3434 (N—H, St), 3336 (N—H, St), 2985 (C—H, St), 1624 (C=C, St), 1470 (C—C or O=S=O), 1182 (O=S=O), 1019 (O=S=O).

$\delta_H$(400 MHz, DMSO-d$_6$) 1.021 (6H, t, N—CH$_2$CH$_3$), 3.44 (m, 4H, N—CH$_2$CH$_3$), 6.86-6.88 (d, 1H, Ar—H J$^{AB}$=8.0 Hz), 7.16-7.18 (d, 1H, Ar—H J$^{AB}$=8.4 Hz), 7.40 (s, 1H, Ar—H).

Mass Spec (m/z) ESI high resolution: calculated: 299.0495. found: 299.0503 [M+Na]$^+$; 197.1112 [(M+H)—SO$_3$]$^+$.

Synthesis 5

Preparation of 2-amino-5-ethylmethylaminophenyl thiosulfonic acid (8)

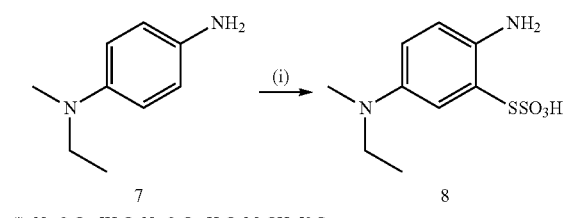

(i): Na$_2$S$_2$O$_3$·5H$_2$O, Na$_2$S$_2$O$_8$, H$_2$O, MeOH, 5° C.

To a 250 ml round bottom flask was added N-ethyl-N-methyl-p-phenylene diamine (2 g, 13.31 mmol, MW 150.23 g/mol), water (32 ml), methanol (8 ml) and sodium thiosulfate pentahydrate (3.63 g, 14.64 mmol, MW 248.18 g/mol, dissolved in 5 ml of water). The mixture was cooled over ice water to between 2-5° C. Sodium persulfate (3.17 g, 13.31 mmol, MW 238.10 g/mol, dissolved in 8 ml of water) was added drop-wise to the cooled mixture and the reaction was allowed to react for three hours. The mixture was then allowed to increase in temperature to 22° C. before being filtered. The grey solid was washed with water (3×20 ml) and ethyl acetate (3×25 ml) to give the crude product (1.29 g, 37%, MW 262.35 g/mol) as a light grey solid.

Mp: 197-198° C. (H$_2$O)

$\upsilon_{max}$ (KBr)/cm$^{-1}$; 3435 (NH), 3338 (NH), 3004 (C—H), 2941 (=CH), 2706 (SO$_3$H), 1626 (C=C), 1467 (C—C or O=S=O), 1180 (O=S=O), 1017 (O=S=O)

$\delta_H$(400 MHz; D$_2$O); 1.04 (3H, t, J=7 Hz, CH$_3$), 3.03 (3H,s, NCH$_3$), 3.43 (4H, q, J=7 Hz, NCH$_2$) 6.98 (1H, d, J=6.8 Hz, ArH), 7.14 (1H, brd s, ArH), 7.34 (1H, brd s, ArH) Mass Spec (m/z) ESI high resolution: calculated: 263.0524. found, 263.0513 [M+H]$^+$; 183.0948 [(M+H)—SO$_3$]$^+$.

Preparation of ethylmethyithiosulfonic acid of Bindschedlers green (9)

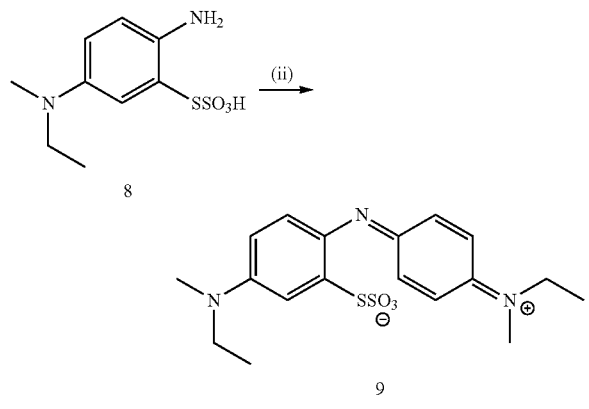

(ii): N-ethyl-N-methylaniline, Na$_2$S$_2$O$_8$, H$_2$O, NaOH$_{(aq)}$

To a 50 ml round bottom flask was added 2-amino-5-ethylmethylaminophenyl thiosulfonic acid (0.5 g, 1.91 mmol, MW 262.35 g/mol) and water (10 ml). The mixture was cooled over ice water to between 2-5° C. A homogeneous solution of N-ethyl-N-methylaniline (0.26 g, 1.91 mmol, 135.21 g/mol), water (0.5 ml) and sulphuric acid (0.19 g, 1.91 mmol, MW 98.08 g/mol) was added to the cooled mixture. The pH of the mixture was then adjusted to pH ~7.5 with sodium hydroxide (6 M, ~1 ml) to give a black slurry. Sodium persulfate (1.36 g, 5.72 mmol, MW 238.10 g/mol, dissolved in 2 ml of water) was added drop-wise to the cooled near neutral slurry and the reaction was allowed to react for two hours. The mixture was then allowed to increase in temperature to 24° C. before being filtered. The black solid was washed with water (3×10 ml) and air dried for two hours to give the crude product (0.42 g, 56%, MW 392.52 g/mol) as a black solid.

$\upsilon_{max}$ (KBr)/cm$^{-1}$; 2979 (C—H), 1594 (C=C), 1386 (O=S=O), 1021 (O=S=O)

Mass Spec (m/z) ESI high resolution: calculated: 396.1416. found: 396.1422 [M+3H]$^+$).

Preparation of ethylmethylthioninium chloride (10)

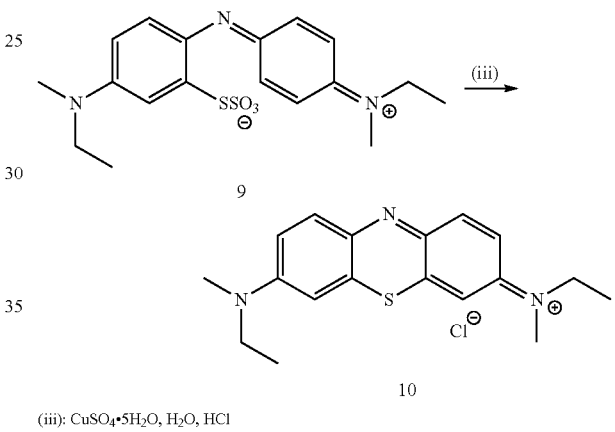

(iii): CuSO$_4$·5H$_2$O, H$_2$O, HCl

To a 50 ml round bottom flask was added N-ethyl-N-methylthiosulfonic acid of Bindschedlers green (0.4 g, 1.02 mmol, MW 392.52 g/mol), aqueous hydrochloric acid (5 ml, pH 2) and copper sulphate pentahydrate (0.04 g, 0.14 mmol, MW 249.69 g/mol). The mixture was heated to 85° C. and stirred at this temperature for 1 hour. The mixture was then allowed to cool to 24° C. before being filtered. The black solid was washed with water (3×0.5 ml). Sodium chloride was added to the deep blue filtrate to precipitate the crude product, which was collected by filtration (0.038 g, 11%, MW 347.91 g/mol) as a purple solid. The crude solid was purified by column chromatography using silica 40-63µ 60 Å with 10% MeOH, 90% DCM as the eluent.

Mp: 178-180° C. (MeOH)

$\upsilon_{max}$ (KBr)/cm$^{-1}$; 2925 (=CH), 1594 (C=C), 1486 (C—C)

$\delta_H$(250 MHz; D$_2$O); 1.20 (6H, t, J=6.5 Hz, CH$_3$), 3.10 (6H,s, NCH$_3$), 3.50 (4H, brd q, NCH$_2$) 6.87 (2H, s, ArH), 7.11 (2H, brd, ArH), 7.34 (2H, d, J=9.5 Hz, ArH)

$\delta_C$(150 MHz; D$_2$O); 11.5, (CH$_3$), 38.3 (NCH$_3$), 48.8 (NCH$_2$), 106.0 (ArC), 118.4 (ArC), 133.9 (ArC), 134.2 (ArC), 136.5 (ArC), 152.6 (ArC)

Mass Spec (m/z) ESI high resolution: calculated: 312.1534. found: 312.1545 [M—Cl]$^+$.

Synthesis 6

Preparation of N,N-di(prop-2-en-1-yl)aniline

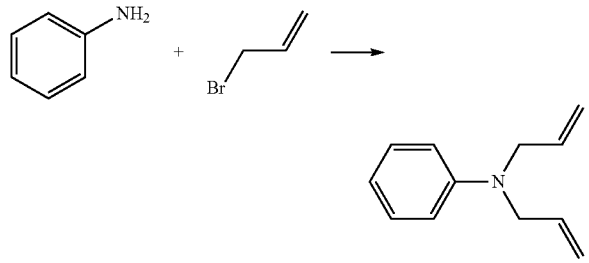

To a stirred solution of aniline (5.62 g, 60.36 mmol) in EtOH (200 ml) and water (50 ml) was added allyl bromide (17.33 g, 143.3 mmol) in one portion followed by solid Na$_2$CO$_3$ (6.69 g, 62.5 mmol). The yellow mixture was then heated under reflux for 17 h, left to cool to room temperature (19° C.) and the EtOH was removed under reduced pressure. The aqueous residue was extracted with Et$_2$O (5×200 ml) and the combined organics were washed with brine (3×200 ml) and dried (Na$_2$SO$_4$). The solvent was removed under reduced pressure to give a brown oil that was distilled over KOH pellets to give the title compound (7.81 g, 75%) as a pale yellow oil.

$\upsilon_{max}$ (KBr)/cm$^{-1}$ 3061 (C—H), 2979 (C—H), 2911 (C—H), 1642 (C═C), 1599 (Ar C═C), 1505 (Ar C═C)

$\delta_H$(400 MHz, CDCl$_3$): 3.95 (ddd, J=1.5, 1.5, 4.4 Hz, 4H, NCH$_2$), 5.18 (ddt, J=1.2, 1.6, 10.8 Hz, 2H, ═CH$_2$), 5.21 (ddt, J=1.6, 1.9, 17.2 Hz, 2H, ═CH$_2$), 5.89 (ddt, J=4.4, 10.8, 17.2 Hz, 2H, ═CH), 6.69-6.74 (m, 3H, Ar—H), 7.20-7.24 (m, 2H, Ar—H)

$\delta_c$(100 MHz, CDCl$_3$): 52.75 (NCH$_2$), 112.34, 115.99, 116.30, 129.08, 134.04, 148.71

Prepared according to Ling et al (2007).

Preparation of 4-Nitro-N,N-di(prop-2-en-1-yl)aniline

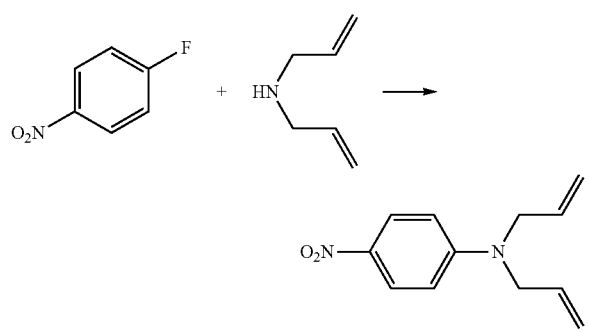

A mixture of 4-fluoronitrobenzene (5.00 g, 35.44 mmol), diallylamine (3.48 g, 4.4 ml, 35.44 mmol) and K$_2$CO$_3$ (5.39 g, 38.98 mmol) in dry DMSO (40 ml) was heated at 100° C. under an atmosphere of argon for 3 h. The reaction mixture was then left to cool to room temperature (23° C.) and added to water (300 ml) and extracted with EtOAc (4×75 ml). The combined organics were washed with brine (100 ml) and dried (Na$_2$SO$_4$). The solvent was removed under reduced pressure to give a red oil that was purified by chromatography (2:1 Hexane/DCM) to give the title compound (4.60 g, 59%) as an orange oil.

$\upsilon_{max}$ (KBr)/cm$^{-1}$ 3085 (C—H), 3011 (C—H), 2983 (C—H), 2912 (C—H), 1643 (alkene C═C), 1596 (NO$_2$), 1516 (Ar C═C), 1488 (Ar C═C), 1315 (NO$_2$)

$\delta_H$(400 MHz, CDCl$_3$): 4.01-4.03 (ddd, J=1.6, 1.6, 4.8 Hz, 4H, NCH$_2$), 5.16 (ddt, J=1.6, 1.9, 17.2 Hz, 2H, CH$_2$═), 5.23 (dq, J=1.6, 1.9, 10.4 Hz, 2H, CH$_2$═), 5.84 (ddt, J=4.4, 10.4, 17.2 Hz, 2H, ═CH), 6.62 (d, J=9.6 Hz, 2H, Ar—H), 8.09 (d, J=9.6 Hz, 2H, Ar—H)

$\delta_c$(100 MHz, CDCl$_3$): 52.95, 110.73, 116.94, 119.27, 126.12, 131.75, 153.26

Mass Spec (m/z) ESI high resolution: calculated: 219.1134. found, 219.1131 [M+H]$^+$.

Data consistent Yi-Chun Hsu et al (2005).

Preparation of N,N-di(prop-2-en-1-yl)benzene-1,4-diamine

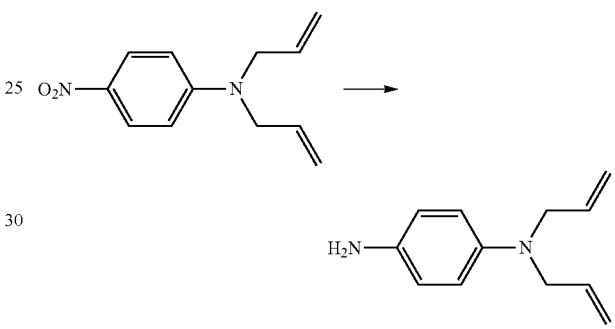

A mixture of 4-nitro-N,N-di(prop-2-en-1-yl)aniline (12.22 g, 55.98 mmol) and tin (II) chloride dihydrate (64.45 g, 279.9 mmol) in EtOH (280 ml) was stirred and heated under reflux for 21 h. The cooled reaction mixture was concentrated under reduced pressure to a volume of 100 ml, and neutralised by the addition of 5 M NaOH. The precipitate was removed by filtration and the filtrate was extracted with EtOAc (4×200 ml). The combined organics were washed with brine (2×200 ml) and dried (Na$_2$SO$_4$). The solvent was removed under reduced pressure to give a brown oil that was purified by chromatography (1:1 Hexane/EtOAc) to give the title compound (7.79 g, 74%) as a brown oil.

$\upsilon_{max}$ (KBr)/cm$^{-1}$ 3413 (NH), 3341 (NH), 3216 (C—H), 3075 (C—H), 3034 (C—H), 3004 (C—H), 2977 (C—H), 1640 (alkene C═C), 1612 (Ar C═C), 1514 (Ar C═C)

$\delta_H$(400 MHz, CDCl$_3$): 2.98-3.68 (br s, 2H, NH$_2$), 3.81 (d, J=4.8 Hz, 4H, NCH$_2$), 5.13 (ddt, J=1.5, 2.0, 10.6 Hz, 2H, CH$_2$═), 5.17 (ddt, J=1.5, 2.0, 17.2 Hz, 2H, CH$_2$═), 5.85 (ddt, J=5.1, 10.1, 17.2 Hz, 2H, ═CH), 6.63 (app br s, 4H, Ar—H))

$\delta_c$(100 MHz, CDCl$_3$): 53.87, 115.46, 116.22, 116.64, 134.71, 137.46, 142.35

Mass Spec (m/z) ESI high resolution: calculated: 189.1392. found: 189.1383 [M+H]$^+$.

Preparation of 2-amino-5-N,N-di(prop-2-en-1-yl) aminophenylthiosulfonic acid (12)

Example 1

A modification of Bernthsten's protocol for the preparation of 2-amino-5-N,N-di(prop-2-en-1-yl)aminophenylthiosulfonic acid has been executed. This preparation uses zinc chloride and aluminium sulfate.

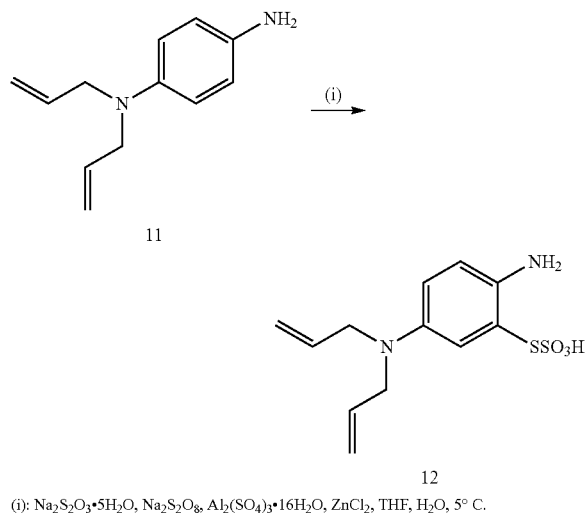

(i): Na$_2$S$_2$O$_3$·5H$_2$O, Na$_2$S$_2$O$_8$, Al$_2$(SO$_4$)$_3$·16H$_2$O, ZnCl$_2$, THF, H$_2$O, 5° C.

N,N-di(prop-2-en-1-yl)benzene-1,4-diamine (1.00 g, 5.31 mmol) was added to a stirring solution of aluminium sulfate hexadecahydrate (3.73 g, 5.68 mmol) in distilled water (10 mL). To the reaction mixture was added sequentially a solution of sodium thiosulfate (3.03 g, 12.21 mmol) in distilled water (5 ml) and a solution of zinc chloride (0.77 g, 5.57 mmol) in distilled water (1 ml). THF (4 ml) was added and the reaction mixture was cooled to 5° C. in an ice/water bath, and a solution of sodium persulfate (1.28 g, 5.31 mmol) in distilled water (3 ml) was added drop-wise over 15 min. The reaction mixture was stirred for 2 h at 5° C. then left to rise to room temperature (22° C.). After 39 h, the aqueous phase was decanted and the sticky green solid was collected by filtration and washed with water (2×80 ml), Et$_2$O (5×50 ml) and acetone (5×100 ml). The solid obtained was dried at 74° C. for 2 h to give the title compound (0.30 g, 18%) as a pale green solid.

Mp 162-164° C. (decomposition)

$\upsilon_{max}$ (KBr)/cm$^{-1}$ 3433 (NH), 3347 (NH), 3228 (C—H), 2987 (C—H), 2922 (C—H), 1639 (alkene C=C), 1509 (Ar C=C), 1183 (O=S=O), 1019 (O=S=O).

$\delta_H$(400 MHz, DMSO-d$_6$): 3.93 (d, J=3.9 Hz, 4H, NCH$_2$) 5.12-5.16 (m, 4H, =CH$_2$), 5.82 (ddt, J=5.1, 9.8, 17.6 Hz, 2H, =CH), 6.76 (d, J=7.8 Hz, 1H, Ar—H), 6.95 (br s, 1H, Ar—H), 7.18 (d, J=9.0 Hz, 1H, Ar—H), 8.80-10.18 (br s, 3H, NH$_3$)

$\delta_C$(100 MHz, DMSO-d$_6$): 53.18 (NCH$_2$), 114.16, 117.09, 120.75, 124.28, 127.58, 133.71, 147.82

Mass Spec (m/z) ESI high resolution: calculated: 301.0681. found: 301.0676 [M+H]$^+$; 221.1104 [(M+H)—SO$_3$]$^+$ Example 2

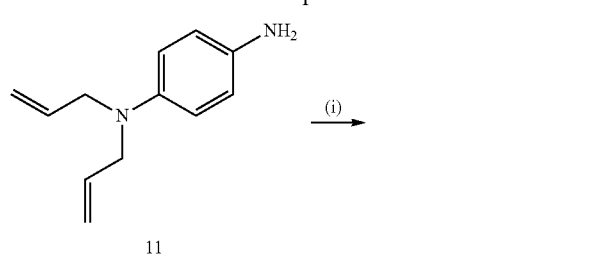

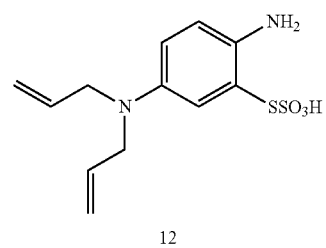

(i): Na$_2$S$_2$O$_3$·5H$_2$O, Na$_2$S$_2$O$_8$, MeOH, H$_2$O, 5° C.

A stirred solution of N,N-di(prop-2-en-1-yl)benzene-1,4-diamine (1.00 g, 5.31 mmol) in MeOH (14 ml) and water (16 ml) was cooled to 5° C. in an ice/water bath, and a solution of sodium persulfate (1.28 g, 5.31 mmol) was added dropwise over 15 min. The reaction mixture was stirred for 2 h at 5° C. then left to rise to room temperature (22° C.) over 1 h. The reaction mixture was then extracted with DCM (3×40 ml) and the aqueous phase was neutralized with sat NaHCO$_3$. After 48 h at room temperature (21-23° C.) the solid that had precipitated was collected by filtration and washed with water (50 ml) and acetone (4×50 ml). The solid obtained was dried at 74° C. for 5 h to give the title compound (0.31 g, 19%) as a green solid.

Mp 158-160° C. (decomp.)

$\upsilon_{max}$ (KBr)/cm$^{-1}$ 3433 (NH), 3347 (NH), 3228 (C—H), 3070 (C—H), 2987 (C—H), 2923 (C—H), 1639 (alkene C=C), 1508 (Ar C=C), 1240 (S=O), 1185 (C—N), 1019 (S=O)

$\delta_H$(400 MHz, DMSO-d$_6$): 3.92 (d, J=5.1 Hz, 4H, NCH$_2$) 5.12-5.17 (m, 4H, =CH$_2$), 5.81 (ddt, J=5.1, 9.8, 17.6 Hz, 2H, =CH), 6.75 (dd, J=9.0, 2.7 Hz, 1H, Ar—H), 6.93 (d, J=2.4 Hz, 1H, Ar—H), 7.13 (d, J=8.6 Hz, 1H, Ar—H), 8.80-9.70 (br s, 3H, NH$_3$)

$\delta_C$(100 MHz, DMSO-d$_6$): 53.23 (NCH$_2$), 114.38, 117.18, 120.86, 123.93, 127.29, 133.75, 147.55

Preparation of allylthioninium chloride (13)

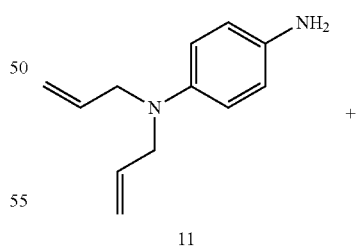

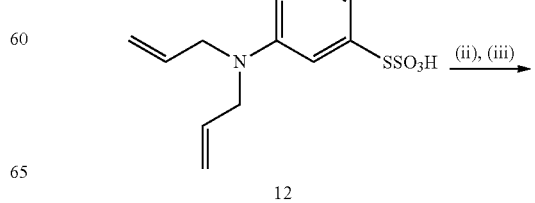

-continued

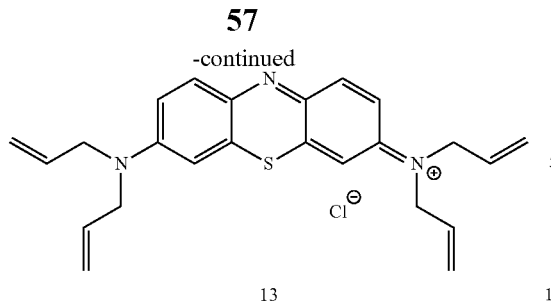

13

(ii): Na$_2$S$_2$O$_8$, H$_2$SO$_4$, H$_2$O, 6M NaOH, 5° C., (iii): CuSO$_4$, HCl, H$_2$O, 85° C., NaCl -continued

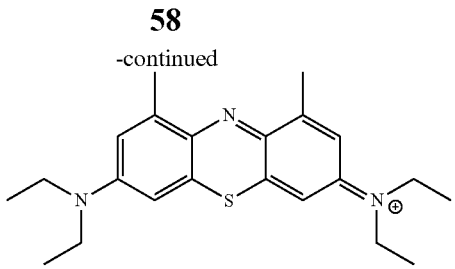

15

(i): Na$_2$S$_2$O$_3$·5H$_2$O, Na$_2$S$_2$O$_8$, H$_2$O, MeOH, Na$_2$CO$_3$, EtOAc, DCM

To a stirred suspension of 2-amino-5-N,N-di(prop-2-en-1-yl)aminophenylthiosulfonic acid (0.500 g, 1.66 mmol) in distilled water (10 ml) at 5° C. was added a pre-cooled mixture of N,N-di(prop-2-en-1-yl)aniline (0.288 g, 1.66 mmol) and concentrated sulphuric acid (0.163 g, 1.66 mmol) in distilled water (1 ml). The pH of the mixture was adjusted to pH ~7.5 using 6 M sodium hydroxide (~400 ul). A solution of sodium persulfate (0.395 g, 1.66 mmol) in water (2 ml) was added drop-wise over a period of 15 min. The reaction mixture was stirred for 1 hour at 5° C. and then warmed to room temperature (22° C.) over a 1 hour period. The solid was collected by filtration and washed with water (4×30 ml). To the filtrate was added copper (II) sulphate (50 mg, 0.3 mmol) and the solution was heated at 85° C. for 20 min. The reaction mixture was left to cool to room temperature (22° C.) and sodium chloride (10 g, 171 mmol) was added and the mixture was stirred for 1 h. The reaction mixture was then extracted with DCM (4×30 ml) and the combined organics were dried (Na$_2$SO$_4$) and the solvent was removed under reduced pressure to give a blue oil that was purified by column chromatography (10% MeOH in DCM) to give 13 as a dark blue solid.

$\upsilon_{max}$ (KBr)/cm$^{-1}$ 3424 (water, O—H), 3083 (C—H), 3013 (C—H), 2921 (C—H), 2854 (C—H), 1638 (alkene C═C), 1593 (Ar C═C)

$\delta_H$(400 MHz, CD$_3$OD): 4.36 (ddd, J=1.6, 1.6, 4.7 Hz, 8H, NCH$_2$), 5.26 (ddt, J=1.2, x, 17.2 Hz, 2H, ═CH$_2$), 5.32 (ddt, J=1.2, x, 10.8 Hz, 2H, ═CH$_2$), 5.99 (ddt, J=5.1, 10.2, 17.2 Hz, 4H, ═CH), 7.38 (d, J=2.8 Hz, 2H), 7.49 (dd, J=2.8, 9.4 Hz, 2H), 8.02 (d, J=9.7 Hz, 2H)

$\delta_C$(100 MHz, CD$_3$OD): 53.52 (NCH$_2$), 106.3 (Ar—C), 116.9 (═CH$_2$), 119.4 (Ar—C), 130.82 (═CH), 135.1 (Ar—C), 136.1 (Ar—C), 138.52 (Ar—C), 154.2 (Ar—C)

Mass Spec (m/z) ESI high resolution: calculated: 388.1842. found: 388.1481 [M—Cl]$^+$; 348.1530 [(M—Cl)—CH$_2$CHCH$_2$]$^+$, 268.1747 [(M—Cl)-3(CH$_2$CHCFl$_2$)]$^+$.

Synthesis 7

Bis-diethylamino-1,9-dimethyl-phenothiazin-5-ylium (15)

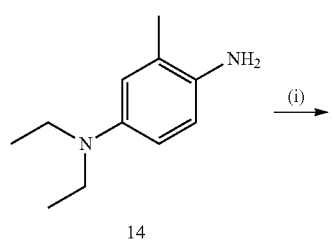

14

N$^4$,N$^4$-Dimethyl-2-methyl-1,4-phenylene diamine monohydrochloride (6.0 g, 27.9 mmol, 1.0 eq.) was dissolved in water (80 cm$^3$), and methanol (20 cm$^3$) added. The solution was stirred by overhead stirrer and cooled to an internal temperature of ~2° C. Sodium thiosulfate (7.6 g, 30.1 mmol, 1.1 eq.) was dissolved in H$_2$O (10 cm$^3$) and added to the reaction in one portion. Sodium persulfate (6.65 g, 27.9 mmol, 1.0 eq.) was dissolved in water (20 cm$^3$) and added to the reaction drop-wise over 18 minutes. During the addition the internal temperature was held between 1.7 and 2.7° C. The solution was allowed to warm to 21° C. over ~1 hour, and stirred at this temperature for a further 3 hours.

The pH of the medium was increased from 1.75 to 7.00 by addition of a saturated sodium carbonate solution, and volatiles were removed in vacuo. The solution was extracted with ethyl acetate (3×100 cm$^3$). Upon the development of a characteristic deep blue colour in the aqueous residue, the solution was extracted with dichloromethane (100 cm$^3$), the extract dried with magnesium sulfate and solvent removed in-vacuo to yield an intensely blue oil.

HPLC analysis on an SBCN column using method "relsub.m" showed only one significant peak at RT=25.056 minutes, $\lambda_{max}$ of peak=657 nm.

$\delta_H$(400 MHz, CD$_3$OD) 7.29 (2H, s, Ar), 7.16 (2H, s, Ar), 3.69 (8H, q, J 4.6, CH$_2$), 2.71 (6H, s, CH$_3$), 1.33 (12H, t, J 4.6, CH$_3$).

Mass Spec (m/z) ESI low resolution: calculated: 368.6. found: 369 [M+Hl]$^+$.

REFERENCES

The following references are hereby incorporated by reference in their, entirety:

WO 2006/032879

Badische Anilin- and Soda-Fabrik, 1877, "Verfahren Zur Darstellung Blauer Farbstoffe Aus Dimethyl-Anilin Und Anderen Tertiaren Aromatischen Monaminen," German Patent No. 1886, published 15 Dec. 1877.

Bernthsen, August, 1885a, "Studien in der Methylenblaugruppe," Justus Liebig's Annalen der Chemie, Band 230, pp. 73-136.

Bernthsen, August, 1885b, "Studien in der Methylenblaugruppe," Justus Liebig's Annalen der Chemie, Band 230, pp. 137-211.

Bernthsen, August, 1889, "Studien in der Methylenblaugruppe," Justus Liebig's Annalen der Chemie, Band 251, pp. 1-96.

Colour Index, Vol. 4 (3rd Edition, 1971), p. 4470, Entry Number 52015.

Fierz-David and Blangley, 1949, "F. Oxazine and Thiazine Dyes," in: *Fundamental Processes of Dye Chemistry*, published by Interscience (London, UK), pp. 308-314.

Leventis, N., et al., 1997, "Synthesis of Substituted Phenothiazines Analogous to Methylene Blue by Electrophilic and Nucleophilic Aromatic Substitutions in Tandem. A Mechanistic Perspective," Tetrahedron, Vol. 53, No. 29, pp. 10083-10092.

Lillie, R. D., et al., 1979, "Zinc Chloride Methylene Blue, I. Biological Stain History, Physical Characteristics and Approximation of Azure B Content of Commercial Samples," Stain Technology, Vol. 54, No. 1, pp. 33-39.

Ling Li and William D Jones, 2007, "Mechanistic investigation of the cobalt-catalysed selective conversion of diallylanilines to quinolines involving C—N and C—H activations", J Am Chem Soc, 129, pp. 10707-10713.

Lohr, W., Grubhoffer, N., Sohmer, I., Wittekind, D., 1975, "The azure dyes: their purification and physiochemical properties. Purification of Azure B," Stain Technology, Vol. 50 (3), pp. 149-156.

Marshall, P. N., Lewis, S. M., 1975a, "The purification of Methylene Blue and Azure B by solvent extraction and crystallisation," Stain Technology, Vol. 50 (6) pp. 375-381.

Marshall, P. N., Lewis, S. M., 1975b, "Metal contaminants in commercial dyes," Stain Technology, Vol. 50 (3), pp. 143-147.

Masuya, Hirotomo, 1992, "Phenothiazine Derivatives, Their Production and Use," European Patent Publication No 0 510 668 A2, published 28 Oct. 1992.

Wischik, C. M., et al., 1996, "Inhibition of Tau-Tau-Association," international (PCT) patent application publication number WO 96/30766 published 3 Oct. 1996.

Wischik, C. M., et al., 2002, "Materials and Methods Relating to Protein Aggregation in Neurodegenerative Disease," published international (PCT) patent application publication number WO 02/055720 published 18 Jul. 2002.

Yi-Chun Hsu, Kim-Hong Gan and Shyh-Chyun Yang, 2005, "Palladium-catalysed allylation of acidic and less nucleophilic anilines using allylic alcohols directly", Chem Pharm Bull, Vol, 53 (10), pp. 1266-1269.

The invention claimed is:

1. A method for the preparation of a diaminophenothiazinium compound, the method comprising the steps of (i) Thiosulfonic Acid Formation (TSAF); and (ii) Oxidative Coupling (OC);

wherein the diaminophenothiazinium compound has the following formula:

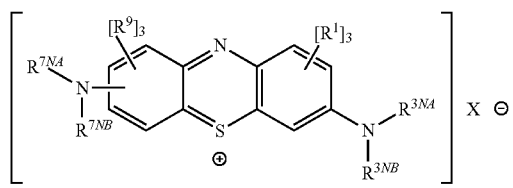

and:

each of —$R^1$ and —$R^9$ is independently —H or —$R^A$;

and each —$R^A$ is independently selected from $C_{1-4}$alkyl; $C_{2-4}$alkenyl; halogenated $C_{1-4}$alkyl; $C_{5-10}$aryl; halogenated $C_{5-10}$aryl; $C_{1-4}$alkylene-$C_{5-10}$aryl and halogenated $C_{1-4}$alkylene-$C_{5-10}$aryl;

each of —$R^{3NA}$ and —$R^{3NB}$ is independently selected from: $C_{1-4}$alkyl; $C_{2-4}$alkenyl; halogenated $C_{1-4}$alkyl; $C_{5-10}$aryl; halogenated $C_{5-10}$aryl; $C_{1-4}$alkylene-$C_{5-10}$aryl and halogenated $C_{1-4}$alkylene-$C_{5-10}$aryl;

each of —$R^{7NA}$ and —$R^{7NB}$ is independently selected from: $C_{1-4}$alkyl; $C_{2-4}$alkenyl; halogenated $C_{1-4}$alkyl; $C_{5-10}$aryl; halogenated $C_{5-10}$aryl; $C_{1-4}$alkylene-$C_{5-10}$aryl and halogenated $C_{1-4}$alkylene-$C_{5-10}$aryl; and $X^-$ is an anionic counter ion;

wherein step (i) Thiosulfonic Acid Formation (TSAF) comprises a step in which a compound of formula I is oxidized in the presence of a thiosulfate and an oxidizing agent selected from sodium persulfate, potassium persulfate, and ammonium persulfate to give a compound of formula II:

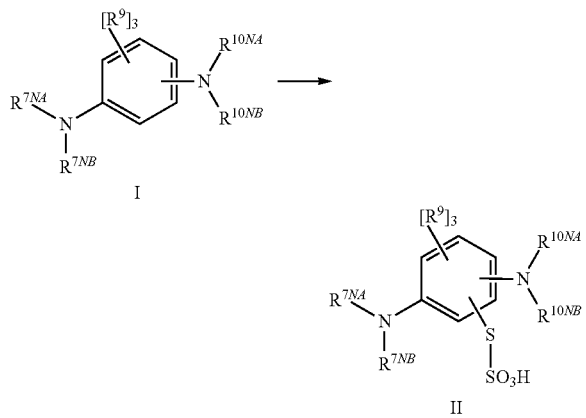

wherein —$R^9$, $R^{7NA}$ and —$R^{7NB}$ are as previously defined; and each of —$R^{10NA}$ and —$R^{10NB}$ is independently selected from: —H; $C_{1-4}$alkyl; $C_{2-4}$alkenyl; halogenated $C_{1-4}$alkyl; $C_{5-10}$aryl; halogenated $C_{5-10}$aryl; $C_{1-4}$alkylene-$C_{5-10}$aryl and halogenated $C_{1-4}$alkylene-$C_{5-10}$aryl;

and wherein step (ii) Oxidative Coupling (OC) comprises a step in which a compound of formula IIa is oxidatively coupled to a compound of formula III, using an oxidising agent selected from sodium persulfate, potassium persulfate, or ammonium persulfate, to give a compound of formula IV:

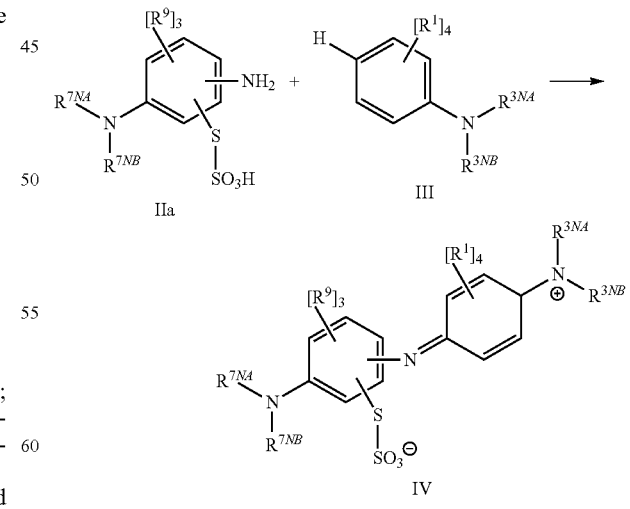

wherein:

each of —$R^1$ and —$R^9$ is independently —H or —$R^A$; —$R^A$, —$R^{3NA}$, —$R^{3NB}$, —$R^{7NA}$ and —$R^{7NB}$ are as previously defined.

2. The method according to claim 1, wherein each —$R^9$ is independently selected from: —H; $C_{1-4}$alkyl; $C_{2-4}$alkenyl; and halogenated $C_{1-4}$alkyl.

3. The method according to claim 2, wherein each —$R^9$ is —H.

4. The method according to claim 2, wherein at least one —$R^9$ is independently selected from: $C_{1-4}$alkyl; $C_{2-4}$alkenyl; and halogenated $C_{1-4}$alkyl.

5. The method according to claim 1, wherein the thiosulfate is or comprises $Na_2S_2O_3$ or a hydrate thereof.

6. The method according to claim 1, wherein the amine, I, is added first, before the thiosulfate is added.

7. The method according to claim 1, wherein in the thiosulfonic acid formation step, the thiosulfate is added before the persulfate is added.

8. The method according to claim 1, wherein the thiosulfonic acid formation step is performed in an aqueous medium comprising an organic solvent.

9. The method according to claim 1, wherein the thiosulfonic acid formation step is performed in an aqueous medium comprising a surfactant.

10. The method according to claim 1, wherein the thiosulfonic acid formation step is performed in an aqueous medium and the pH of the aqueous medium prior to the addition of the thiosulfate and persulfate is in the range of pH 2 to 7.

11. The method according to claim 1, wherein each of —$R^{10NA}$ and —$R^{10NB}$ is independently selected from: —H; $C_{1-4}$alkyl; $C_{2-4}$alkenyl; and halogenated $C_{1-4}$alkyl.

12. The method according to claim 1, wherein I and II are compounds of formula Ib and IIb respectively:

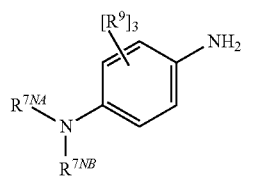

Ib

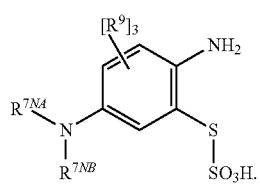

IIb

13. The method according to claim 12, wherein Ib and IIb are A and B respectively:

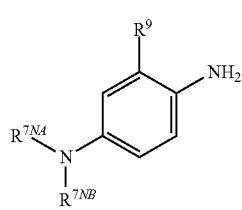

A

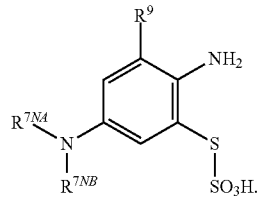

B

14. The method according to claim 1, wherein at least one of each of —$R^1$ and —$R^9$ is independently selected from: $C_{1-4}$alkyl; $C_{2-4}$alkenyl; and halogenated $C_{1-4}$alkyl.

15. The method according to claim 1, wherein II and IV are compounds of formula IIb and IVa respectively:

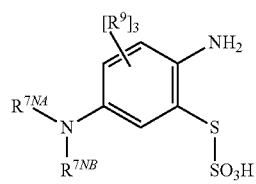

IIb

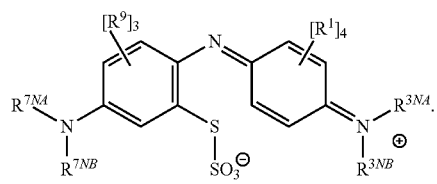

IVa

16. The method according to claim 1, wherein IIb, III and IVa are IIb, IIIa and V respectively:

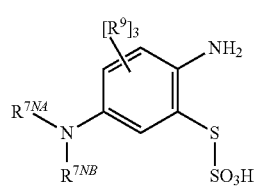

IIb

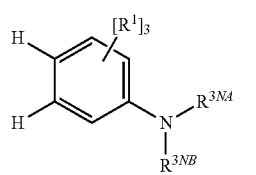

IIIa

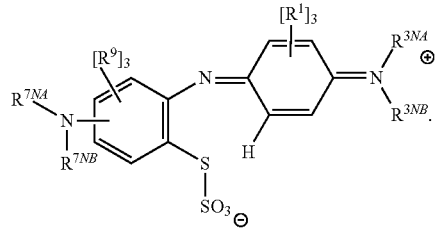

V

17. The method according to claim 1, wherein the aniline, III, is added before the persulfate is added.

18. The method according to claim 1, wherein the aniline, III, is added in a mixture with aqueous acid.

19. The method according to claim 1, wherein the oxidative coupling is performed under basic conditions.

20. The method according to claim 1, wherein the zwitterionic intermediate IV is isolated and purified.

21. The method according to claim 20, wherein the isolation and purification is by filtration.

22. A method for the preparation of a diaminophenothiazinium compound according to claim 1, comprising both (i) Thiosulfonic Acid Formation (TSAF) and (ii) Oxidative Coupling (OC).

23. The method according to claim 1, wherein each of —$R^{7NA}$ and —$R^{7NB}$ is independently selected from: $C_{1-4}$alkyl; $C_{2-4}$alkenyl; and halogenated $C_{1-4}$alkyl.

24. The method according to claim 1, wherein each of —$R^{7NA}$ and —$R^{7NB}$ is independently $C_{1-4}$alkyl.

25. The method according to claim 1, wherein each of —$R^1$ and —$R^9$ is independently selected from: —H; $C_{1-4}$alkyl; $C_{2-4}$alkenyl; and halogenated $C_{1-4}$alkyl.

26. The method according to claim 25, wherein each of —$R^1$ and —$R^9$ is —H.

27. The method according to claim 1, wherein each of —$R^{10NA}$ and —$R^{10NB}$ is —H.

28. The method according to claim 1, wherein each of —$R^{3NA}$ and —$R^{3NB}$ is independently selected from: $C_{1-4}$alkyl; $C_{2-4}$alkenyl; and halogenated $C_{1-4}$alkyl.

29. The method according to claim 28, wherein each of —$R^{3NA}$ and —$R^{3NB}$ is independently $C_{1-4}$alkyl.

30. The method according to claim 1, further comprising the step of Ring Closure (RC), in which a compound of formula V is subjected to ring closure to give a compound of formula VI:

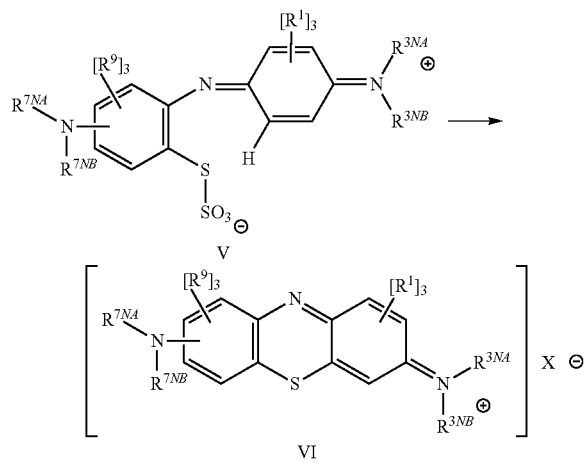

wherein each of —$R^1$ and —$R^9$ is independently —H or —$R^A$;

and each —$R^A$ is independently selected from $C_{1-4}$alkyl; $C_{2-4}$alkenyl; halogenated $C_{1-4}$alkyl; $C_{5-10}$aryl; halogenated $C_{5-10}$aryl; $C_{1-4}$alkylene-$C_{5-10}$aryl and halogenated $C_{1-4}$alkylene-$C_{5-10}$aryl;

each of —$R^{3NA}$ and —$R^{3NB}$ is independently selected from: $C_{1-4}$alkyl; $C_{2-4}$alkenyl; halogenated $C_{1-4}$alkyl; $C_{5-10}$aryl; halogenated $C_{5-10}$aryl; $C_{1-4}$alkylene-$C_{5-10}$aryl and halogenated $C_{1-4}$alkylene-$C_{5-10}$aryl;

each of —$R^{7NA}$ and —$R^{7NB}$ is independently selected from: $C_{1-4}$alkyl; $C_{2-4}$alkenyl; halogenated $C_{1-4}$alkyl; $C_{5-10}$aryl; halogenated $C_{5-10}$aryl; $C_{1-4}$alkylene-$C_{5-10}$aryl and halogenated $C_{1-4}$alkylene-$C_{5-10}$aryl; and $X^-$ is an anionic counter ion.

31. The method according to claim 30, wherein compounds V and VI are D and E respectively:

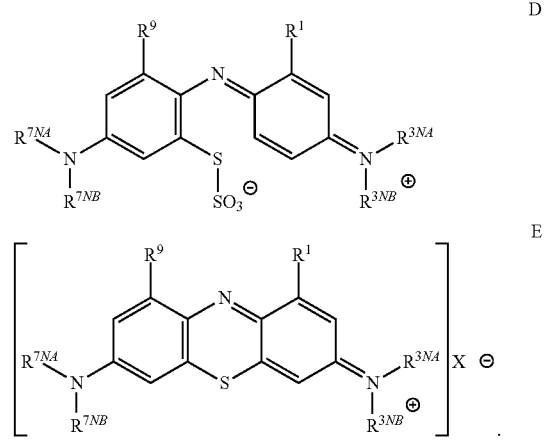

32. The method according to claim 30, wherein ring closure is achieved by treatment with an oxidizing agent.

33. The method according to claim 32, wherein the oxidizing agent is or comprises Cu(II), or the oxidizing agent is or comprises activated manganese dioxide ($MnO_2$).

34. The method according to claim, further comprising the step of Chloride Salt Formation (CSF) in which a compound of formula VI is reacted with chloride, to give a compound of formula VII:

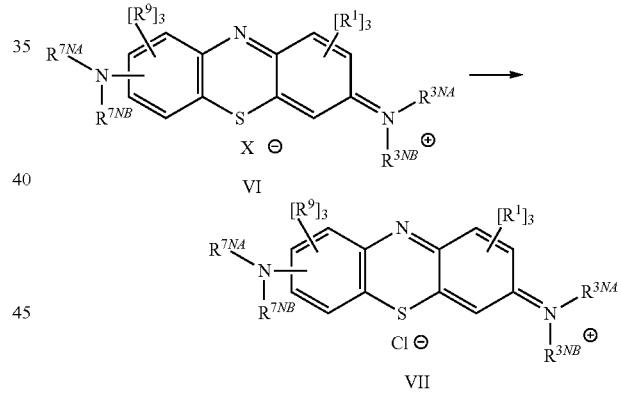

wherein:
each of —$R^1$ and —$R^9$ is independently —H or —$R^A$;
and each —$R^A$ is independently selected from $C_{1-4}$alkyl; $C_{2-4}$alkenyl; halogenated $C_{1-4}$alkyl; $C_{5-10}$aryl; halogenated $C_{5-10}$aryl; $C_{1-4}$alkylene-$C_{5-10}$aryl and halogenated $C_{1-4}$alkylene-$C_{5-10}$aryl;
each of —$R^{3NA}$ and —$R^{3NB}$ is independently selected from: $C_{1-4}$alkyl; $C_{2-4}$alkenyl; halogenated $C_{1-4}$alkyl; $C_{5-10}$aryl; halogenated $C_{5-10}$aryl; $C_{1-4}$alkylene-$C_{5-10}$aryl and halogenated $C_{1-4}$alkylene-$C_{5-10}$aryl;
each of —$R^{7NA}$ and —$R^{7NB}$ is independently selected from: $C_{1-4}$alkyl; $C_{2-4}$alkenyl; halogenated $C_{1-4}$alkyl; $C_{5-10}$aryl; halogenated $C_{5-10}$aryl; $C_{1-4}$alkylene-$C_{5-10}$aryl and halogenated $C_{1-4}$alkylene-$C_{5-10}$aryl; and
$X^-$ is an anionic counter ion.

35. The method according to claim 34, wherein VI is reacted with a chloride salt or hydrochloric acid as a source of chloride.

36. The method according to claim 1, wherein the method comprises the step of (i) Thiosulfonic Acid Formation (TSAF); and further comprises a step of Cr-Mediated Oxidative Coupling (Cr—OC), in which a compound of formula IIa, is oxidatively coupled a compound of formula III, using an oxidizing agent that is or comprises Cr(VI), to give a compound of formula IV,

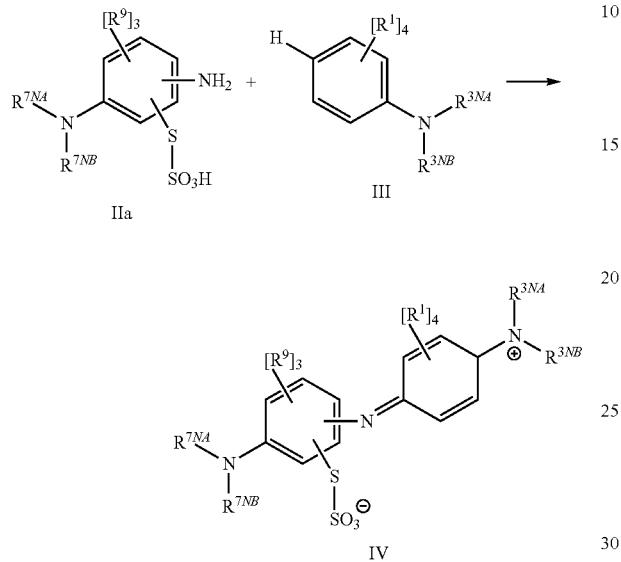

wherein:

each of —$R^1$ and —$R^9$ is independently —H or —$R^A$;

each —$R^A$ is independently selected from $C_{1-4}$alkyl; $C_{2-4}$alkenyl; halogenated $C_{1-4}$alkyl; $C_{5-10}$aryl; halogenated $C_{5-10}$aryl; $C_{1-4}$alkylene-$C_{5-10}$aryl and halogenated $C_{1-4}$alkylene-$C_{5-10}$aryl;

each of —$R^{3NA}$ and —$R^{3NB}$ is independently selected from: $C_{1-4}$alkyl; $C_{2-4}$alkenyl; halogenated $C_{1-4}$alkyl; $C_{5-10}$aryl; halogenated $C_{5-10}$aryl; $C_{1-4}$alkylene-$C_{5-10}$aryl and halogenated $C_{1-4}$alkylene-$C_{5-10}$aryl; and each of —$R^{7NA}$ and —$R^{7NB}$ is independently selected from: $C_{1-4}$alkyl; $C_{2-4}$alkenyl; halogenated $C_{1-4}$alkyl; $C_{5-10}$aryl; halogenated $C_{5-10}$aryl; $C_{1-4}$alkylene-$C_{5-10}$aryl and halogenated $C_{1-4}$alkylene-$C_{5-10}$aryl.

37. The method according to claim 1, wherein the method comprises the step of (ii) Oxidative Coupling (OC); and further comprises a preceding step of Cr-Mediated Thiosulfonic Acid Formation (Cr-TSAF), in which a compound of formula I is oxidized in the presence of a thiosulfate and an oxidizing agent that is or comprises Cr(VI) to give a compound of formula II

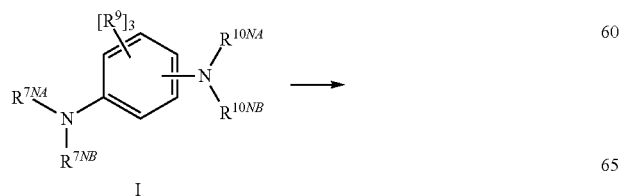

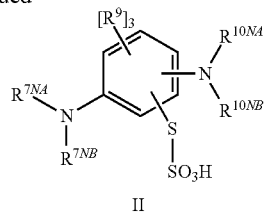

wherein each —$R^9$ is independently —H or —$R^A$;

each —$R^A$ is independently selected from $C_{1-4}$alkyl; $C_{2-4}$alkenyl; halogenated $C_{1-4}$alkyl; $C_{5-10}$aryl; halogenated $C_{5-10}$aryl; $C_{1-4}$alkylene-$C_{5-10}$aryl and halogenated $C_{1-4}$alkylene-$C_{5-10}$aryl;

each of —$R^{7NA}$ and —$R^{7NB}$ is independently selected from: $C_{1-4}$alkyl; $C_{2-4}$alkenyl; halogenated $C_{1-4}$alkyl; $C_{5-10}$aryl; halogenated $C_{5-10}$aryl; $C_{1-4}$alkylene-$C_{5-10}$aryl and halogenated $C_{1-4}$alkylene-$C_{5-10}$aryl;

and each of —$R^{10NA}$ and —$R^{10NB}$ is independently selected from: —H; $C_{1-4}$alkyl; $C_{2-4}$alkenyl; halogenated $C_{1-4}$alkyl; $C_{5-10}$aryl; halogenated $C_{5-10}$aryl; $C_{1-4}$alkylene-$C_{5-10}$aryl and halogenated $C_{1-4}$alkylene-$C_{5-10}$aryl.

38. The method according to claim 1 further comprising the step of Nitrosyl Reduction (NR), in which a compound of formula VIII is reduced to form a compound of formula Ia:

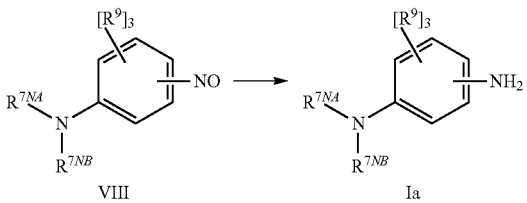

wherein each —$R^9$ is independently —H or —$R^A$;

and each —$R^A$ is independently selected from $C_{1-4}$alkyl; $C_{2-4}$alkenyl; halogenated $C_{1-4}$alkyl; $C_{5-10}$aryl; halogenated $C_{5-10}$aryl; $C_{1-4}$alkylene-$C_{5-10}$aryl and halogenated $C_{1-4}$alkylene-$C_{5-10}$aryl; and each of —$R^{7NA}$ and —$R^{7NB}$ is independently selected from: $C_{1-4}$alkyl; $C_{2-4}$alkenyl; halogenated $C_{1-4}$alkyl; $C_{5-10}$aryl; halogenated $C_{5-10}$aryl; $C_{1-4}$alkylene-$C_{5-10}$aryl and halogenated $C_{1-4}$alkylene-$C_{5-10}$aryl.

39. The method according to claim 38, wherein VIII and Ia are G and A respectively:

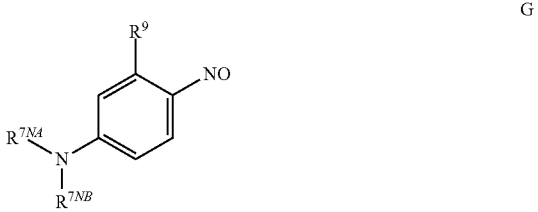

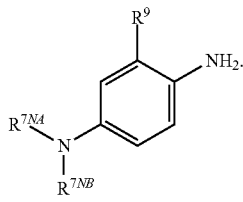

A

40. The method according to claim 1 further comprising the step of Nitrosylation (NOS), wherein a compound of formula IX is nitrosylated to give a compound of formula VIII:

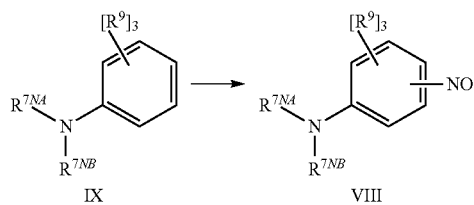

wherein:
each —$R^9$ is independently —H or —$R^A$
and each —$R^A$ is independently selected from $C_{1-4}$alkyl; $C_{2-4}$alkenyl; halogenated $C_{1-4}$alkyl; $C_{5-10}$aryl; halogenated $C_{5-10}$aryl; $C_{1-4}$alkylene-$C_{5-10}$aryl and halogenated $C_{1-4}$alkylene-$C_{5-10}$aryl; and
each of —$R^{7NA}$ and —$R^{7NB}$ is independently selected from: $C_{1-4}$alkyl; $C_{2-4}$alkenyl; halogenated $C_{1-4}$alkyl; $C_{5-10}$aryl; halogenated $C_{5-10}$aryl; $C_{1-4}$alkylene-$C_{5-10}$aryl and halogenated $C_{1-4}$alkylene-$C_{5-10}$aryl.

41. The method according to claim 40, wherein IX and VIII are H and G respectively:

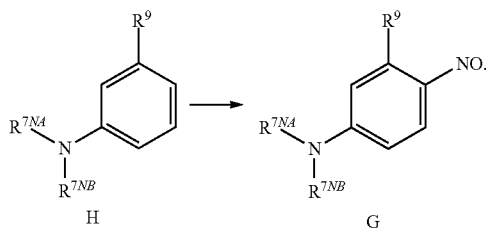

* * * * *